United States Patent
Hwang et al.

(10) Patent No.: US 7,927,719 B2
(45) Date of Patent: *Apr. 19, 2011

(54) SILANYLAMINE-BASED COMPOUND, METHOD OF PREPARING THE SAME AND ORGANIC LIGHT EMITTING DEVICE INCLUDING ORGANIC LAYER COMPRISING THE SILANYLAMINE-BASED COMPOUND

(75) Inventors: Seok-Hwan Hwang, Suwon-si (KR); Young-Kook Kim, Suwon-si (KR); Yoon-Hyun Kwak, Suwon-si (KR); Chang-Ho Lee, Suwon-si (KR)

(73) Assignee: Samsung Mobile Display Co., Ltd., Yongin (KR)

( * ) Notice: Subject to any disclaimer, the term of this patent is extended or adjusted under 35 U.S.C. 154(b) by 604 days.

This patent is subject to a terminal disclaimer.

(21) Appl. No.: 11/777,204

(22) Filed: Jul. 12, 2007

(65) Prior Publication Data
US 2008/0106188 A1    May 8, 2008

(30) Foreign Application Priority Data

Nov. 8, 2006 (KR) ...................... 10-2006-0110187

(51) Int. Cl.
*H01L 51/54* (2006.01)
*C07F 7/02* (2006.01)
*C07F 7/04* (2006.01)
*H01J 1/62* (2006.01)

(52) U.S. Cl. ........ 428/690; 428/917; 313/504; 313/506; 548/406; 556/413

(58) Field of Classification Search ............... None
See application file for complete search history.

(56) References Cited

U.S. PATENT DOCUMENTS

| 2,960,517 A | 11/1960 | Schnabel |
| 4,356,429 A | 10/1982 | Tang |

(Continued)

FOREIGN PATENT DOCUMENTS

DE    101 14 970 A1    10/2002

(Continued)

OTHER PUBLICATIONS

Machine tanslation for KR 10-2006-0048267, published May 2006.*

(Continued)

*Primary Examiner* — Dawn L. Garrett
(74) *Attorney, Agent, or Firm* — Christie, Parker & Hale, LLP

(57) ABSTRACT

Silanylamine-based compounds represented by Formula 1 are provided. Methods of preparing the compounds and organic light emitting devices including organic layers comprising the silanylamine-based compounds are also provided.

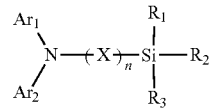

Formula 1

The silanylamine-based compounds have excellent electrical stability and electron transporting capabilities. Thus, the silanylamine-based compounds may be effectively used for red, green, blue, and white fluorescent and phosphorescent materials used to form hole injection layers, hole transport layers, and emissive layers in organic light emitting devices. Organic light emitting devices using these compounds have high efficiency, low driving voltages, high luminance and long lifetimes.

22 Claims, 2 Drawing Sheets

U.S. PATENT DOCUMENTS

| | | | |
|---|---|---|---|
| 6,465,115 | B2 | 10/2002 | Shi et al. |
| 6,596,415 | B2 | 7/2003 | Shi et al. |
| 7,365,198 | B2 * | 4/2008 | Saitoh et al. ............... 544/229 |
| 2003/0211358 | A1 | 11/2003 | Kitano et al. |
| 2008/0171227 | A1 * | 7/2008 | Kwak et al. ................ 428/690 |
| 2009/0206745 | A1 * | 8/2009 | Hwang et al. ............... 313/504 |

FOREIGN PATENT DOCUMENTS

| | | |
|---|---|---|
| DE | 10 2004 020 A1 | 7/2005 |
| JP | 5-323634 | 12/1993 |
| JP | 11-329734 | 11/1999 |
| JP | 2006-010555 | 1/2006 |
| JP | 2006-056957 | 3/2006 |
| JP | 2006-516136 (T) | 6/2006 |
| KR | 10-2005-0078472 | 8/2005 |
| KR | 10-0525611 | 12/2005 |
| KR | 10-2006-0048267 | 5/2006 |

OTHER PUBLICATIONS

Patent Abstracts of Japan, Publication No. 11-329734; Publication Date: Nov. 30, 1999; in the name of Yoshiharu Sato et al.

Korean Patent Abstracts, Publication No. 1020050078472 A; Publication Date: Aug. 5, 2005; in the name of Seok Jong Lee, et al.

European Search Report dated Jan. 21, 2008, for European application 07119446.8, indicating relevance of the cited references in this IDS.

English abstract, XP-002463376, Japan patent 05-323634, published Dec. 7, 1993, in the name of Hisahiro Hirose.

Patent Abstracts of Japan, Publication No. 05-323634, dated Dec. 7, 1993, in the name of Hisahiro Hirose.

Korean Patent Abstracts, Publication No. 1020060048267 A; Date of Publication: May 18, 2006; in the name of Jong Sun Lee et al.

Office Action dated Sep. 27, 2007 for corresponding Korean Patent Application No. 10-2006-0110187.

Jia, Wen-Li, et al., *Blue Luminescent Organosilicon Compounds Based on 2,2'-Dipyridylaminophenyl and 2,2'-Dipyridylaminobiphenyl*, Organometallics, vol. 22, No. 2, (2003), pp. 321-327.

Japanese Office action dated Jun. 1, 2010, for corresponding Japanese Patent application 2007-135428, noting listed references in this IDS, as well as U.S. Patent No. 2,960,517 previously filed in an IDS dated Mar. 13, 2008.

\* cited by examiner

SILANYLAMINE-BASED COMPOUND, METHOD OF PREPARING THE SAME AND ORGANIC LIGHT EMITTING DEVICE INCLUDING ORGANIC LAYER COMPRISING THE SILANYLAMINE-BASED COMPOUND

CROSS-REFERENCE TO RELATED PATENT APPLICATION

This application claims priority to and the benefit of Korean Patent Application No. 10-2006-0110187, filed on Nov. 8, 2006 in the Korean Intellectual Property Office, the entire content of which is incorporated herein by reference.

BACKGROUND OF THE INVENTION

1. Field of the Invention

The present invention relates to silanylamine-based compounds, methods of preparing the same, and organic light emitting devices including organic layers comprising a silanylamine-based compound.

2. Description of the Related Art

Organic light emitting devices (OLEDs) are self-emitting devices having wide viewing angles, excellent contrast, and quick responses. Organic light emitting devices have low operating voltages and quick response times, and can realize multi-color images. Accordingly, OLEDs are being extensively researched.

A typical organic light emitting device has an anode/emissive layer/cathode structure. Organic light emitting devices can also have various other structures, such as anode/hole transport layer/emissive layer/cathode, and anode/hole transport layer/emissive layer/electron injection layer/cathode. These alternative structures are realized by further including an electron transport layer and at least one of a hole injection layer, a hole transport layer and an electron injection layer between the anode and the emissive layer, or between the emissive layer and the cathode.

Fluorene and anthracene derivatives have been used as to form the hole transport layer. However, organic light emitting devices having these hole transport layers do not have satisfactory lifetime, efficiency, and power consumption.

SUMMARY OF THE INVENTION

In one embodiment of the present invention, a material is provided for forming a red, green, blue, or white fluorescent or phosphorescent organic layer of an organic light emitting device (OLED).

According to another embodiment, an OLED includes an organic layer using the material. The OLED using the material has excellent electrical stability, high electron transporting capability, high glass transition temperature, and crystallization prevention properties. The OLED also exhibits excellent efficiency, low operating voltage, high luminance and long lifetime.

In yet another embodiment of the present invention, a method of preparing the material is provided.

According to one embodiment of the present invention, a silanylamine-based compound represented by Formula 1 below is provided.

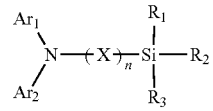

Formula 1

In Formula 1, n is an integer ranging from 1 to 5 and X is selected from a single bond, substituted and unsubstituted $C_1$-$C_{30}$ alkylene groups, substituted and unsubstituted $C_6$-$C_{30}$ arylene groups, and substituted and unsubstituted $C_2$-$C_{30}$ heteroarylene groups. $Ar_1$ and $Ar_2$ are each independently selected from hydrogen atoms, substituted and unsubstituted $C_6$-$C_{30}$ aryl groups, and substituted and unsubstituted $C_2$-$C_{30}$ heteroaryl groups. $R_1$, $R_2$ and $R_3$ are each independently selected from hydrogen atoms, substituted and unsubstituted $C_1$-$C_{30}$ alkyl groups, substituted and unsubstituted $C_2$-$C_{30}$ alkenyl groups, substituted and unsubstituted $C_2$-$C_{30}$ alkynyl groups, substituted and unsubstituted $C_1$-$C_{30}$ alkoxy groups, substituted and unsubstituted $C_6$-$C_{30}$ aryloxy groups, substituted and unsubstituted $C_6$-$C_{30}$ aryl groups, and substituted and unsubstituted $C_2$-$C_{30}$ heteroaryl groups. At least two of $R_1$, $R_2$ and $R_3$ are bonded to each other to form a saturated or unsaturated ring.

According to another embodiment of the present invention, a method of preparing a silanylamine-based compound represented by Formula 1 is provided. In one embodiment, the method includes reacting a compound represented by Formula 1a and a compound represented by Formula 1b via Reaction Scheme 1 below.

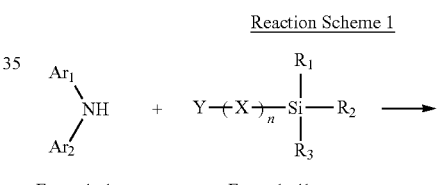

In Formulae 1a and 1b, X, n, $Ar_1$, $Ar_2$, $R_1$, $R_2$ and $R_3$ are as described above, and Y is a halogen atom.

According to another embodiment of the present invention, an organic light emitting device includes a first electrode, a second electrode, and an organic layer positioned between the first electrode and the second electrode, the organic layer including a silanylamine-based compound. The organic light emitting device including the silanylamine-based compound represented by Formula 1 exhibits low driving voltage, excellent luminance, high efficiency, high current density and has a long lifetime.

BRIEF DESCRIPTION OF THE DRAWINGS

The above and other features and advantages of the present invention will become more apparent by reference to the following detailed description when considered in conjunction with the attached drawings in which.

DETAILED DESCRIPTION OF THE INVENTION

Figure 1:
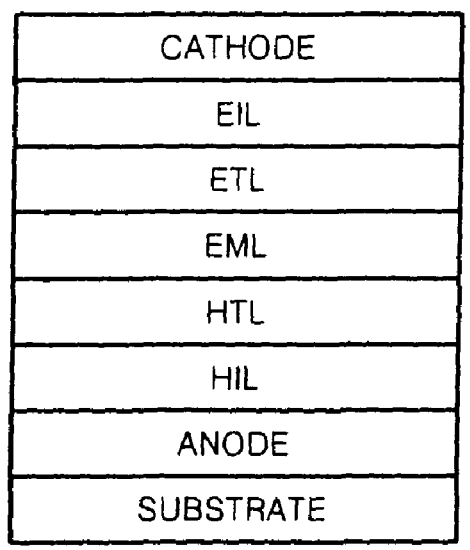
FIG. 1 is a schematic illustrating an organic light emitting device according to one embodiment of the present invention.

According to one embodiment of the present invention, a silanylamine-based compound is represented by Formula 1 below.

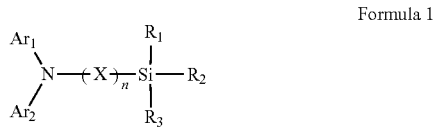

Formula 1

In Formula 1, an amine derivative is bonded to a silane derivative through a linking group —(X)$_n$— to form the silanylamine-based compound.

In Formula 1, n may be an integer ranging from 1 to 5 and X may be selected from a single bond, substituted and unsubstituted $C_1$-$C_{30}$ alkylene groups, substituted and unsubstituted $C_6$-$C_{30}$ arylene groups, and substituted and unsubstituted $C_2$-$C_{30}$ heteroarylene groups. $Ar_1$ and $Ar_2$ may be each independently selected from hydrogen atoms, substituted and unsubstituted $C_6$-$C_{30}$ aryl groups, and substituted and unsubstituted $C_2$-$C_{30}$ heteroaryl groups. $R_1$, $R_2$ and $R_3$ may be each independently selected from hydrogen atoms, substituted and unsubstituted $C_1$-$C_{30}$ alkyl groups, substituted and unsubstituted $C_2$-$C_{30}$ alkenyl groups, substituted and unsubstituted $C_2$-$C_{30}$ alkynyl groups, substituted and unsubstituted $C_1$-$C_{30}$ alkoxy groups, substituted and unsubstituted $C_6$-$C_{30}$ aryloxy groups, substituted and unsubstituted $C_6$-$C_{30}$ aryl groups, and substituted and unsubstituted $C_2$-$C_{30}$ heteroaryl groups. At least two of $R_1$, $R_2$ and $R_3$ are optionally bonded to each other to form a saturated or unsaturated ring.

Nonlimiting examples of suitable unsubstituted $C_1$-$C_{30}$ alkyl groups include methyl groups, ethyl groups, propyl groups, isobutyl groups, sec-butyl groups, pentyl groups, iso-amyl groups, and hexyl groups. At least one of the hydrogen atoms in the alkyl group may be substituted with a constituent selected from halogen atoms, hydroxy groups, nitro groups, cyano groups, amino groups, amidino groups, hydrazines, hydrazones, carboxyl groups and salts thereof, sulfonic acid groups and salts thereof, phosphoric acid groups and salts thereof, $C_1$-$C_{30}$ alkyl groups, $C_1$-$C_{30}$ alkenyl groups, $C_1$-$C_{30}$ alkynyl groups, $C_6$-$C_{30}$ aryl groups, $C_7$-$C_{20}$ arylalkyl groups, $C_2$-$C_{20}$ heteroaryl groups, $C_3$-$C_{30}$ heteroarylalkyl groups, $C_6$-$C_{30}$ aryloxy groups and —N($Z_1$)($Z_2$). In the —N($Z_1$)($Z_2$) substituent, $Z_1$ and $Z_2$ may be each independently selected from hydrogen atoms, substituted and unsubstituted $C_1$-$C_{30}$ alkyl groups, substituted and unsubstituted $C_1$-$C_{30}$ haloalkyl groups, substituted and unsubstituted $C_6$-$C_{30}$ aryl groups, substituted and unsubstituted $C_6$-$C_{30}$ haloaryl groups, and substituted and unsubstituted $C_2$-$C_{30}$ heteroaryl groups.

The unsubstituted $C_1$-$C_{30}$ alkylene group is a bivalent linking group having a structure similar to an alkyl group, and nonlimiting examples of the alkylene group include methylene groups and ethylene groups. At least one hydrogen atom in the alkylene group may be substituted with any of the substituents described above in connection with the unsubstituted $C_1$-$C_{30}$ alkyl group.

Nonlimiting examples of the unsubstituted $C_1$-$C_{30}$ alkoxy group include methoxy groups, ethoxy groups, phenyloxy groups, cyclohexyloxy groups, naphthyloxy groups, isopropyloxy groups, and diphenyloxy groups. At least one of the hydrogen atoms in the alkoxy group may be substituted with any of the substituents described above in connection with the unsubstituted $C_1$-$C_{30}$ alkyl group.

The $C_2$-$C_{30}$ alkenyl group is a hydrocarbon chain having a carbon-carbon double bond in the center or at one end of the alkyl group structure. Nonlimiting examples of suitable alkenyl groups include ethylene groups, propylene groups, butylene groups, and hexylene groups. At least one hydrogen atom in the alkenyl group may be substituted with any substituent described above in connection with the unsubstituted $C_1$-$C_{30}$ alkyl group.

The $C_2$-$C_{30}$ alkynyl group is a hydrocarbon chain having a carbon-carbon triple bond in the center or at one end of the alkyl group structure. Nonlimiting examples of suitable alkynyl groups include acetylene groups, propylacetylene groups, phenylacetylene groups, naphthylacetylene groups, isopropylacetylene groups, t-butylacetylene groups, and diphenylacetylene groups. At least one of the hydrogen atoms in the alkynyl group may be substituted with any substituent described above in connection with the unsubstituted $C_1$-$C_{30}$ alkyl group.

The $C_6$-$C_{30}$ aryl group is a carbocyclic aromatic system having from 6 to 30 carbon atoms and including at least one aromatic ring. The rings can be fused to each other or bonded to each other, for example, through a single bond. At least one hydrogen atom in the aryl group may be substituted with any of the substituents described above in connection with the unsubstituted $C_1$-$C_{30}$ alkyl group.

Nonlimiting examples of suitable unsubstituted $C_6$-$C_{30}$ aryl groups include phenyl groups, $C_1$-$C_{10}$ alkylphenyl groups (e.g., ethylphenyl groups), halophenyl groups (e.g., o-, m- and p-fluorophenyl groups, and dichlorophenyl groups), cyanophenyl groups, dicyanophenyl groups, trifluoromethoxyphenyl groups, biphenyl groups, halobiphenyl groups, cyanobiphenyl groups, $C_1$-$C_{10}$ biphenyl groups, $C_1$-$C_{10}$ alkoxybiphenyl groups, o-, m- and p-tolyl groups, o-, m- and p-cumenyl groups, mesityl groups, phenoxyphenyl groups, (α,α-dimethylbenzen)phenyl groups, (N,N'-dimethyl)aminophenyl groups, (N,N'-diphenyl)aminophenyl groups, pentalenyl groups, indenyl groups, naphthyl groups, halonaphthyl groups (e.g., fluoronaphthyl groups), $C_1$-$C_{10}$ alkylnaphthyl groups (e.g., methylnaphthyl groups), $C_1$-$C_{10}$ alkoxynaphthyl groups (e.g., methoxynaphthyl groups), cyanonaphthyl groups, anthracenyl groups, azulenyl groups, heptalenyl groups, acenaphthylenyl groups, phenalenyl groups, fluorenyl groups, anthraquinolyl groups, methylanthryl groups, phenanthrenyl groups, triphenylenyl groups, pyrenyl groups, chrysenyl groups, ethyl-chrysenyl groups, picenyl groups, perylenyl groups, chloroperylenyl groups, pentaphenyl groups, pentacenyl groups, tetraphenylenyl groups, hexaphenyl groups, hexacenyl groups, rubicenyl groups, coronenyl groups, trinaphthylenyl groups, heptaphenyl groups, heptacenyl groups, pyranthrenyl groups, and ovalenyl groups. At least one of the hydrogen atoms in the aryl group may be substituted with any of the substituents described above in connection with the unsubstituted $C_1$-$C_{30}$ alkyl group.

The unsubstituted $C_6$-$C_{30}$ arylene group is a bivalent linking group having a structure similar to the aryl group, and nonlimiting examples of the arylene group include phenylene groups and naphthylene groups. At least one hydrogen atom in the arylene group may be substituted with any of the substituents described above in connection with the unsubstituted $C_1$-$C_{30}$ alkyl group.

The unsubstituted $C_3$-$C_{30}$ heteroaryl group is a group having at least one aromatic ring in which at least one carbon atom in the aryl group is substituted with one of N, O, P and S. The aromatic rings can be fused to each other or bonded to each other, for example, through a single bond. At least one hydrogen atom in the heteroaryl group may be substituted with any of the substituents described above in connection with the unsubstituted $C_1$-$C_{30}$ alkyl group.

Nonlimiting examples of the unsubstituted $C_3$-$C_{30}$ heteroaryl group include pyrazolyl groups, imidazolyl groups, oxazolyl groups, thiazolyl groups, triazolyl groups, tetrazolyl groups, oxadiazolyl groups, pyridinyl groups, pyridazinyl groups, pyrimidinyl groups, triazinyl groups, carbazolyl groups, indolyl groups, quinolinyl groups, and isoquinolinyl groups. At least one hydrogen atom in the heteroaryl group may be substituted with any of the substituents described above in connection with the unsubstituted $C_1$-$C_{30}$ alkyl group.

The unsubstituted $C_3$-$C_{60}$ heteroarylene group is a bivalent linking group having a structure similar to the heteroaryl group, and at least one hydrogen atom in the heteroarylene group may be substituted with any of the substituents described above in connection with the unsubstituted $C_1$-$C_{30}$ alkyl group.

The unsubstituted $C_6$-$C_{30}$ aryloxy group is a group represented by —OA, where A is the aryl group, such as a phenoxy group. At least one hydrogen atom in the aryloxy group may be substituted with any of the substituents described above in connection with the unsubstituted $C_1$-$C_{30}$ alkyl group.

According to one embodiment of the present invention, in Formula 1, X may be selected from substituted and unsubstituted $C_1$-$C_{10}$ alkylene groups, substituted and unsubstituted phenylene groups, substituted and unsubstituted naphthylene groups, substituted and unsubstituted fluorenylene groups, substituted and unsubstituted anthracenylene groups, substituted and unsubstituted pyridinylene groups, substituted and unsubstituted quinolylene groups, substituted and unsubstituted isoquinolylene groups, substituted and unsubstituted anthraquinolylene groups, and substituted and unsubstituted carbazolylene groups.

Nonlimiting examples of suitable substituents for X include structures shown in Formula 2 below.

Formula 2

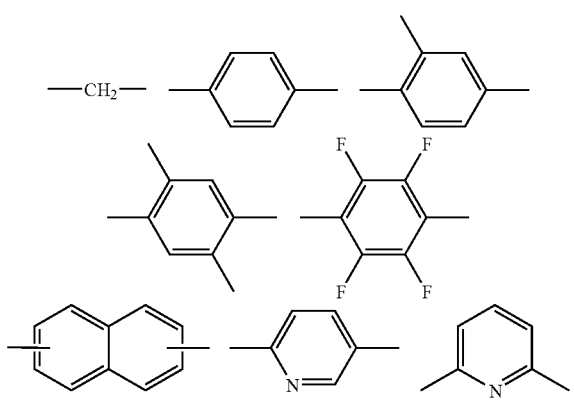

-continued

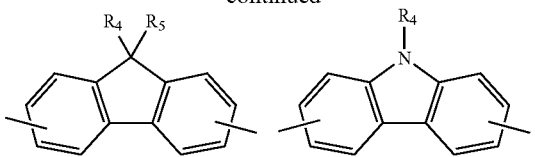

In the structures shown in Formula 2, $R_4$ and $R_5$ are each independently selected from hydrogen atoms, halogen atoms, cyano groups, hydroxyl groups, substituted and unsubstituted $C_1$-$C_{30}$ alkyl groups, substituted and unsubstituted $C_1$-$C_{30}$ alkoxy groups, substituted and unsubstituted $C_6$-$C_{30}$ aryl groups, and substituted and unsubstituted $C_3$-$C_{30}$ heteroaryl groups. In one embodiment, for example, $R_4$ and $R_5$ are each independently selected from phenyl groups and halophenyl groups.

With X and n being as described above, nonlimiting examples of suitable —(X)$_n$— linking groups include the substituents shown in Formula 3 below.

Formula 3

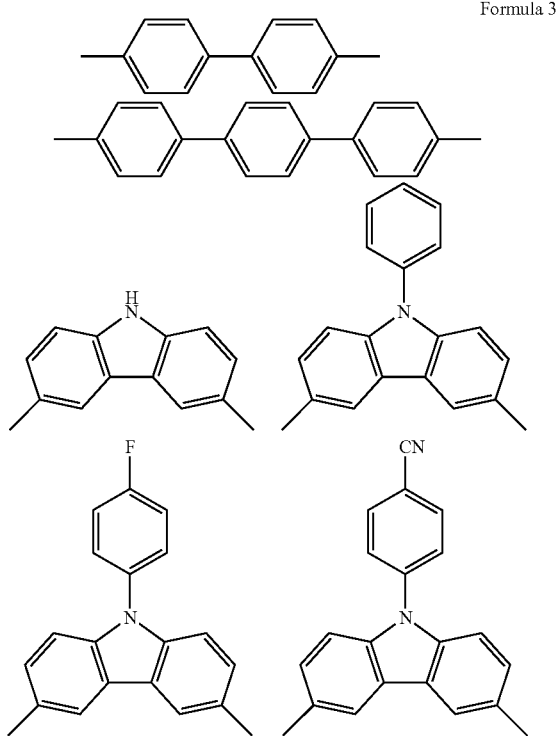

In the structures shown in Formula 3, $Ar_1$ and $Ar_2$ are each independently selected from substituted and unsubstituted $C_1$-$C_{12}$ aryl groups, and substituted and unsubstituted $C_3$-$C_{15}$ heteroaryl groups.

Nonlimiting examples of suitable substituents for $Ar_1$ and $Ar_2$ include phenyl groups, halophenyl groups, cyanophenyl groups, $C_1$-$C_5$ alkylphenyl groups, $C_1$-$C_5$ alkoxyphenyl groups, phenoxyphenyl groups, phenyl groups substituted with —N($Z_1$)($Z_2$), biphenyl groups, halobiphenyl groups, cyanobiphenyl groups, $C_1$-$C_5$ alkylbiphenyl groups, $C_1$-$C_5$ alkoxybiphenyl groups, biphenyl groups substituted with —N($Z_1$)($Z_2$), naphthyl groups, halonaphthyl groups, cyanonaphthyl groups, $C_1$-$C_5$ alkylnaphthyl groups, $C_1$-$C_5$ alkoxynaphthyl groups, phenoxynaphthyl groups, naphthyl groups substituted with —N($Z_1$)($Z_2$), fluorenyl groups, halofluorenyl groups, cyanofluorenyl groups, $C_1$-$C_5$ alkylfluorenyl groups, $C_1$-$C_5$ alkoxyfluorenyl groups, phenoxyfluorenyl groups, carbazolyl groups, halocarbazolyl groups, cyanocarbazolyl groups, $C_1$-$C_5$ alkylcarbazolyl groups, $C_1$-$C_5$ alkoxycarbazolyl groups, phenoxycarbazolyl groups, carbazolyl groups substituted with —$N(Z_1)(Z_2)$, $C_6$-$C_{12}$ arylcarbazolyl groups, $C_6$-$C_{12}$ haloarylcarbazolyl groups, pyridyl groups, halopyridyl groups, cyanopyridyl groups, $C_1$-$C_5$ alkylpyridyl groups, $C_1$-$C_5$ alkoxypyridyl groups, phenoxypyridyl groups, and pyridyl groups substituted with —$N(Z_1)(Z_2)$.

In the structures shown in Formula 3, nonlimiting examples of suitable substituents for $Z_1$ and $Z_2$ include hydrogen, substituted and unsubstituted $C_1$-$C_{30}$ alkyl groups, substituted and unsubstituted $C_1$-$C_{30}$ haloalkyl groups, substituted and unsubstituted $C_6$-$C_{30}$ aryl groups, substituted and unsubstituted $C_6$-$C_{30}$ haloaryl groups, and substituted and unsubstituted $C_2$-$C_{30}$ heteroaryl groups. In one embodiment, $Z_1$ and $Z_2$ are each independently selected from $C_6$-$C_{12}$ aryl groups, and $C_6$-$C_{12}$ haloaryl groups.

In Formula 3, nonlimiting examples of suitable substituents for $Ar_1$ and $Ar_2$ include those represented by Formula 4 below.

Formula 4

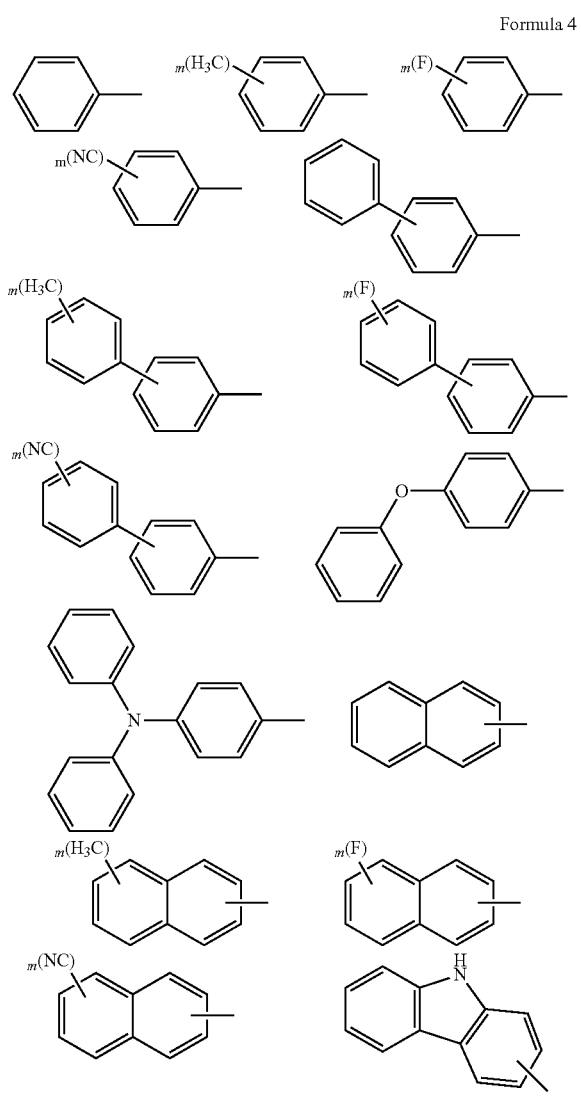

-continued

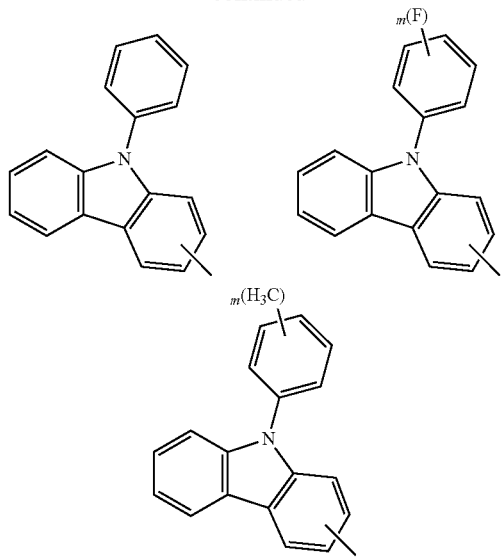

In Formula 4, m may be an integer ranging from 1 to 5, and $R_1$, $R_2$ and $R_3$ may be each independently selected from substituted and unsubstituted $C_1$-$C_{10}$ alkyl groups, substituted and unsubstituted $C_1$-$C_{10}$ alkoxy groups, substituted and unsubstituted $C_6$-$C_{12}$ aryl groups, substituted and unsubstituted $C_6$-$C_{12}$ aryloxy groups, and substituted and unsubstituted $C_3$-$C_{12}$ heteroaryl groups. Nonlimiting examples of suitable substituents for $R_1$, $R_2$ and $R_3$ include $C_1$-$C_{10}$ alkyl groups, phenyl groups, halophenyl groups, cyanophenyl groups, $C_1$-$C_{10}$ alkylphenyl groups, $C_1$-$C_{10}$ alkoxyphenyl groups, biphenyl groups, halobiphenyl groups, naphthyl groups, halonaphthyl groups, $C_1$-$C_{10}$ alkylnaphthyl groups, and $C_1$-$C_{10}$ alkoxynaphthyl groups.

Nonlimiting examples of suitable silanylamine-based compounds satisfying Formula 1 include Compounds 1 to 168 below.

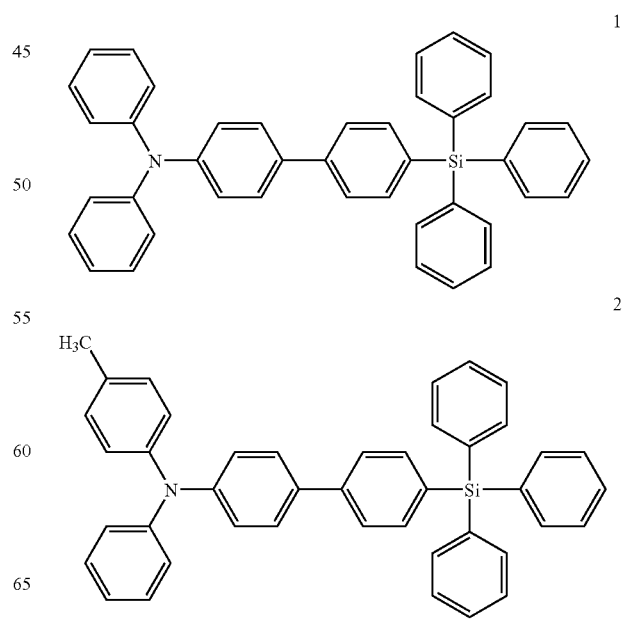

-continued
3
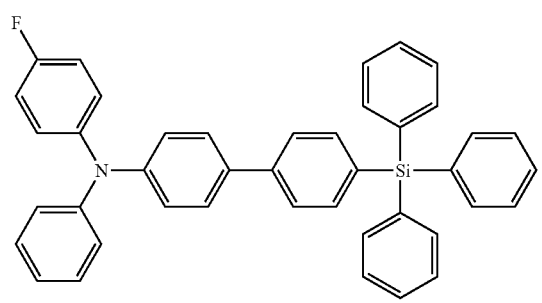
4
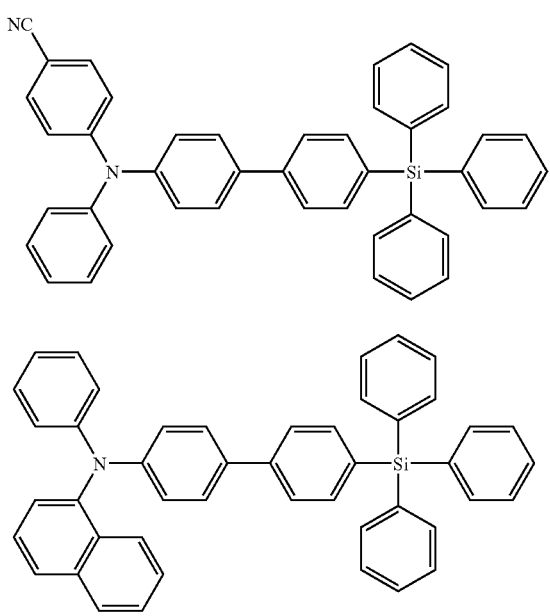
5
6
7
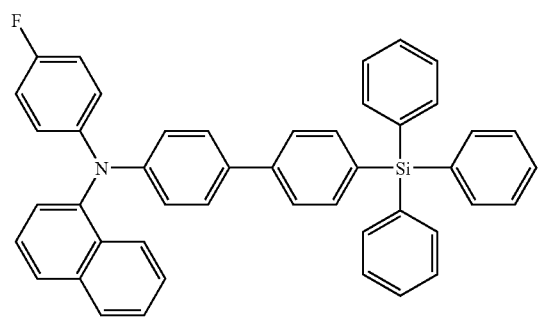
-continued
8
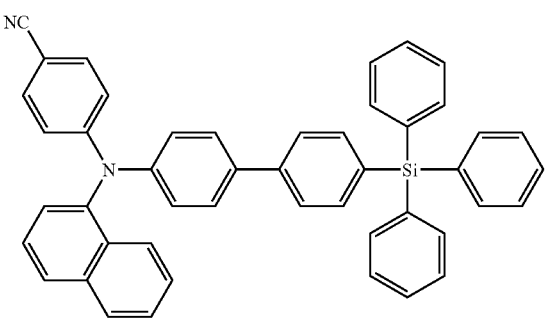
9
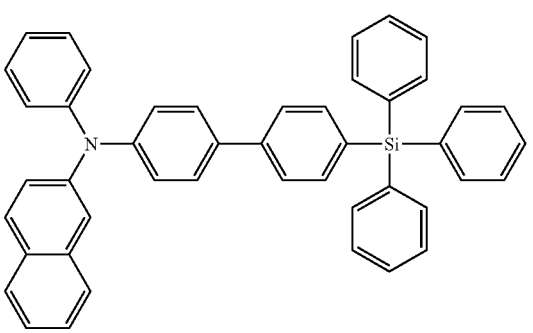
10
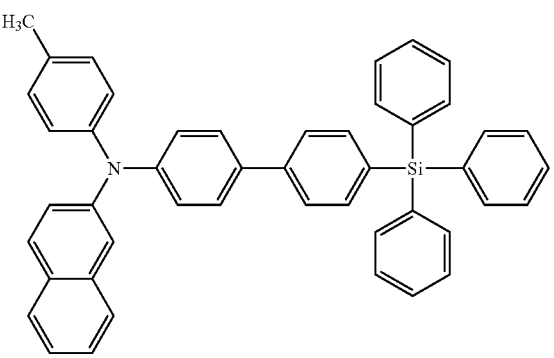
11
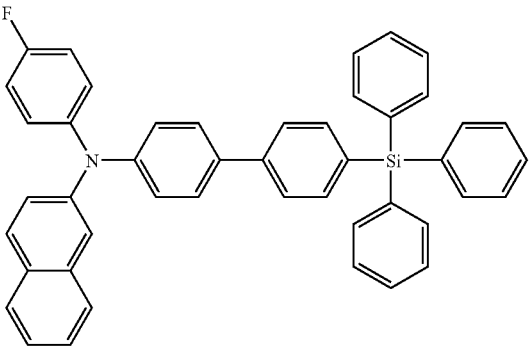

-continued

20
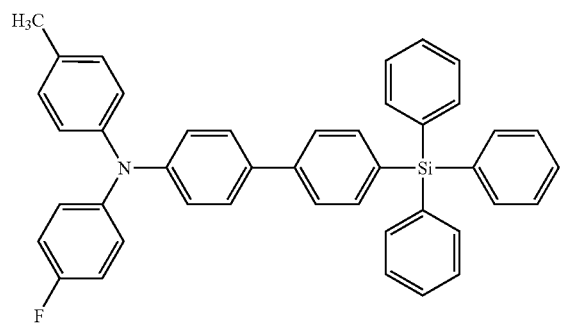
21
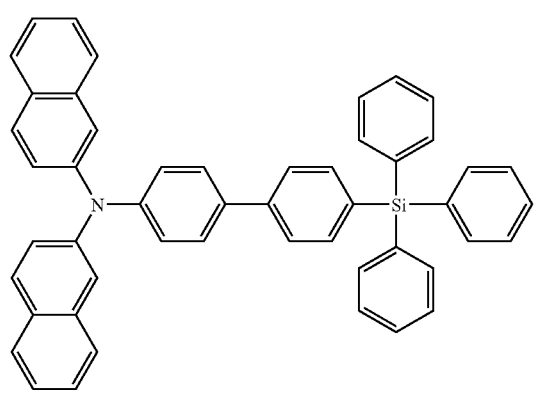
22
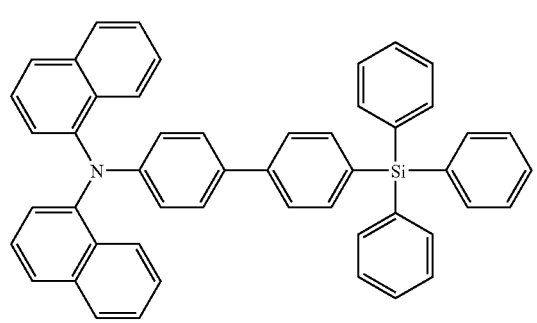
23
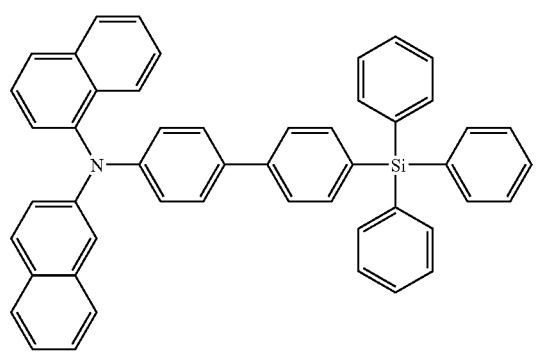
24
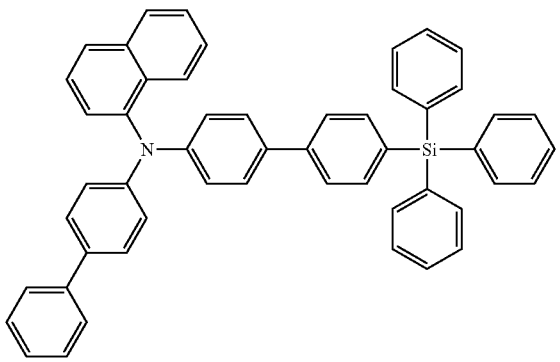
25
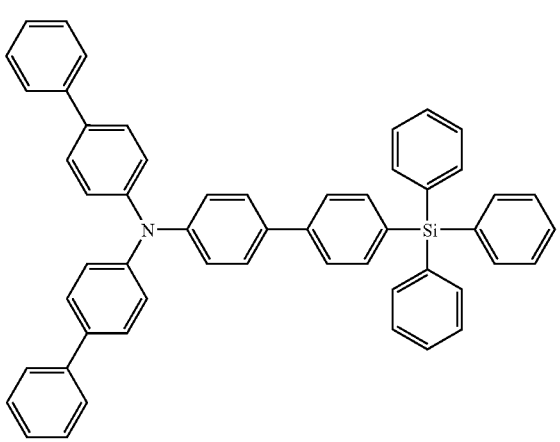
26
27
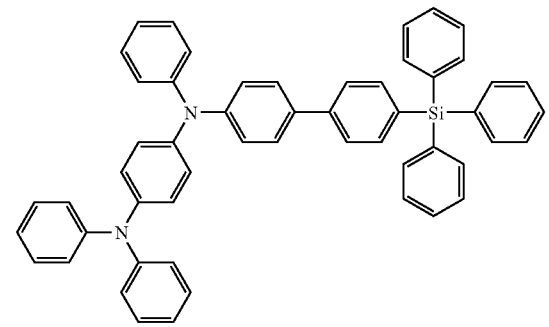

28
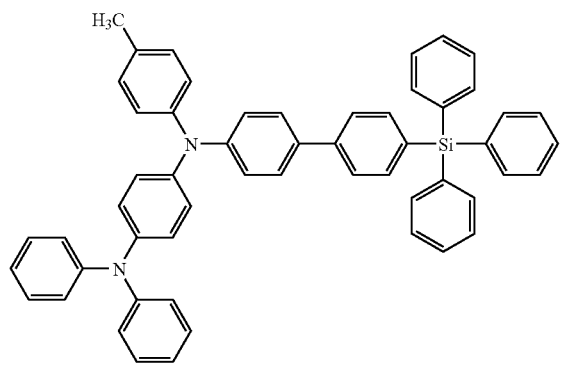
29
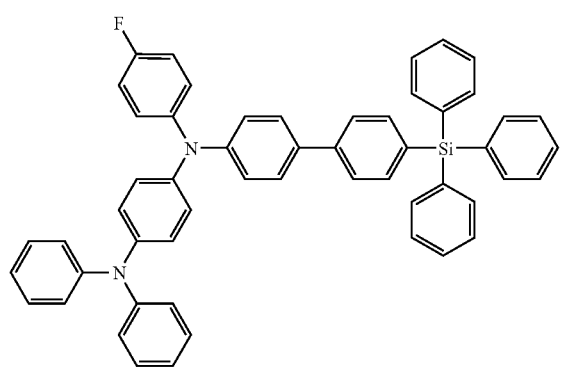
30
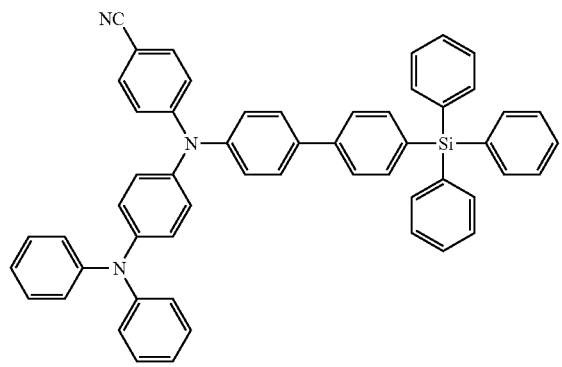
31
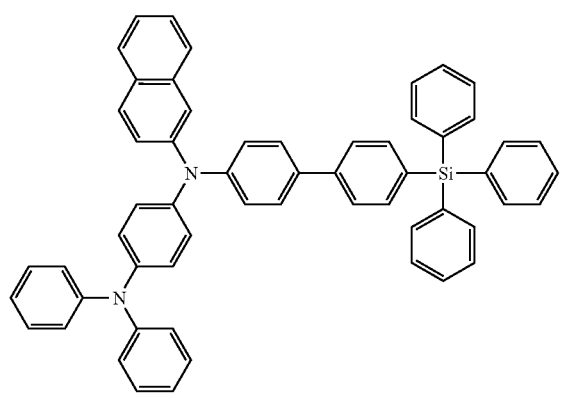
32
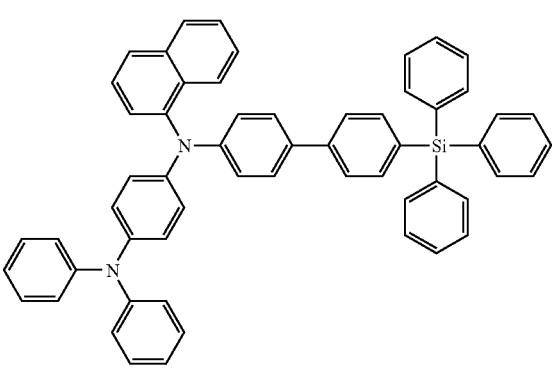
33
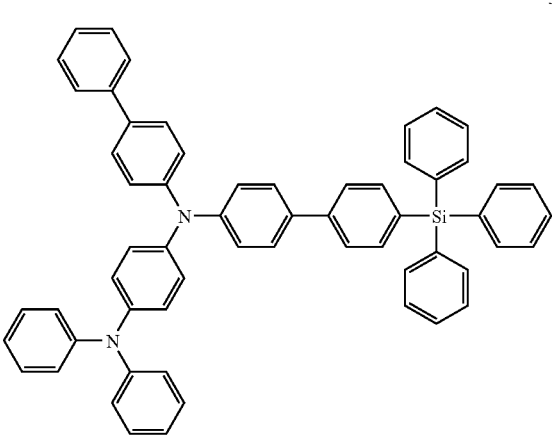
34
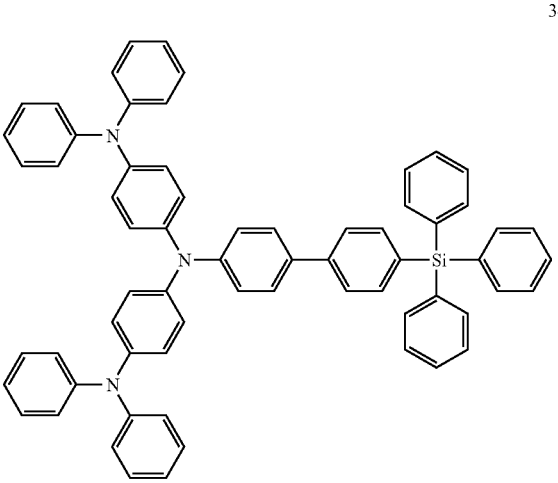
35
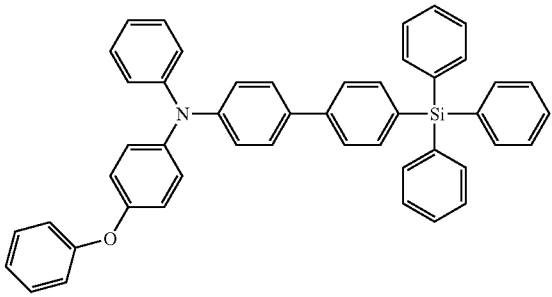

36
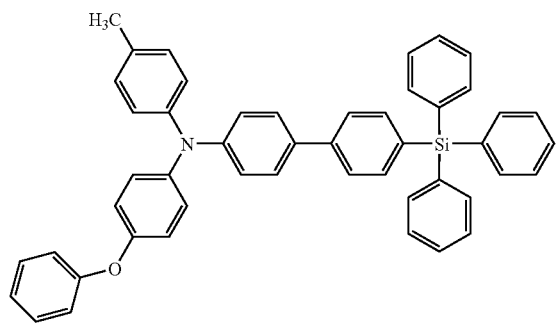
37
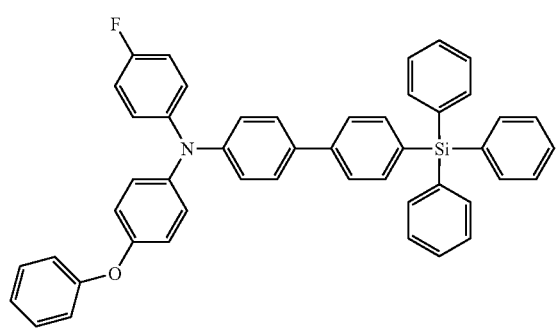
38
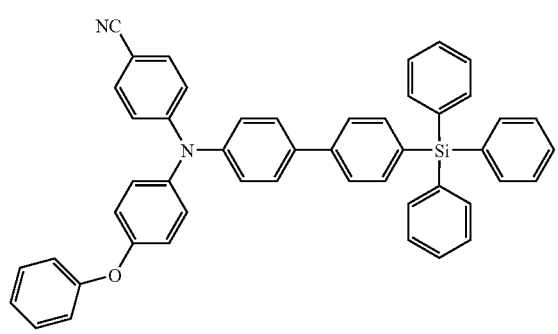
39
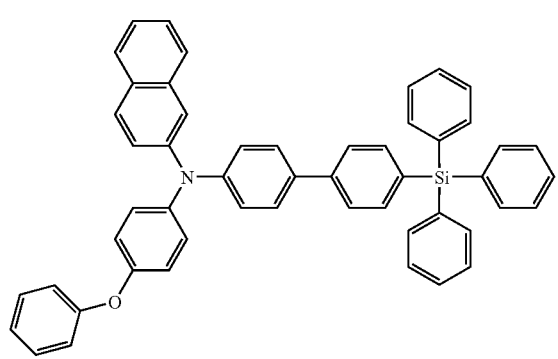
40
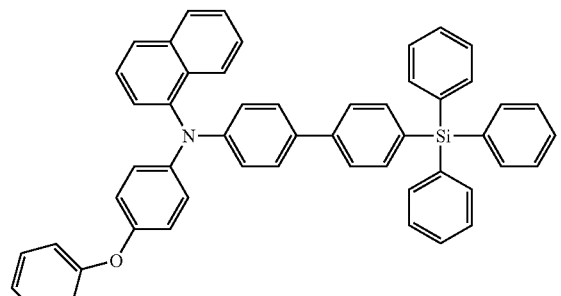
41
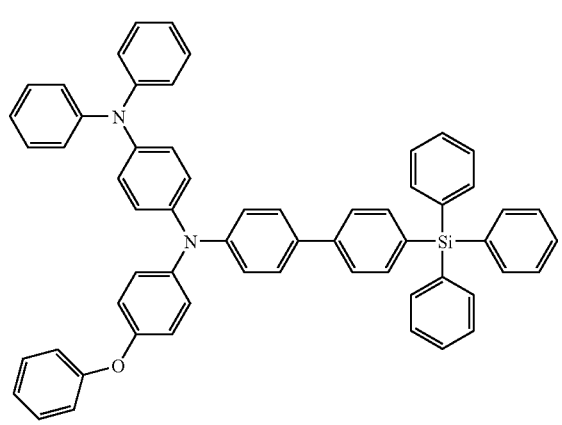
42
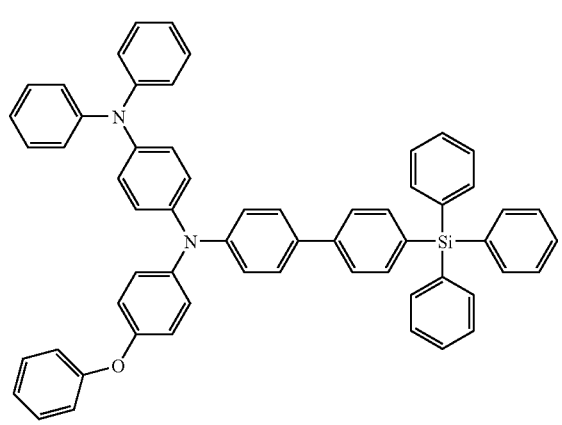
43
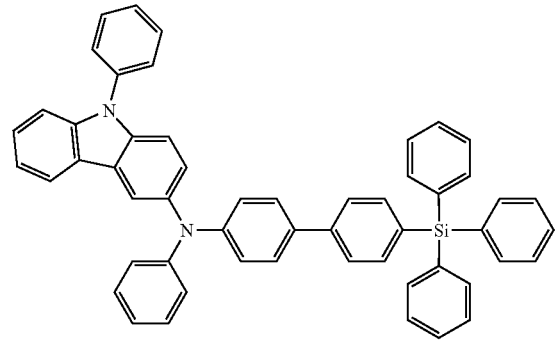

44
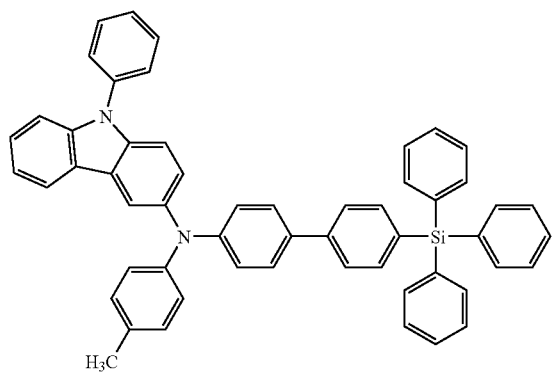
45
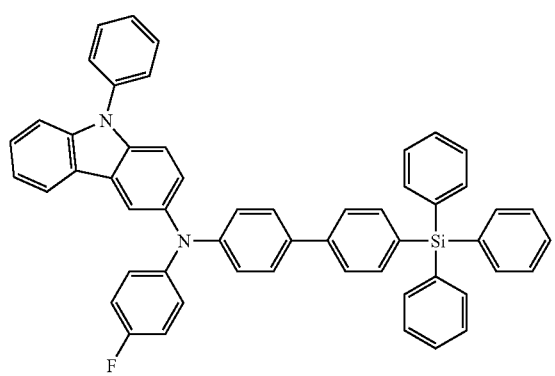
46
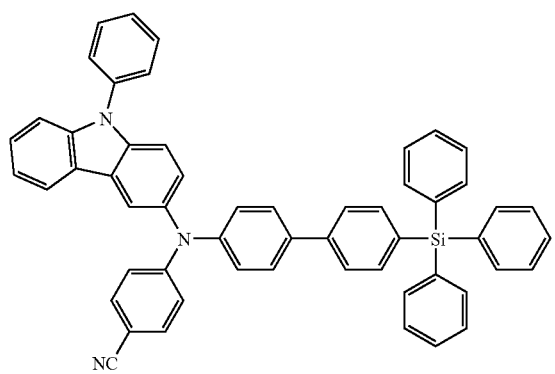
47
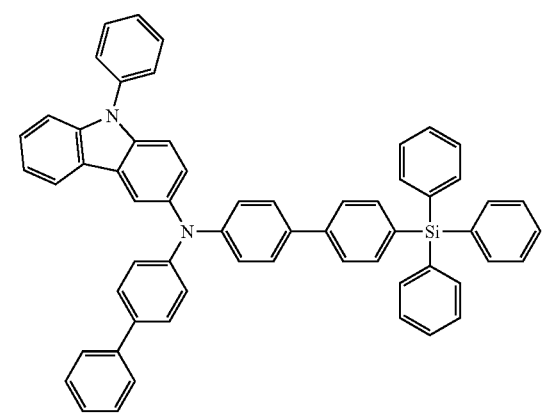
48
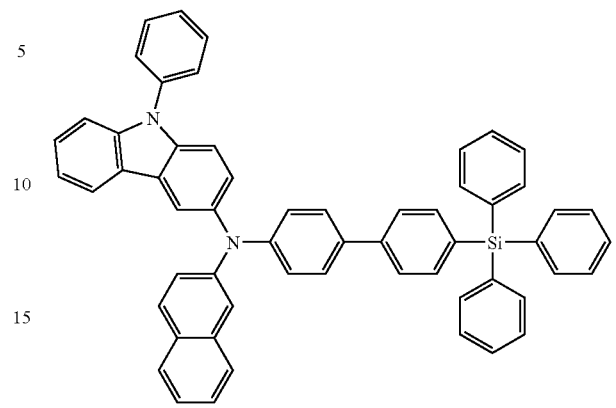
49
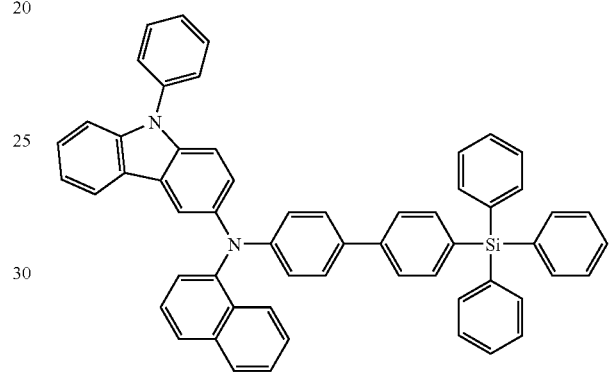
50
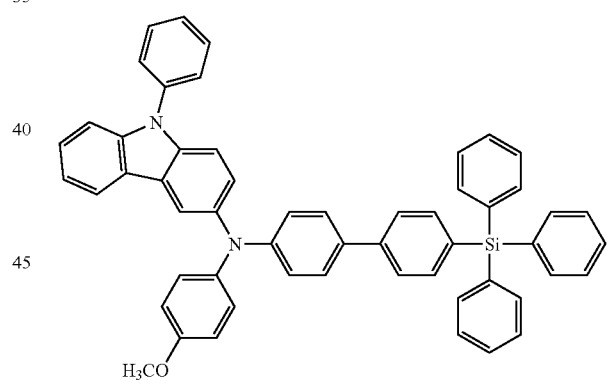
51
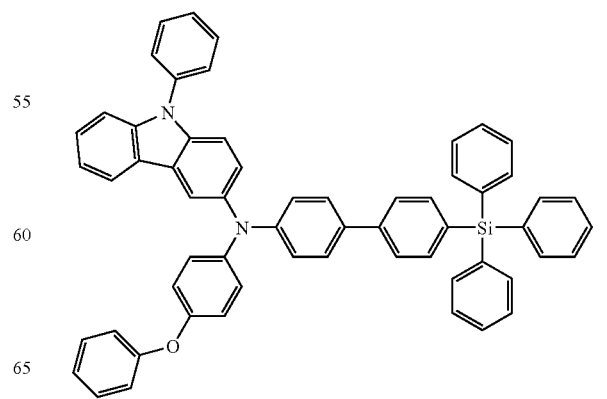

52
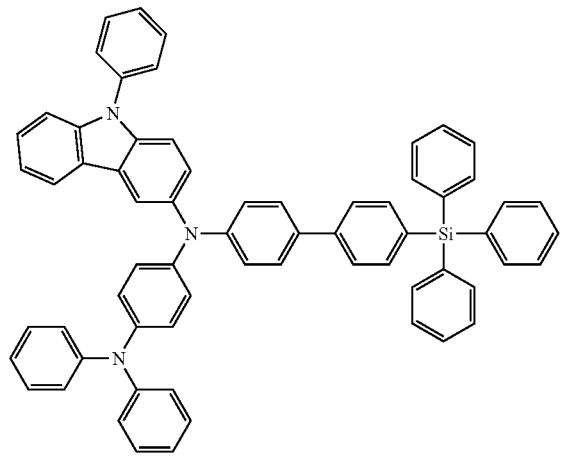
53
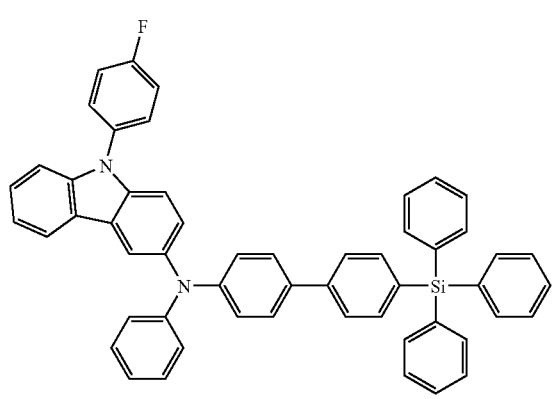
54
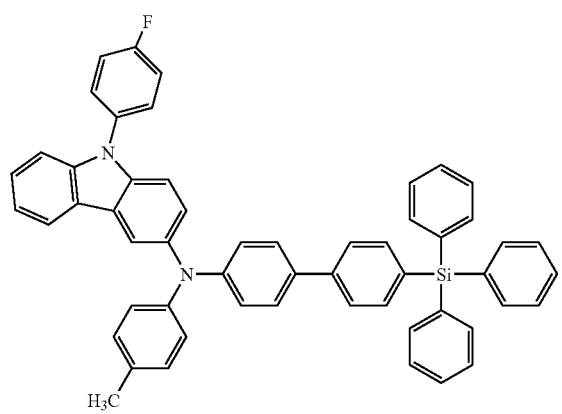
55
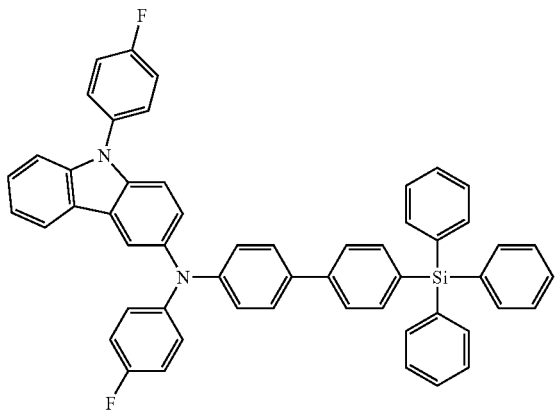
56
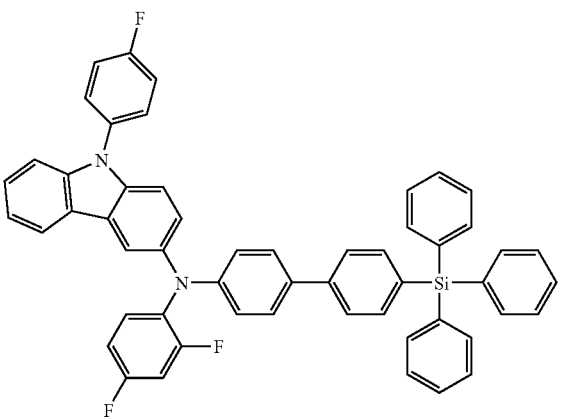
57

58
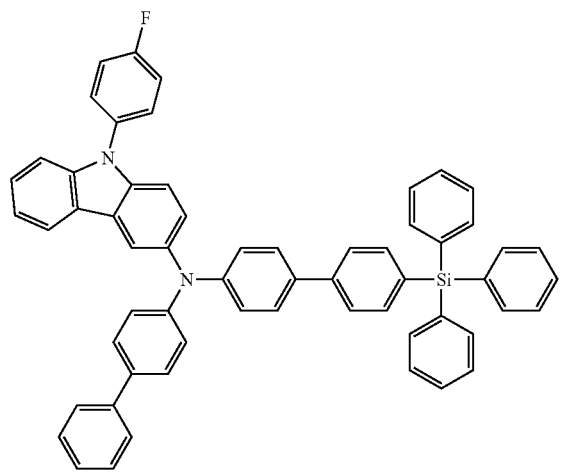
61
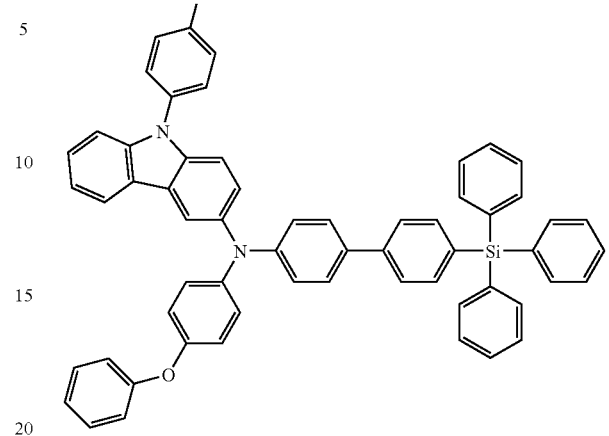
59
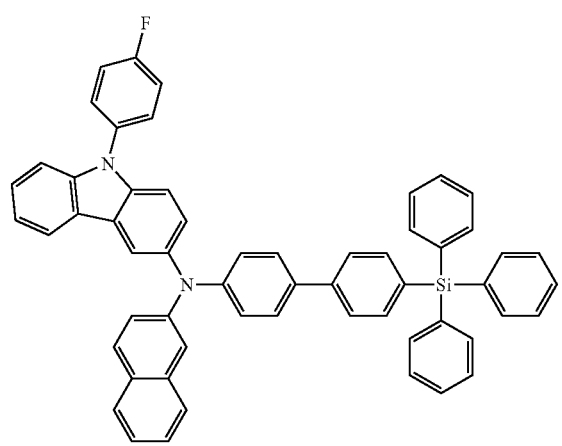
62
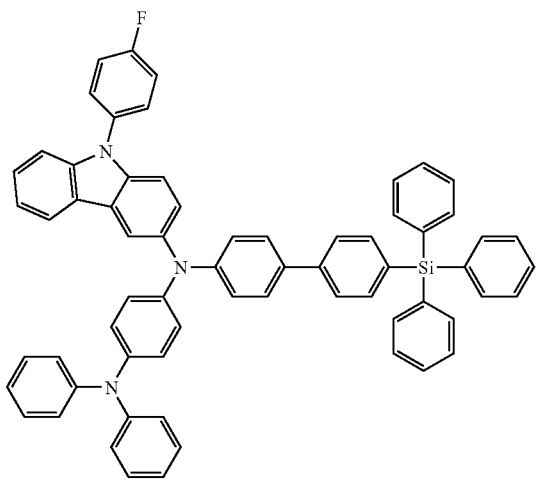
60
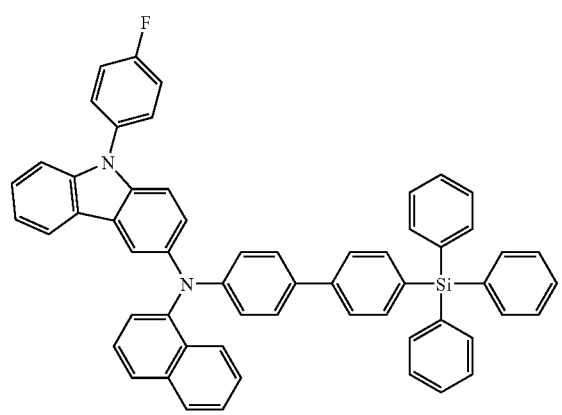
63
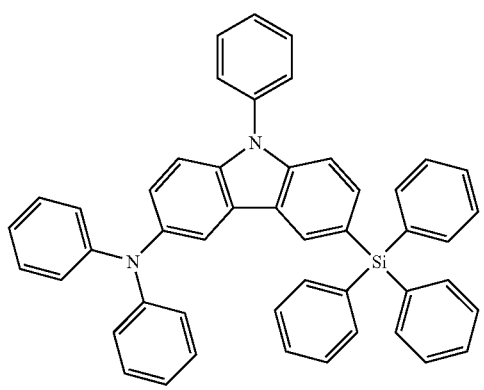

64
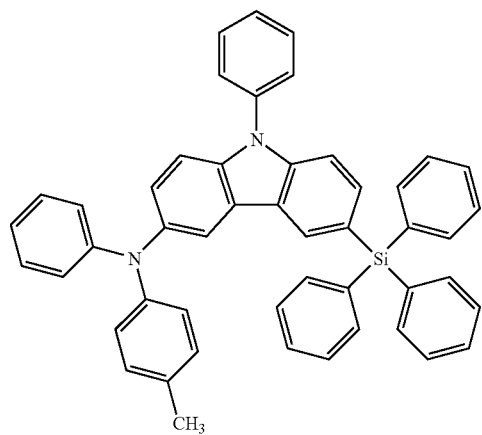
65
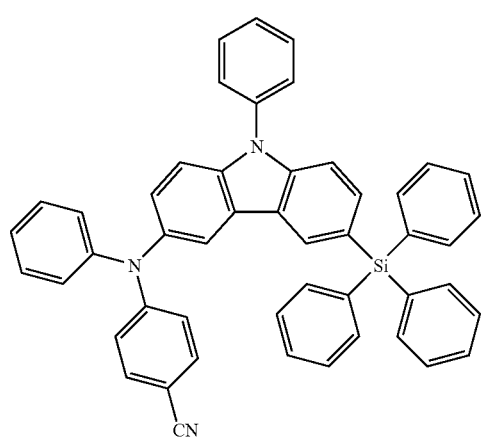
66
67
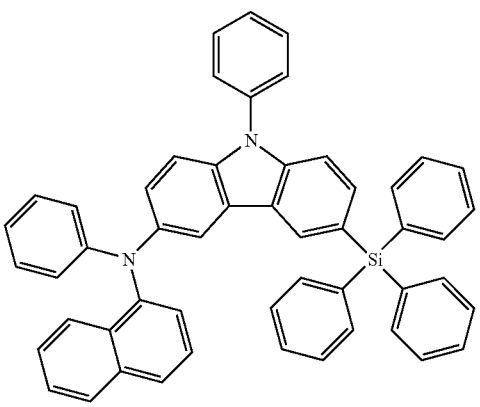
68
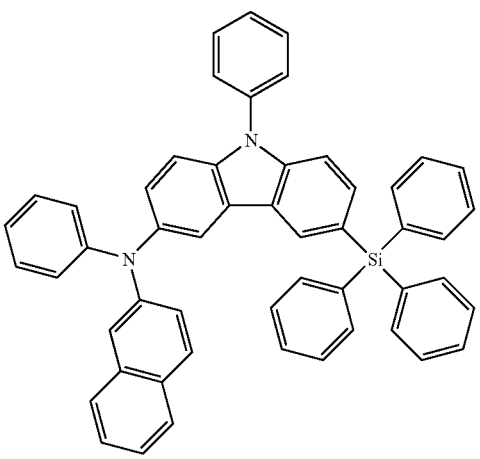
69

70
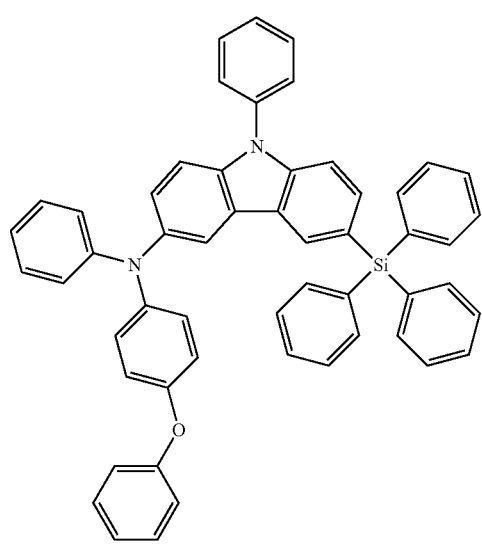
73
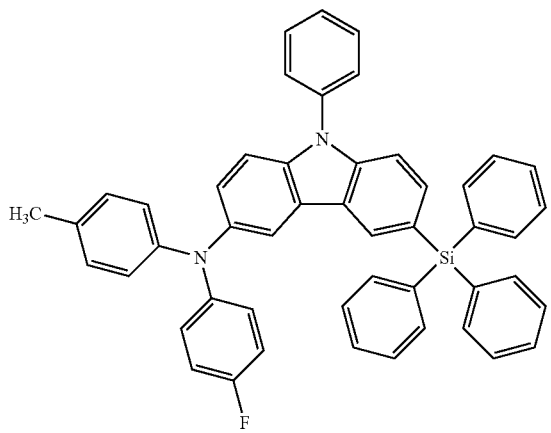
71
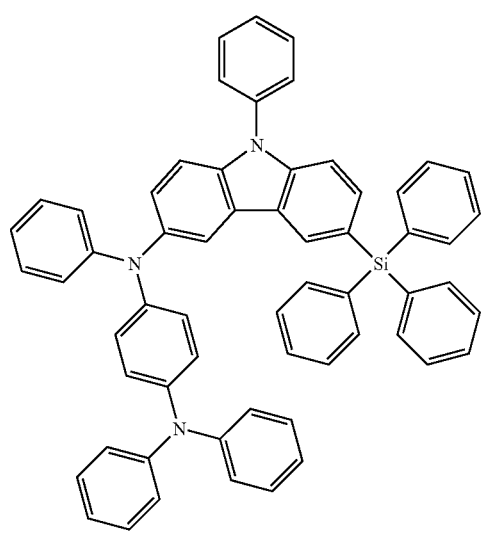
74
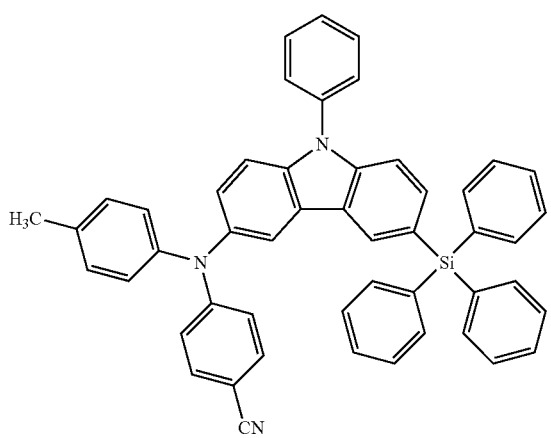
72
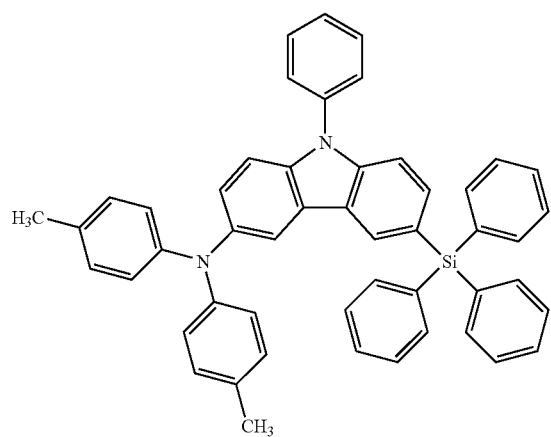
75
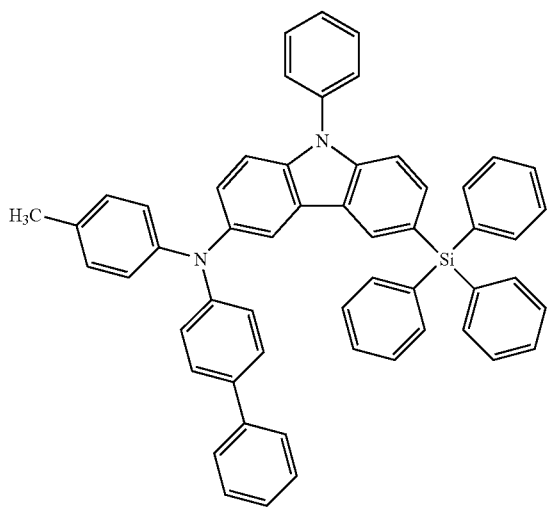

-continued
76
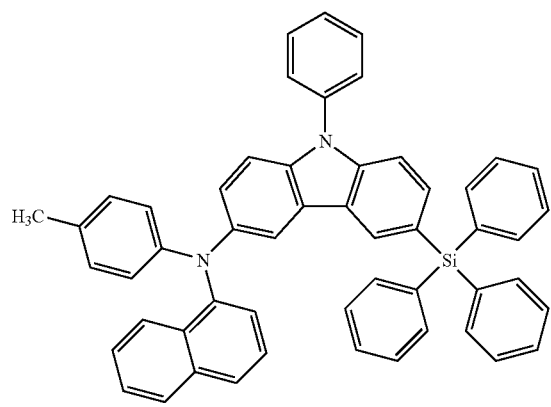
77
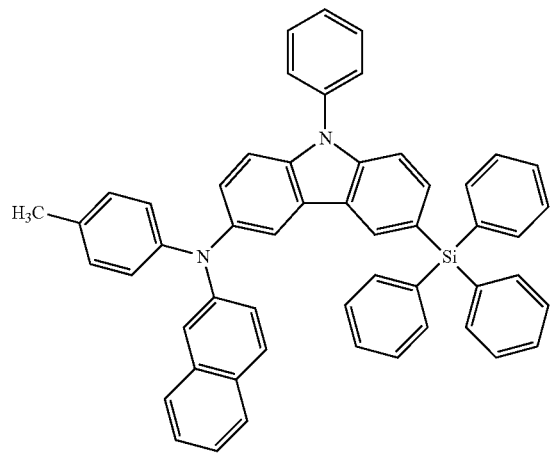
78
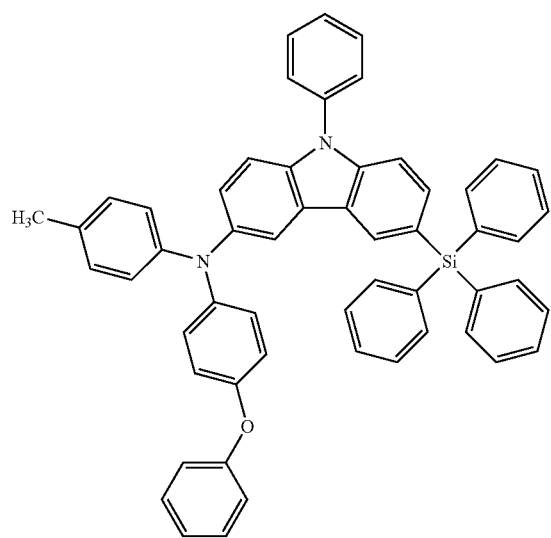
-continued
79
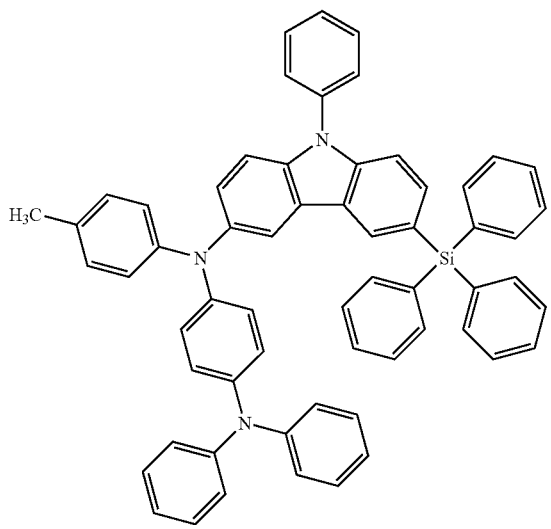
80
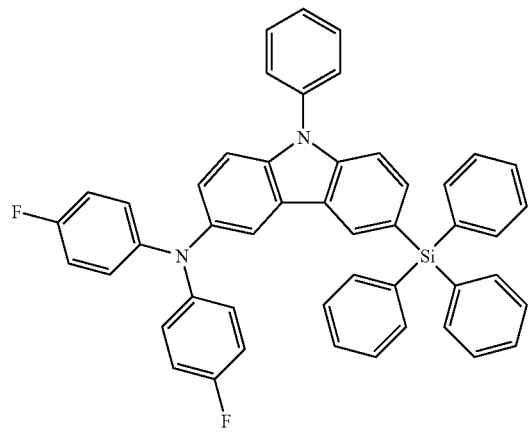
81
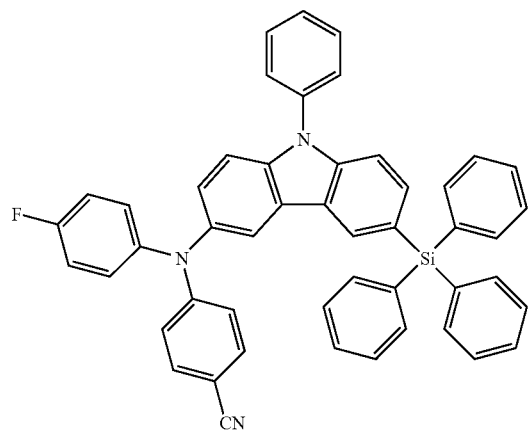

82
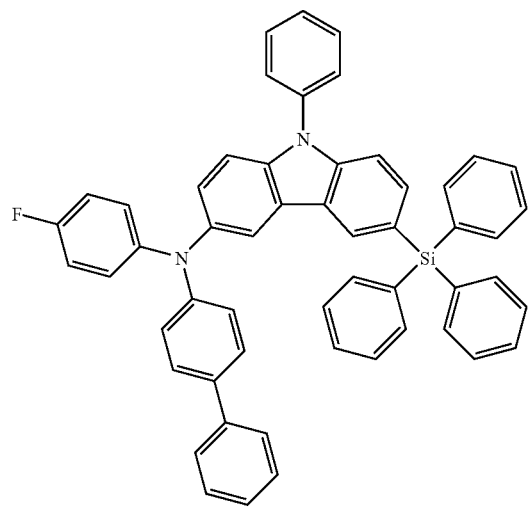
83
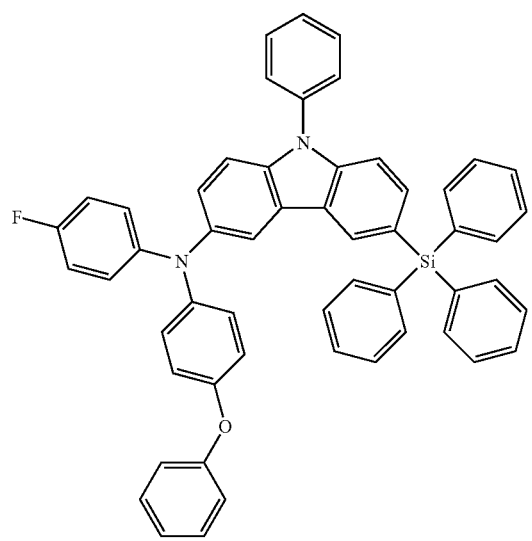
84
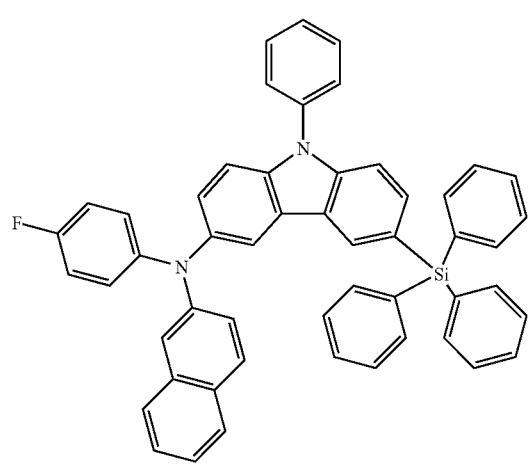
85
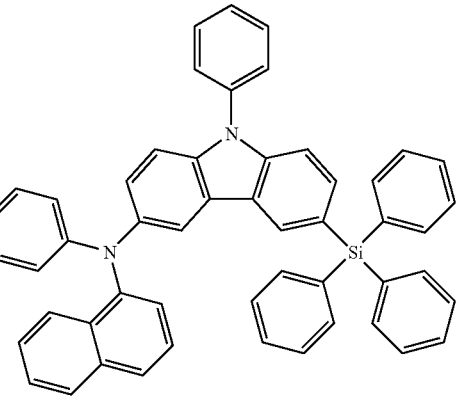
86
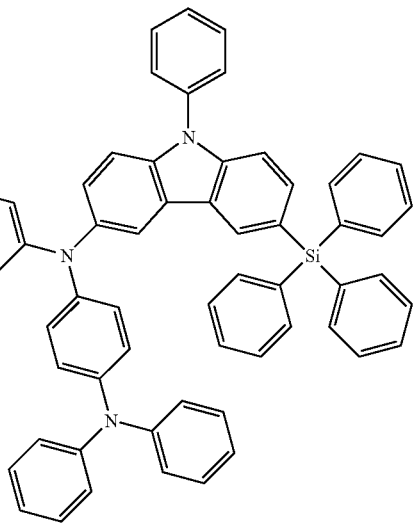
87
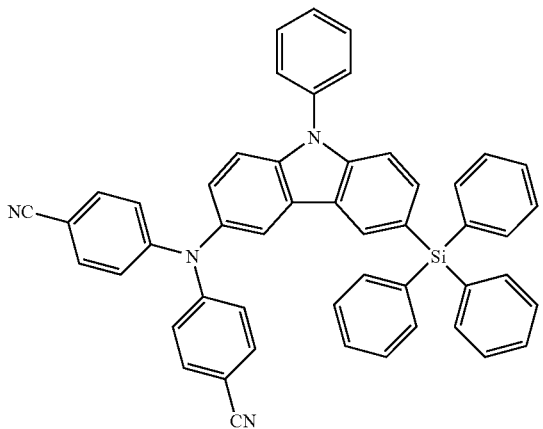

88
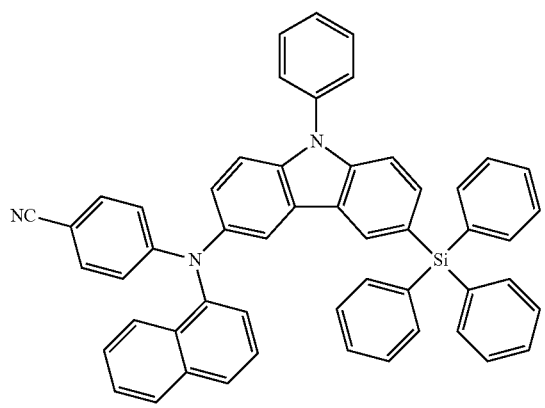
89
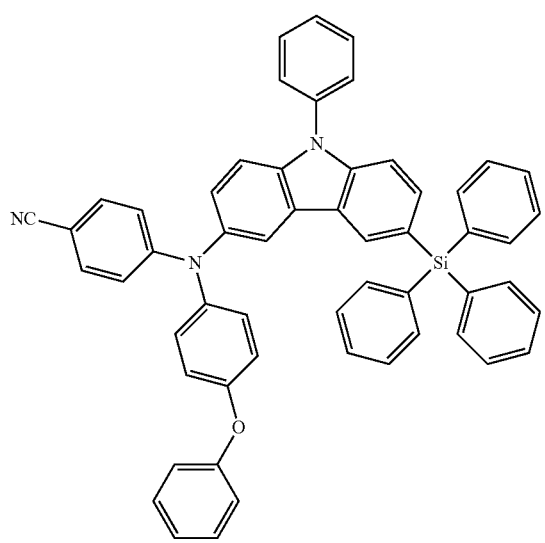
90
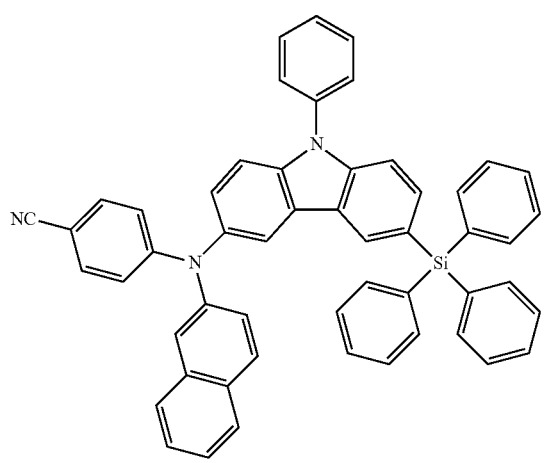
91
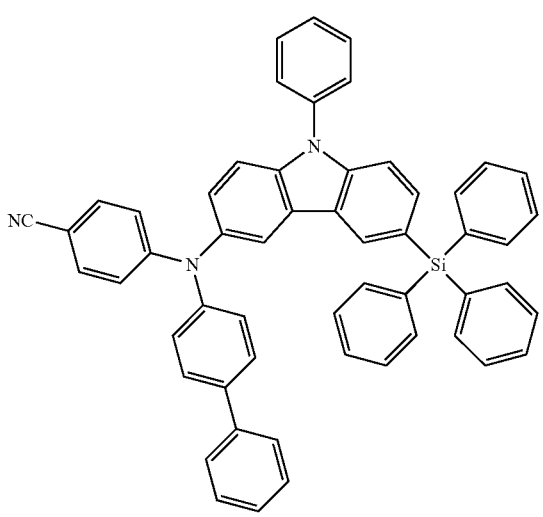
92
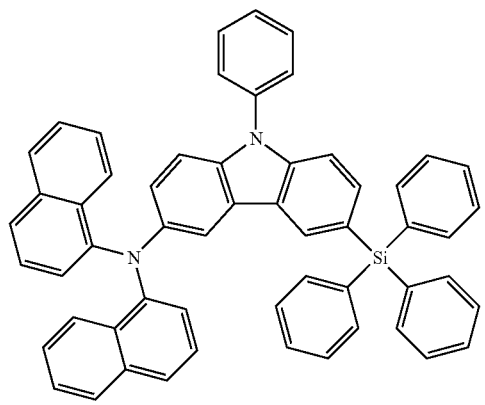
93
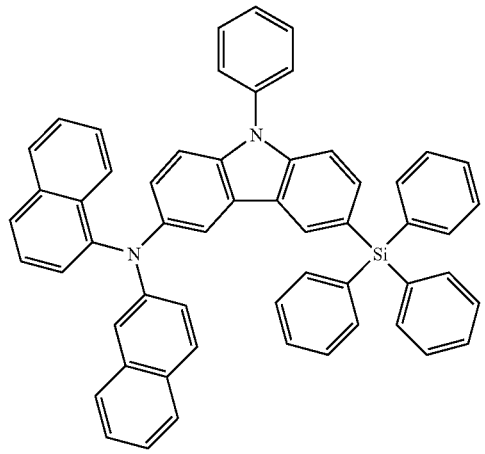

94
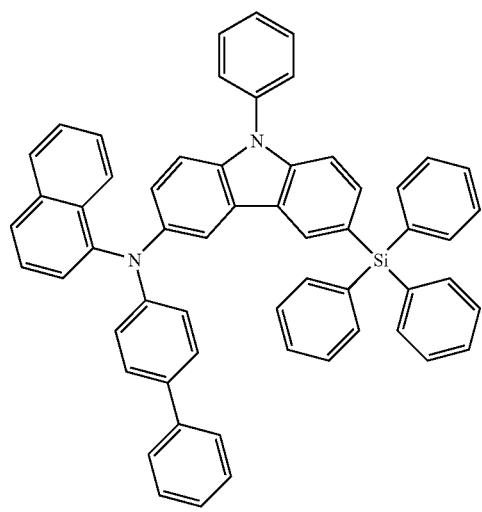
95
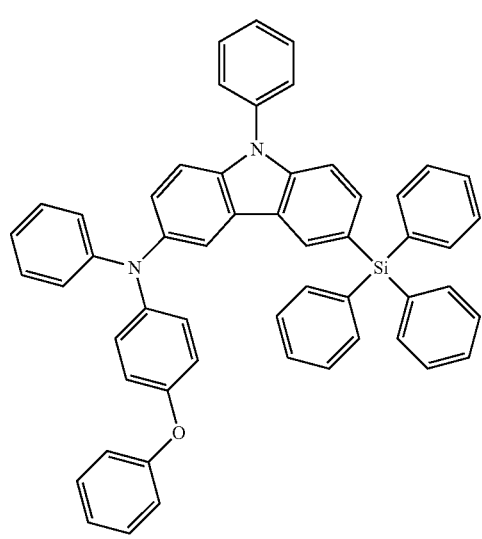
96
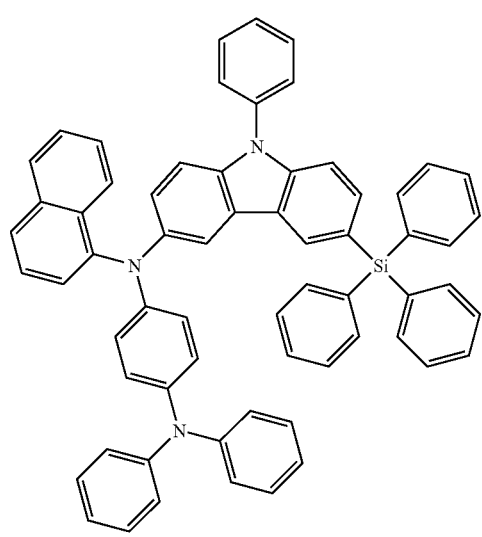
97
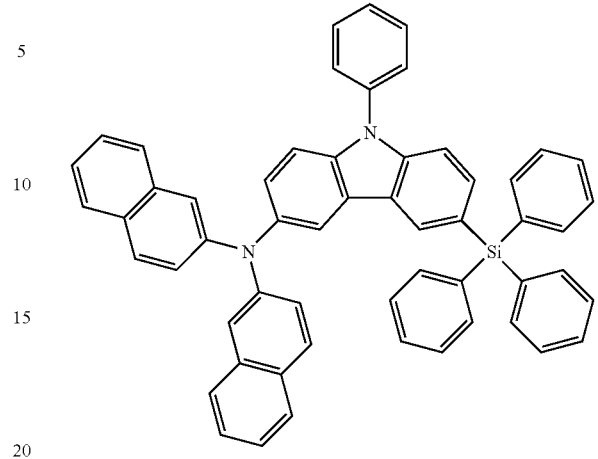
98
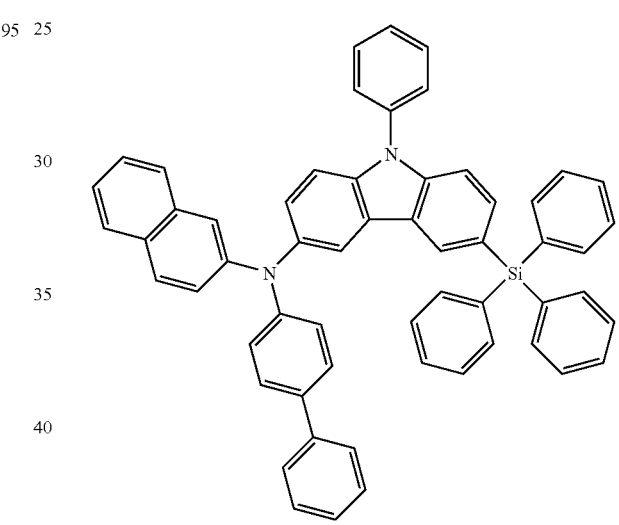
99

100
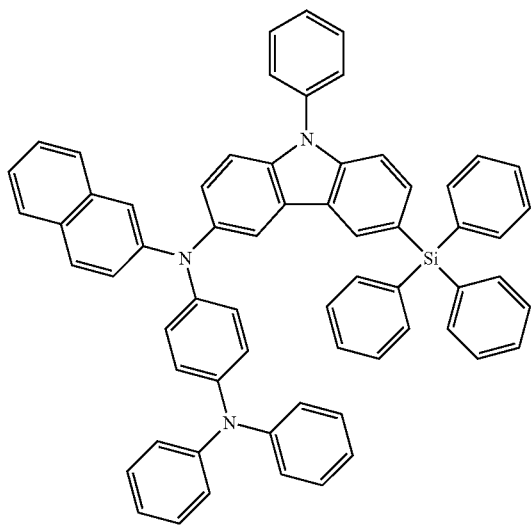
101
103
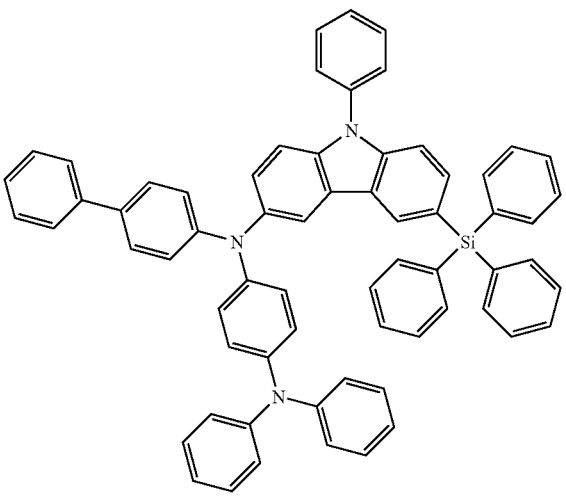
104
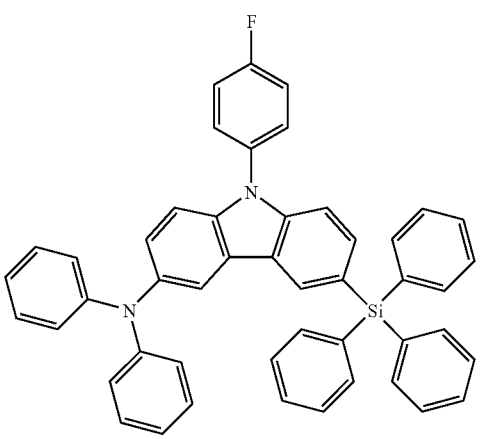
102
105
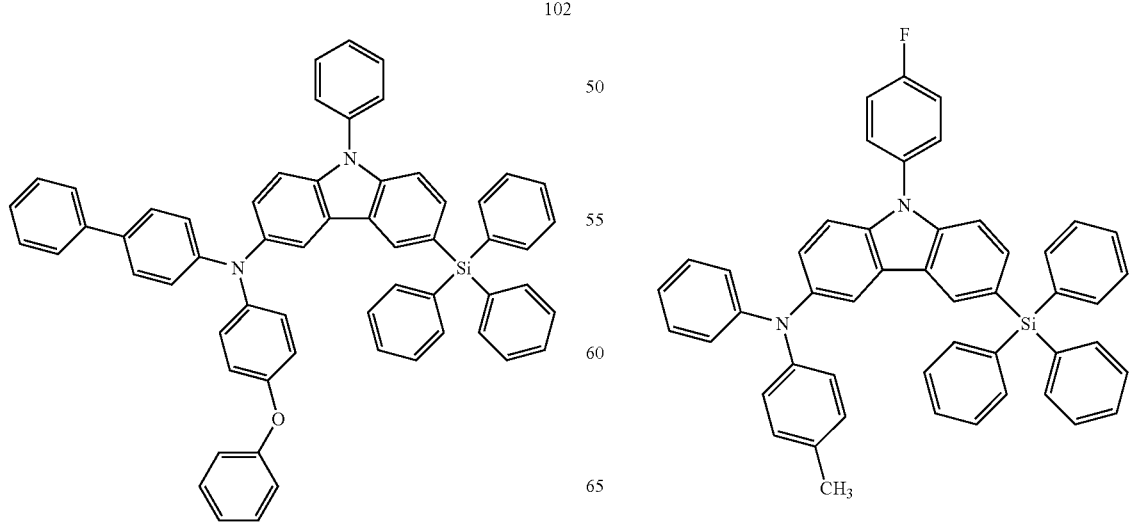

106
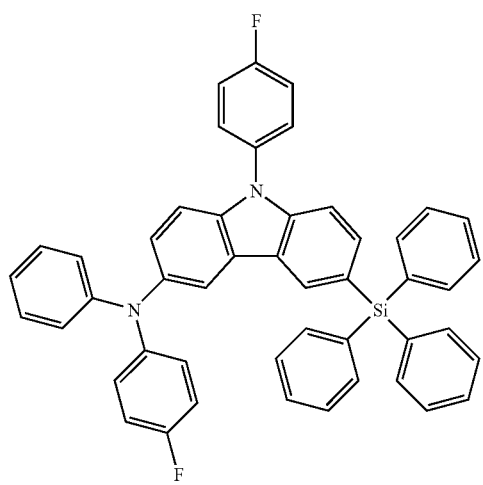
107
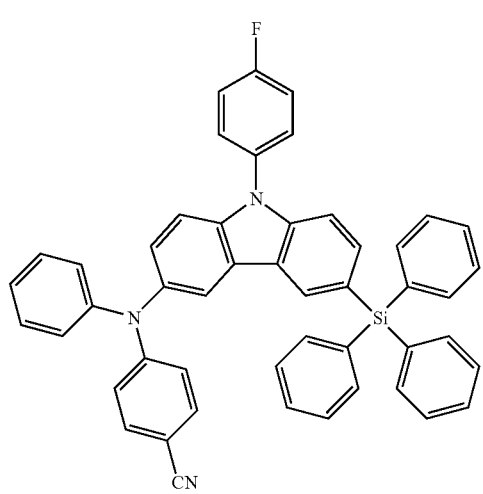
109
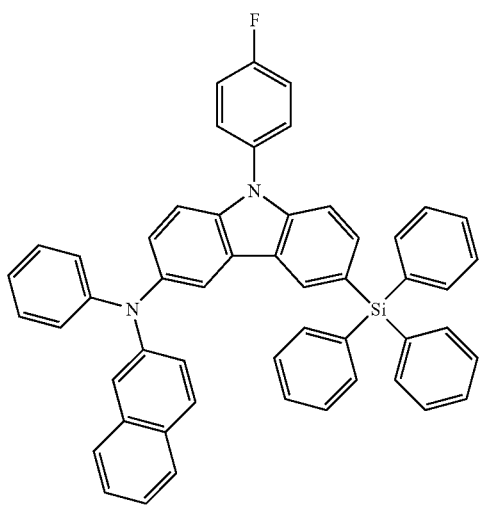
110
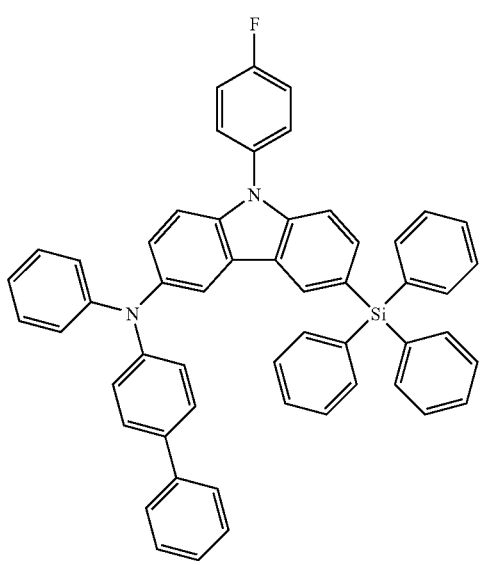
111
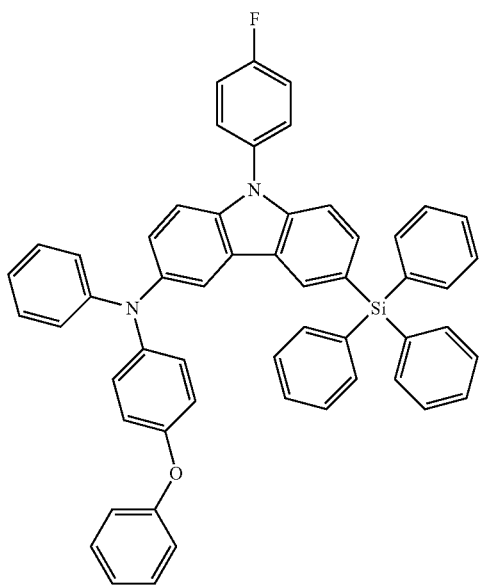

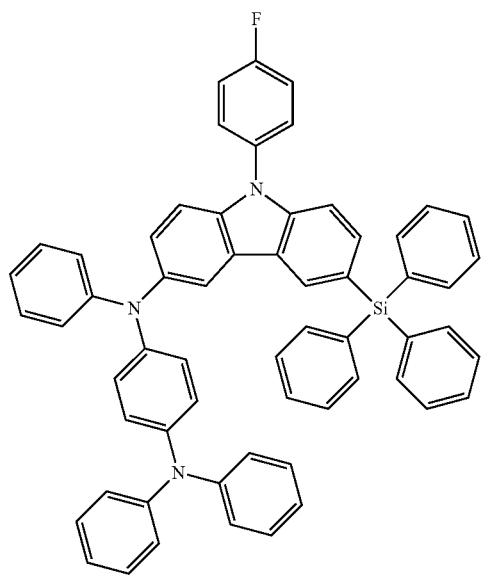
112
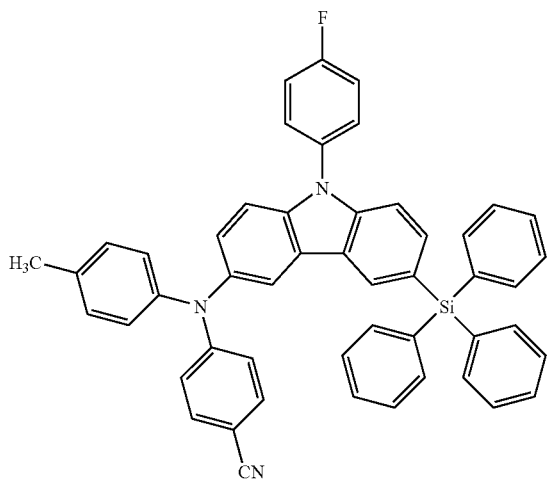
115
113
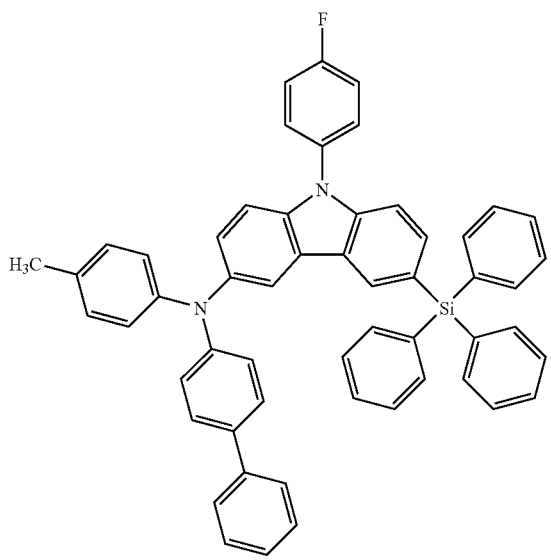
116
114
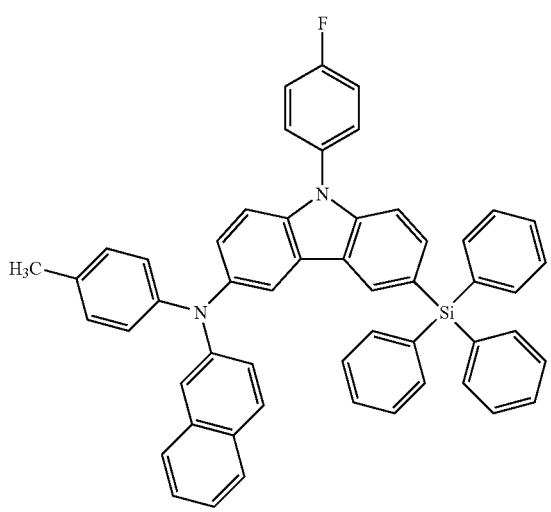
117

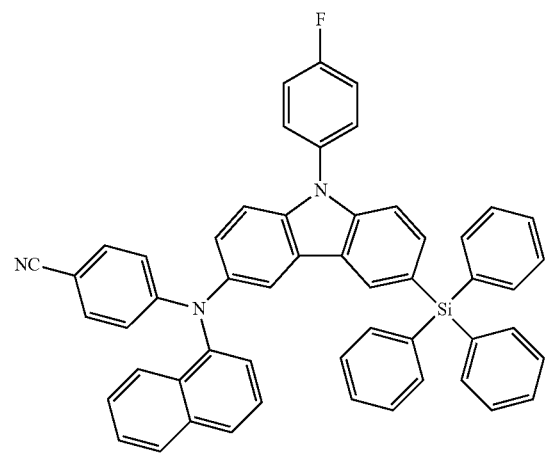
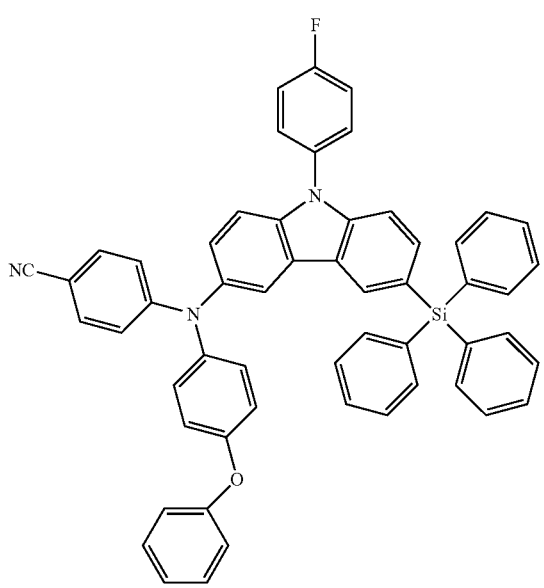
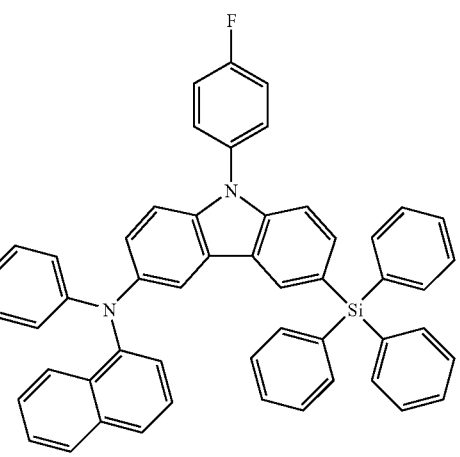
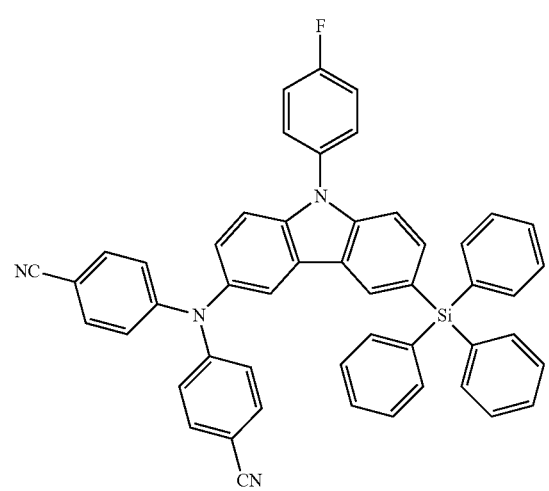

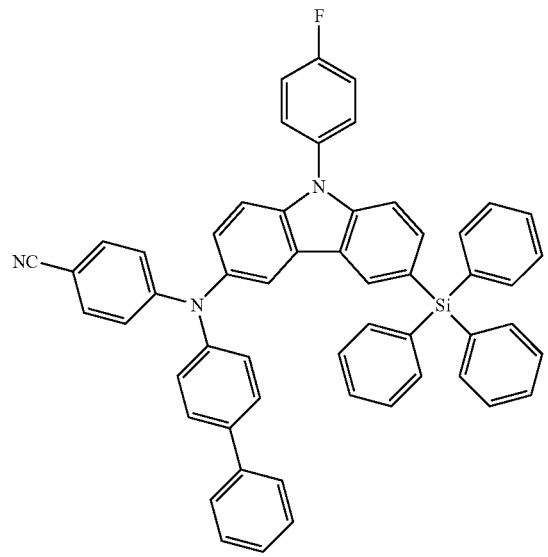
124
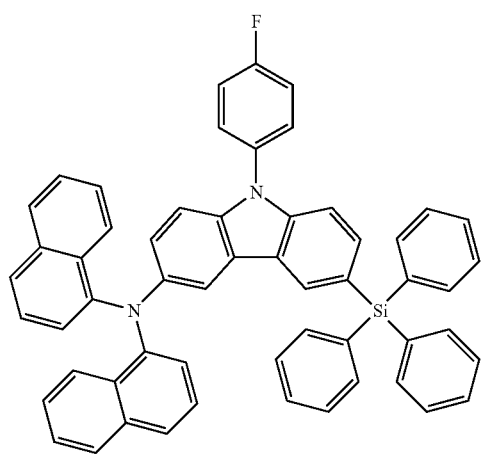
125
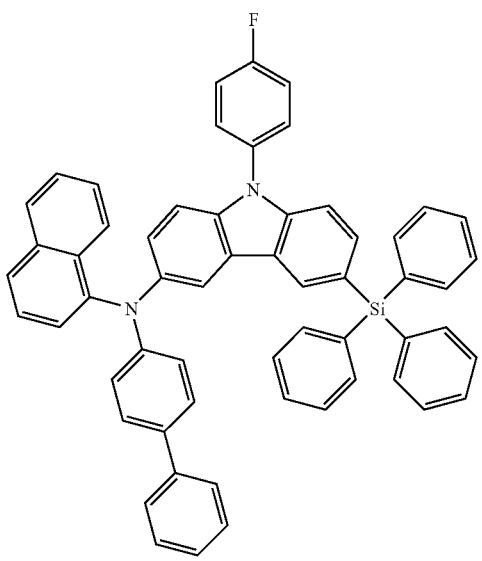
127
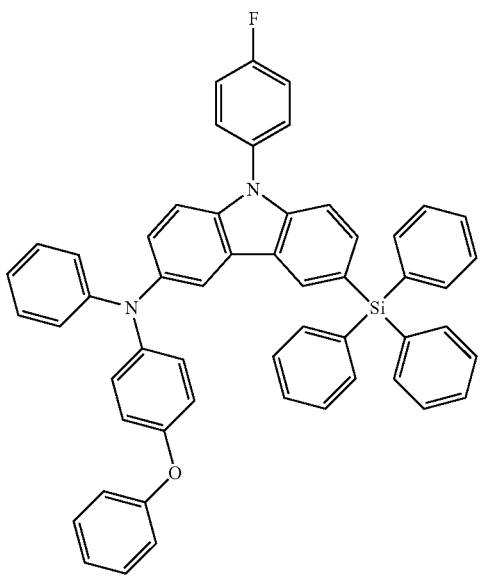
128

129
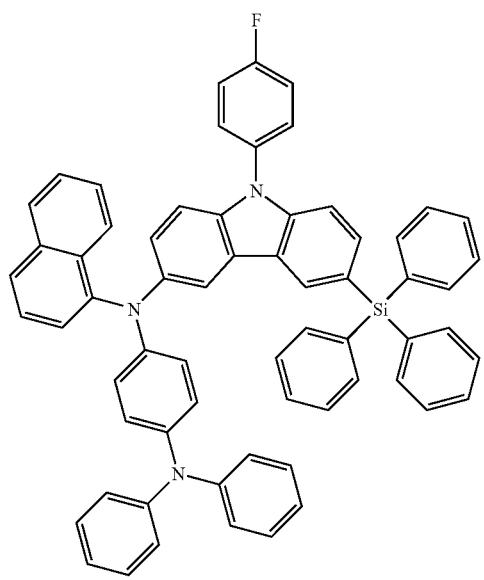
130
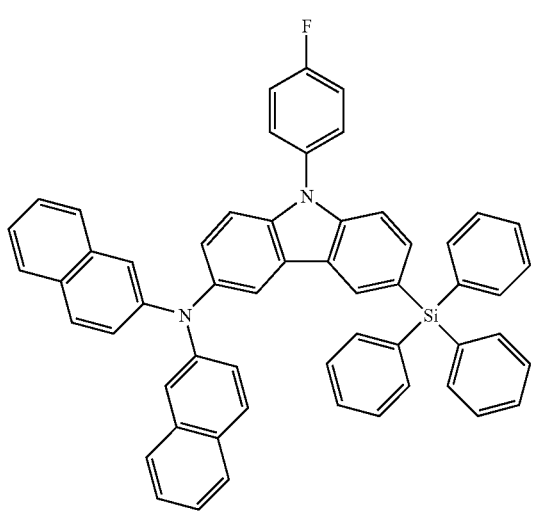
131
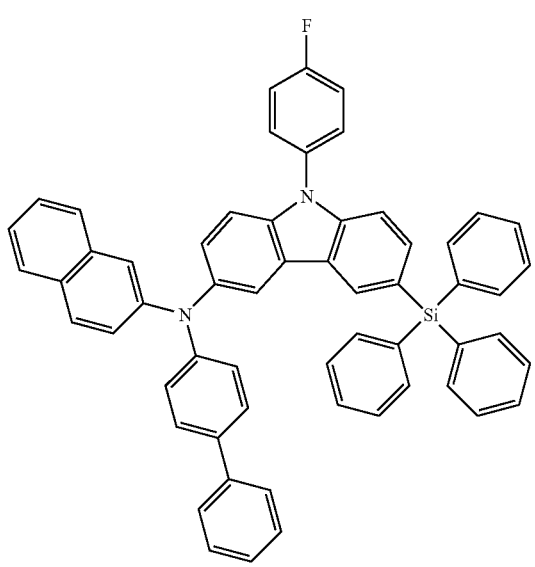
132
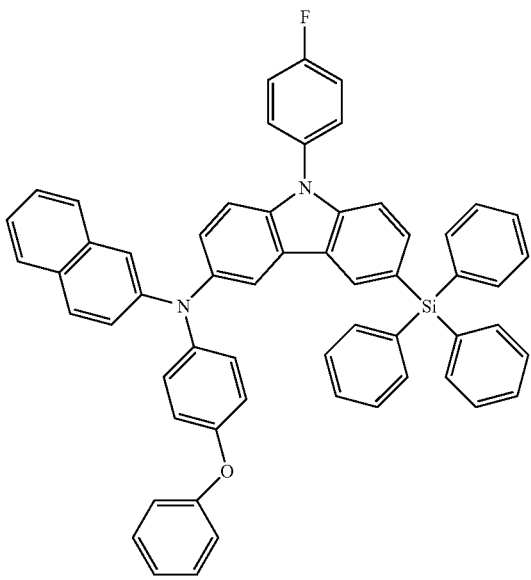
133
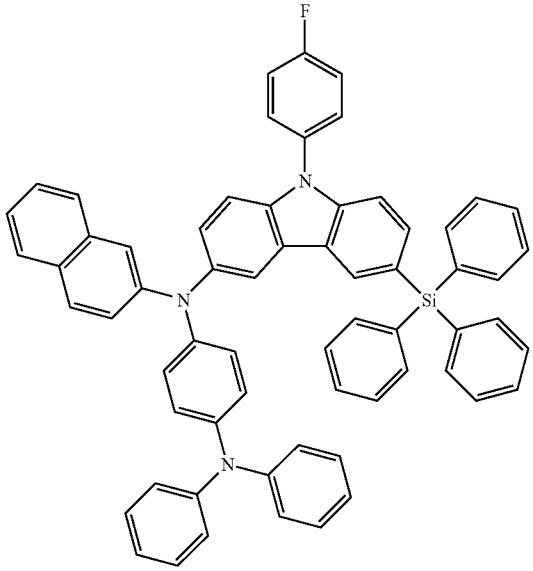

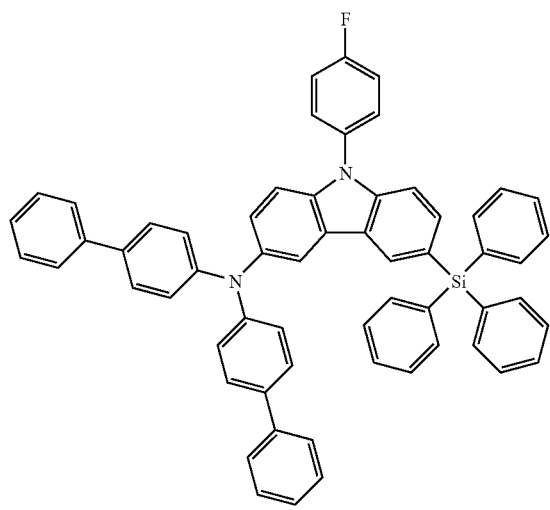
134
135
136
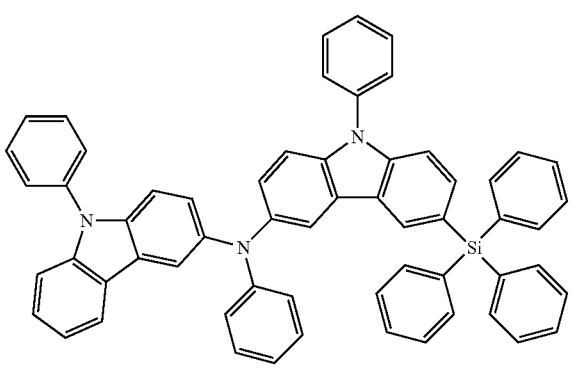
137
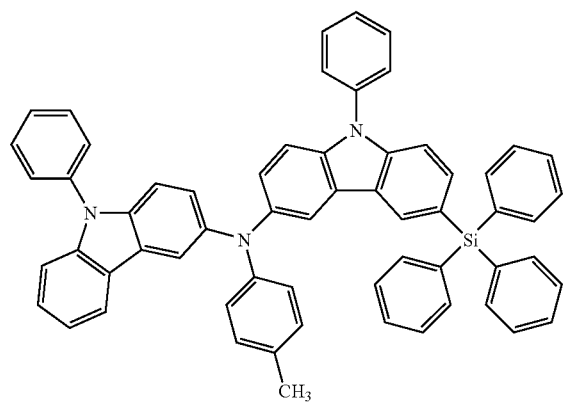
138
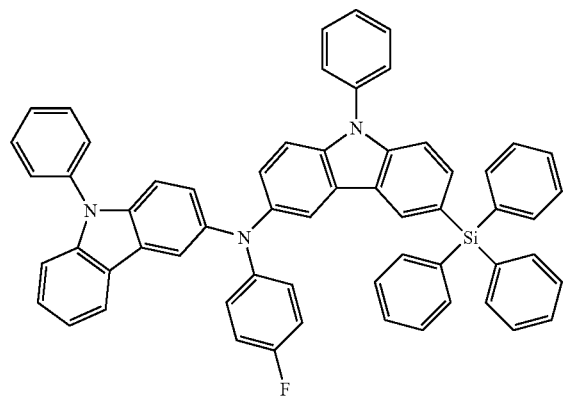
139
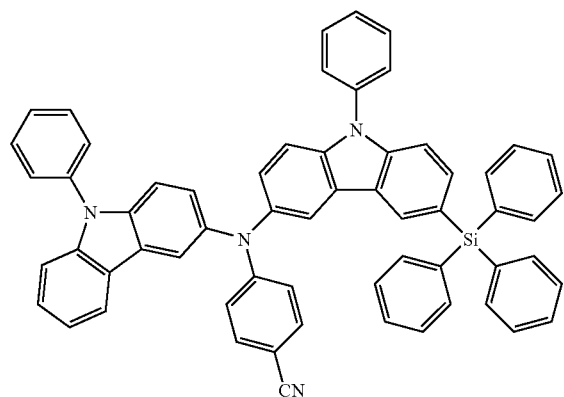
140

141
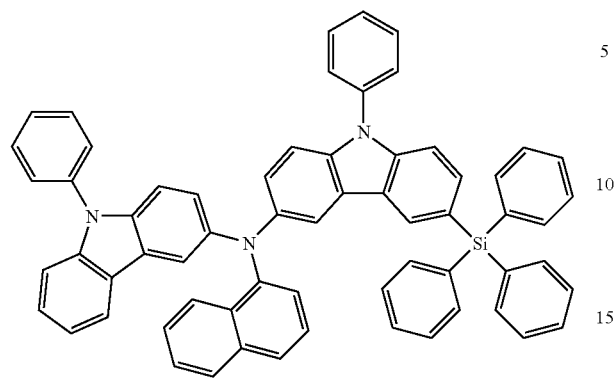
142
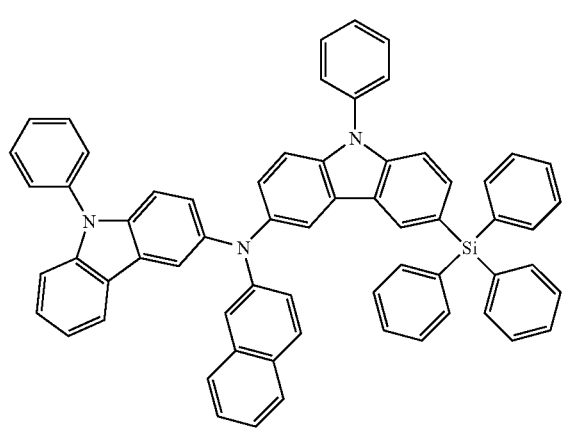
143
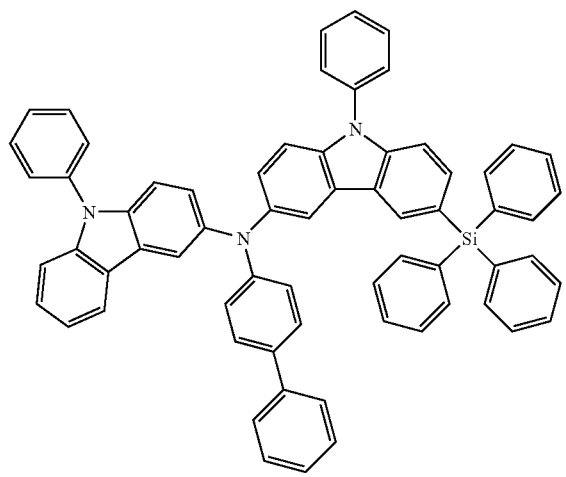
144
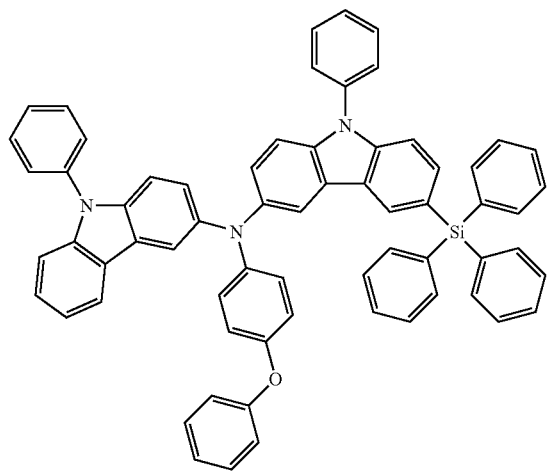
145
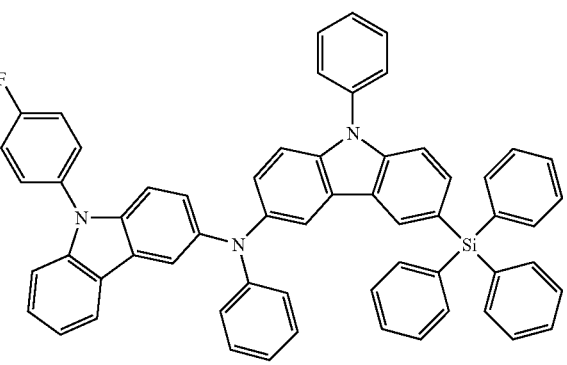
146
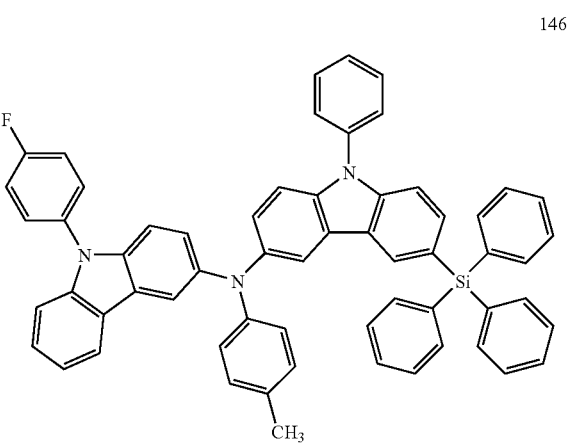

147
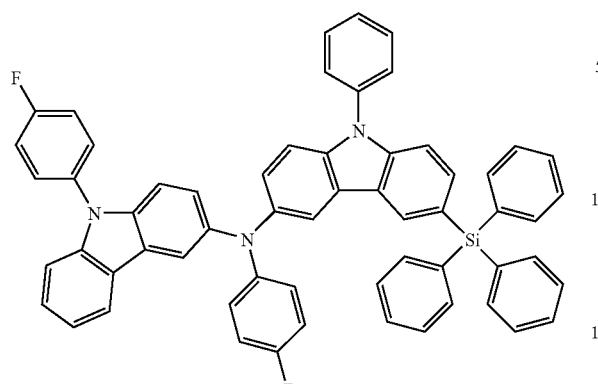
148
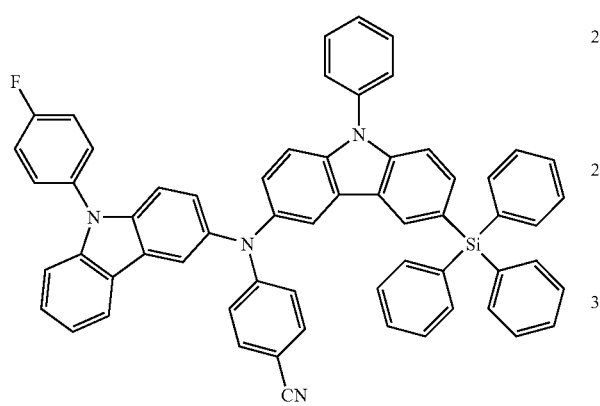
149
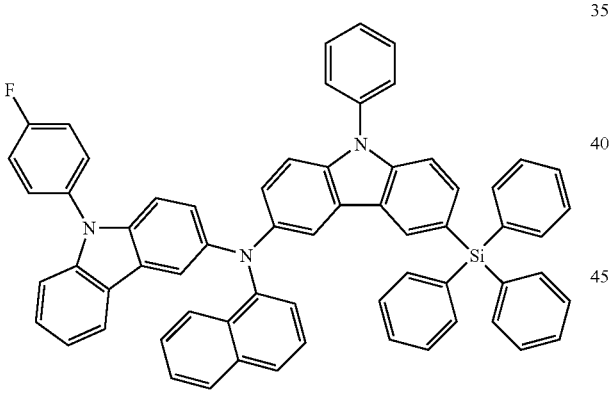
150
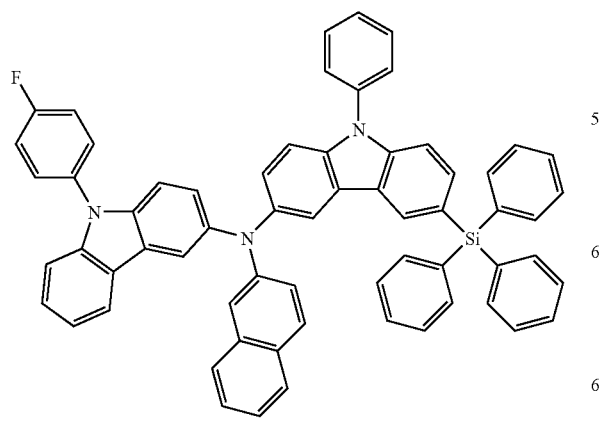
151
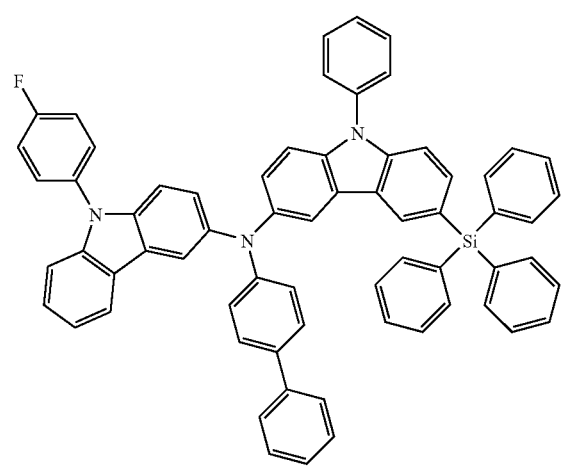
152
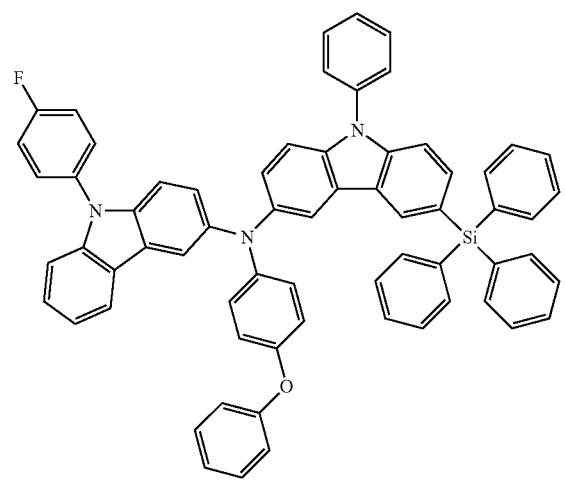
153
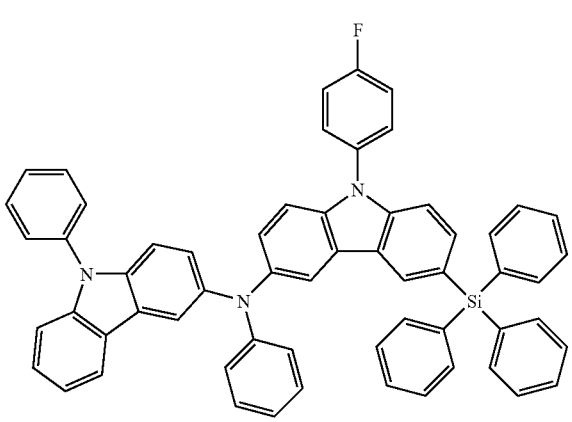

154
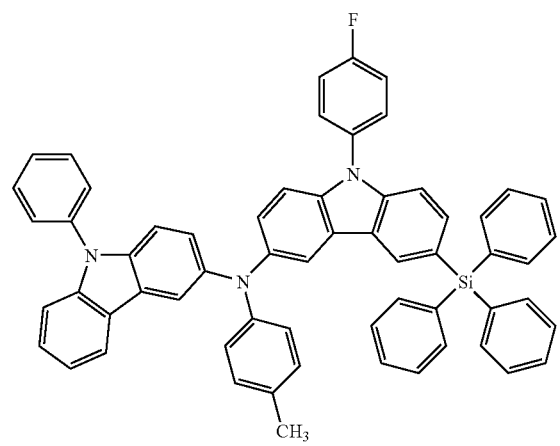
157
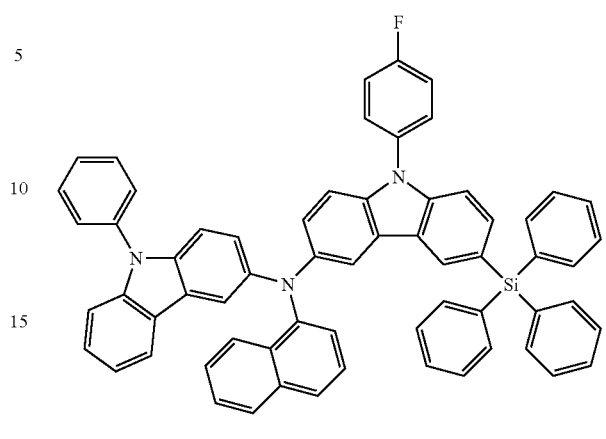
155
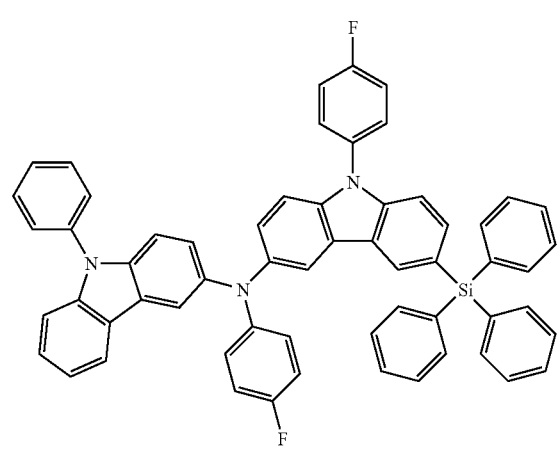
158
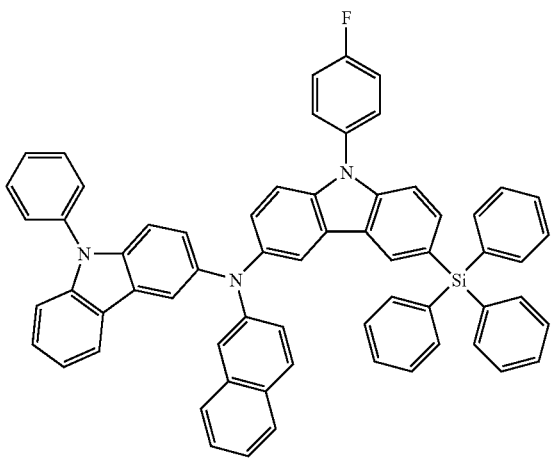
156
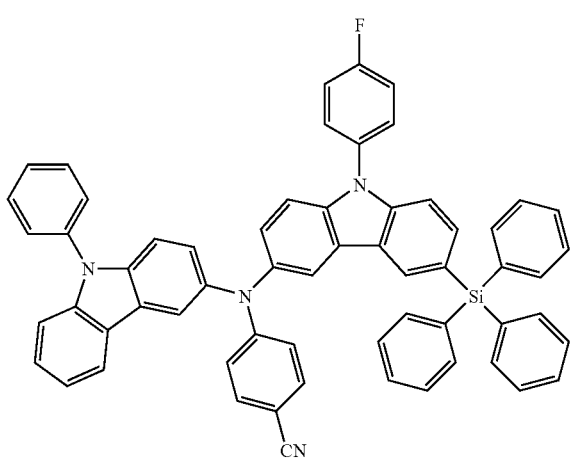
159
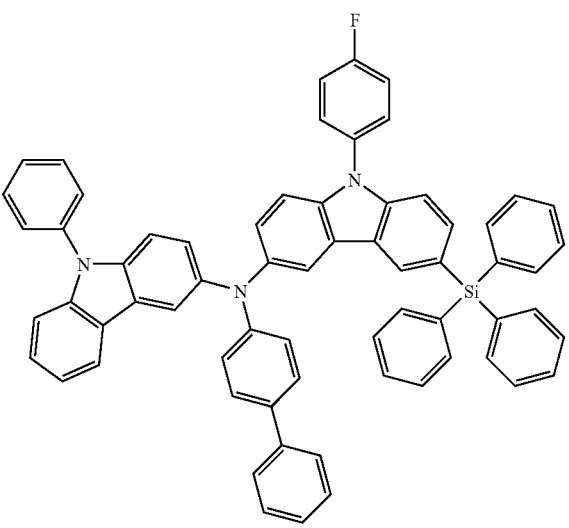

160
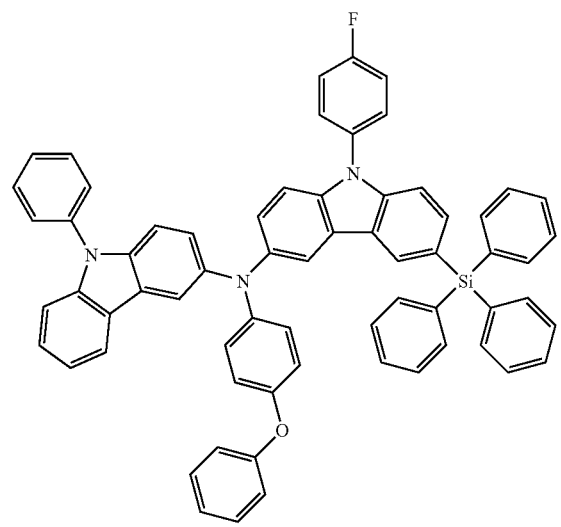
161
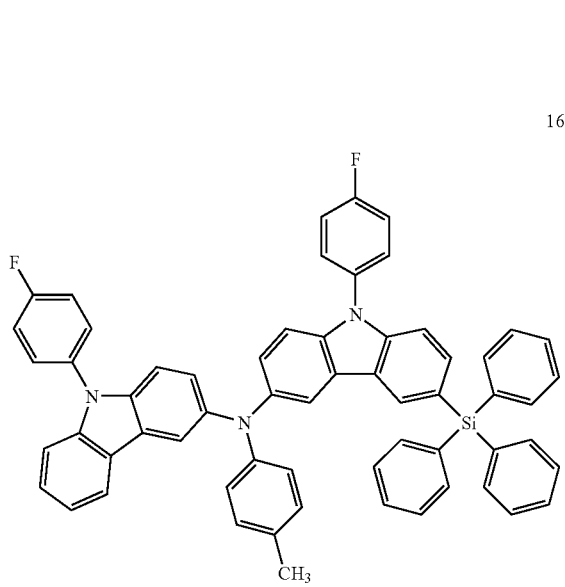
162
163
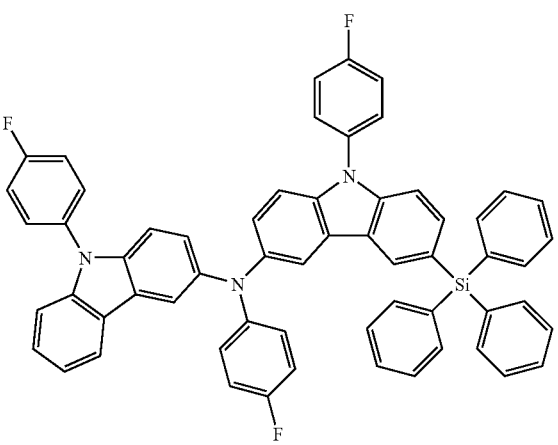
164
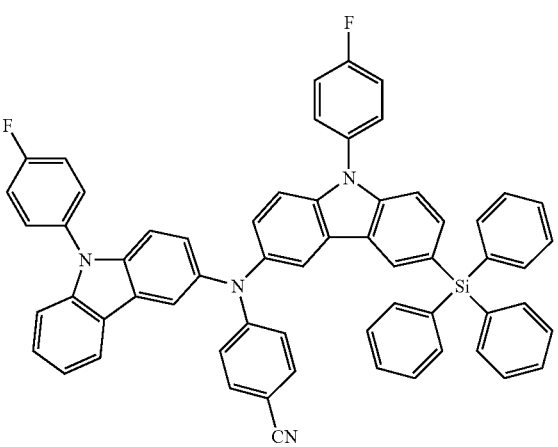
165
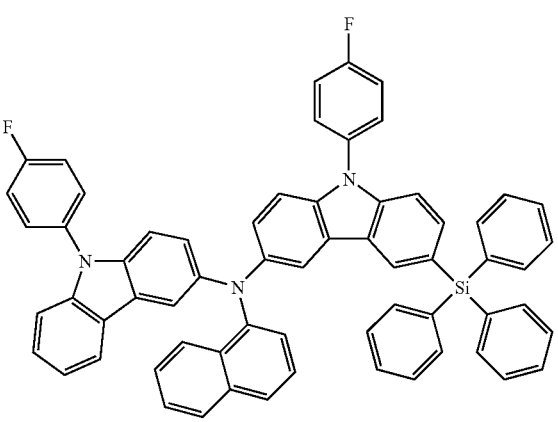

-continued

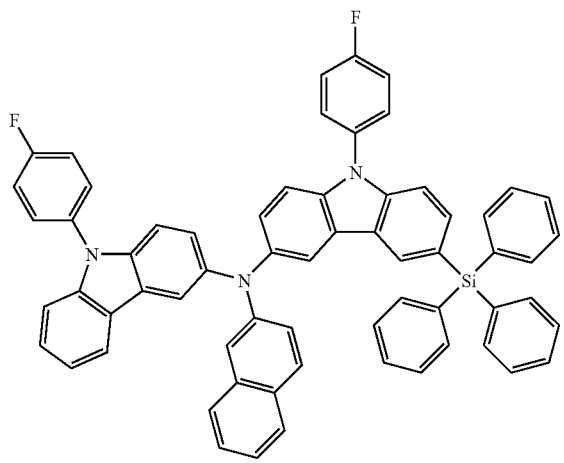

166

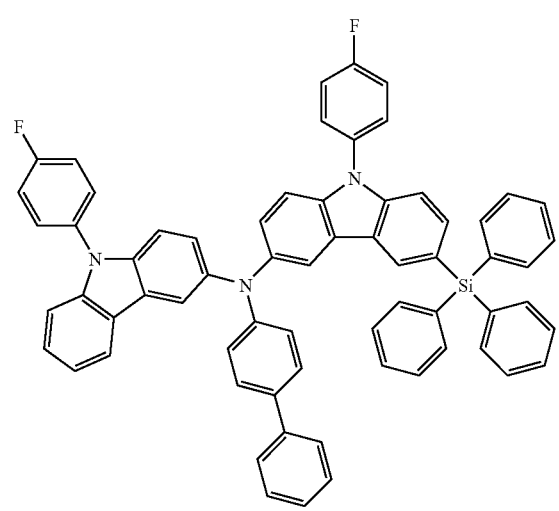

167

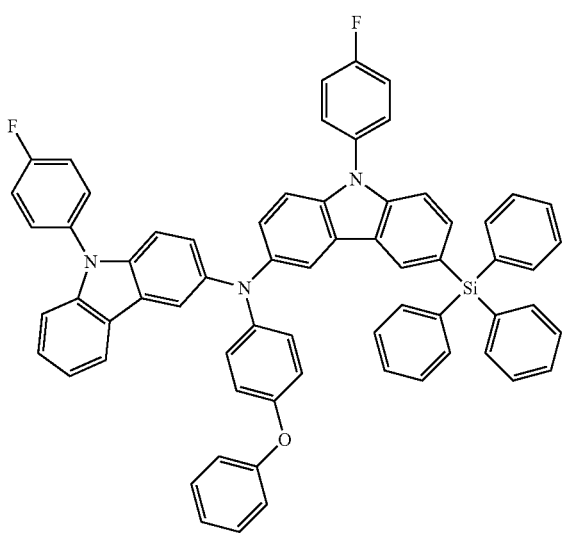

168

The silanylamine-based compound represented by Formula 1 may be prepared by various methods. According to one embodiment of the present invention, as shown in Reaction Scheme 1 below, a compound represented by Formula 1a is reacted with a compound represented by Formula 1b to prepare a silanylamine-based compound represented by Formula 1.

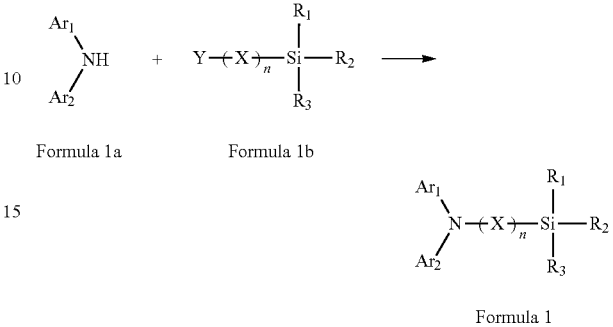

Formula 1a    Formula 1b

Formula 1

In Formulae 1a, 1b and 1, X, n, $Ar_1$, $Ar_2$, $R_1$, $R_2$ and $R_3$ are as described above, and Y is a halogen atom such as F, Cl, Br or I.

The reaction represented by Reaction Scheme 1 may be performed in the presence of $Pd_2(dba)_3$ (where dba is dibenzylideneacetone), sodium tert-butoxide and tri(tert-butyl) phosphine and may be performed at a temperature ranging from about 50 to about 150° C.

According to another embodiment of the present invention, an organic light emitting device includes a first electrode, a second electrode and an organic layer positioned between the first electrode and the second electrode. The organic layer includes a silanylamine-based compound represented by Formula 1. The organic layer including the silanylamine-based compound represented by Formula 1 may be a hole injection layer, a hole transport layer, or a single layer having both hole injection and hole transport capabilities. The organic layer including the silanylamine-based compound represented by Formula 1 may also be an emissive layer. The emissive layer may include phosphorescent materials or fluorescent materials. The first electrode may be an anode and the second electrode may be a cathode, or the first electrode may be a cathode and the second electrode may be an anode.

The organic light emitting device may further include at least one layer selected from a hole injection layer, a hole transport layer, an electron blocking layer, an emissive layer, a hole blocking layer, an electron transport layer and an electron injection layer. For example, the organic light emitting device may have a first electrode/hole injection layer/ emissive layer/second electrode structure, a first electrode/ hole injection layer/hole transport layer/emissive layer/ electron transport layer/second electrode structure, or a first electrode/hole injection layer/hole transport layer/emissive layer/electron transport layer/electron injection layer/second electrode structure. The organic light emitting device may also have a first electrode/single layer/emissive layer/electron transport layer/second electrode structure, or a first electrode/ single layer/emissive layer/electron transport layer/electron injection layer/second electrode structure, where the single layer has both hole injection and hole transport capabilities.

Hereinafter, a method of preparing an organic light emitting device according to one embodiment of the present invention will be described with reference to FIG. 1. FIG. 1 is a schematic showing an organic light emitting device according to one embodiment of the present invention. The organic light emitting device illustrated in FIG. 1 includes a substrate, a first electrode (anode), a hole injection layer, a hole transport layer, an emissive layer, an electron transport layer, an electron injection layer and a second electrode (cathode).

According to one embodiment of the present invention, the first electrode is first formed by depositing or sputtering a high work-function material on a substrate. The first electrode may be an anode or a cathode. The substrate can be any substrate used in conventional organic light emitting devices, and may be a glass substrate or a transparent plastic substrate that is waterproof and has excellent mechanical strength, thermal stability, transparency, surface smoothness and ease of handling. Nonlimiting examples of suitable materials for forming the first electrode include ITO, IZO, $SnO_2$, ZnO, Al, Ag, Mg, and any material with high conductivity.

Then, the hole injection layer (HIL) may be formed on the first electrode by vacuum deposition, spin coating, casting, Langmuir Blodgett (LB) deposition, or the like.

When the HIL is formed using vacuum deposition, the deposition conditions may vary depending on the compound used to form the HIL, and the structure and thermal properties of the HIL to be formed. In general, however, the vacuum deposition conditions may include a deposition temperature ranging from about 100 to about 500° C., a pressure ranging from about $10^{-8}$ to about $10^{-3}$ torr, a deposition velocity ranging from about 0.01 to about 100 Å/sec, and a layer thickness ranging from about 10 Å to 5 μm.

When the HIL is formed by spin coating, the coating conditions may vary depending on the compound used to form the HIL, and the structure and thermal properties of the HIL to be formed. In general, however, the coating velocity may range from about 2000 to about 5000 rpm, and the heat treatment temperature (performed to remove solvent after coating) may range from about 80 to about 200° C.

The material used to form the HIL may be a silanylamine-based compound represented by Formula 1 or may be a material known in the art. Nonlimiting examples of suitable materials for the HIL include phthalocyanine compounds (such as a copper phthalocyanine), star-burst type amine derivatives (such as TCTA, m-MTDATA, and m-MTDAPB), polyaniline/Dodecylbenzenesulfonic acid (Pani/DBSA), poly(3,4-ethylenedioxythiophene)/Poly(4-styrenesulfonate) (PEDOT/PSS), polyaniline/camphor sulfonic acid (Pani/CSA), (polyaniline)/poly(4-styrenesulfonate) (PANI/PSS) and similar soluble and conductive polymers.

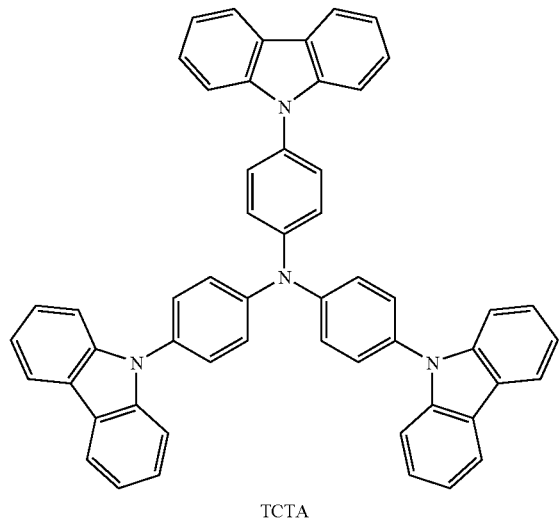

TCTA

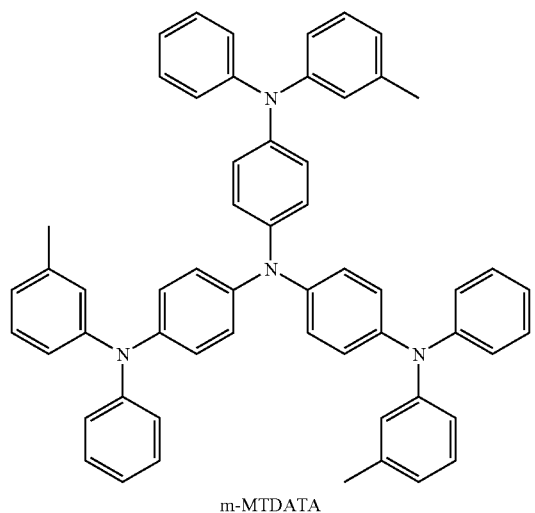

m-MTDATA

The thickness of the HIL may range from about 100 to about 10000 Å. In one embodiment, for example, the thickness of the HIL ranges from about 100 to about 100 Å. When the thickness of the HIL is within these ranges, excellent hole injecting capabilities and driving voltages of the organic light emitting device may be obtained.

Then, the hole transport layer (HTL) may be formed on the HIL by vacuum deposition, spin coating, casting, LB deposition, or the like. When the HTL is formed by vacuum deposition or spin coating, deposition and coating conditions are similar to those for formation of the HIL, although the deposition and coating conditions may vary depending on the compound used to form the HTL.

The material used to form the HTL may be a silanylamine-based compound represented by Formula 1, or a material known in the art. Nonlimiting examples of suitable materials for forming the HTL include carbazole derivatives (such as N-phenylcarbazole, polyvinylcarbazole and the like), conventional amine derivatives having aromatic condensation rings (such as 4,4'-bis[N-(1-naphthyl)-N-phenylamino]biphenyl (NPB), N,N'-bis(3-methylphenyl)-N,N'-diphenyl-[1,1-biphenyl]-4,4'-diamine (TPD), and N,N'-di(naphthalene-1-yl)-N,N'-diphenyl benzydine (α-NPD)), and the like.

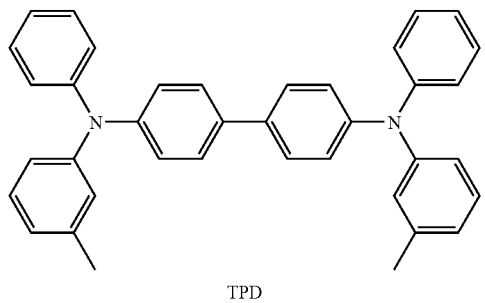

TPD

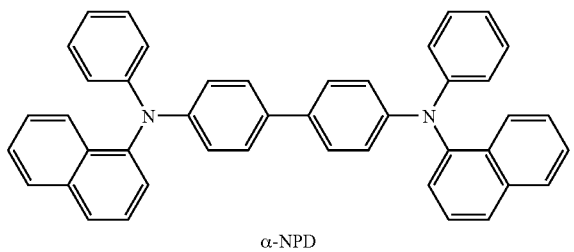

α-NPD

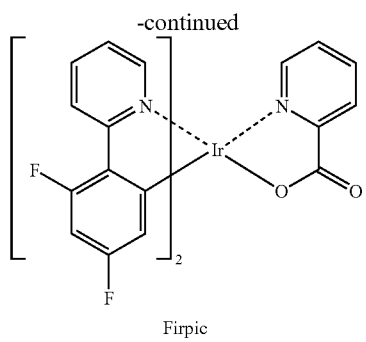

Firpic

The thickness of the HTL may range from about 50 to about 1000 Å. In one embodiment, for example, the thickness of the HTL ranges from about 100 to about 600 Å. When the thickness of the HTL is within these ranges, excellent hole transporting capabilities and driving voltages of the organic light emitting device may be obtained.

Then, the emissive layer (EML) may be formed on the HTL by vacuum deposition, spin coating, casting, LB, or the like. When the EML is formed by vacuum deposition or spin coating, deposition and coating conditions are similar to those for formation of the HIL, although the deposition and coating conditions may vary depending on the compound used to form the EML.

The material used to form the EML may be a silanylamine-based compound represented by Formula 1 or various light emitting materials, such as hosts and dopants that are known in the art. The dopants may be fluorescent and/or phosphorescent dopants that are known in the art.

Nonlimiting examples of suitable host materials include $Alq_3$, 4,4'-N,N'-dicarbazole-biphenyl (CBP), poly(n-vinylcarbazole) (PVK), distyrylarylene (DSA), or IDE215 from Idemitsu Co.

Nonlimiting examples of suitable fluorescent dopants include IDE102, IDE105 and IDE118 from Idemitsu Co. Nonlimiting examples of suitable phosphorescent dopants include $Ir(ppy)_3$ (green, where ppy is 2-phenylpyridine) (green), $(4,6-F2\ ppy)_2Irpic$, TEB002 from Covion Co., platinum(II) octaethylporphyrin (PtOEP), compounds represented by Formula 5 below, Firpic, and red phosphorescent dopant RD 61 from UDC Co.

Formula 5

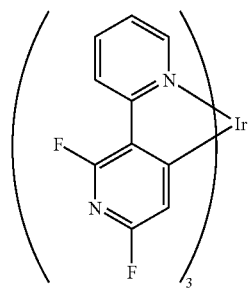

The amount of the dopant may range from about 0.1 to 20 parts by weight based on 100 parts by weight of the material used to form the EML (i.e., based on 100 parts by weight of the host and the dopant). In one embodiment, for example, the amount of the dopant ranges from about 0.5 to about 12 parts by weight based on 100 parts by weight of the material used to form the EML. When the amount of the dopant is greater than about 0.1 parts by weight, the effect achieved by adding the dopant is sufficient. Also, when the amount of the dopant is less than about 20 parts by weight, fluorescence or phosphorescence quenching may be prevented.

The thickness of the EML may range from about 100 to about 1000 Å. In one embodiment, for example, the thickness of the EML ranges from about 200 to about 600 Å. When the thickness of the EML is within these ranges, excellent emitting abilities of the EML, and driving voltages of the organic light emitting device may be obtained.

When the EML includes a phosphorescent dopant, a hole blocking layer (HBL) (not shown) may be formed on the EML to prevent diffusion of triplet excitons or holes into the electron transport layer. Nonlimiting examples of suitable materials for forming the HBL include oxadiazole derivatives, triazole derivatives, phenanthroline derivatives, Balq, and BCP.

The thickness of the HBL may range from about 50 to about 1000 Å. In one embodiment, for example, the thickness of the HBL ranges from about 100 to about 300 Å. When the thickness of the HBL is within these ranges, excellent hole blocking abilities of the HBL and driving voltages of the organic light emitting device may be obtained.

Then, the electron transport layer (ETL) may be formed on the HBL by vacuum deposition, spin coating, casting, or the like. When the ETL is formed by vacuum deposition or spin coating, deposition and coating conditions are similar to those for formation of the HIL, although the deposition and coating conditions may vary depending on the compound used to form the ETL.

Nonlimiting examples of suitable materials for forming the ETL include quinoline derivatives (for example, tris(8-quinolinorate)aluminum ($Alq_3$)), TAZ, and the like.

The thickness of the ETL may range from about 100 to about 1000 Å. In one embodiment, for example, the thickness of the ETL ranges from about 100 to about 500 Å. When the thickness of the ETL is within these ranges, excellent electron transporting abilities of the ETL and driving voltages of the organic light emitting device may be obtained.

Then, the electron injection layer (EIL) may be formed on the ETL for example, by vacuum deposition, spin coating, casting, or the like. The EIL is formed of a material that allows easy injection of electrons from a cathode.

Nonlimiting examples of suitable materials for forming the EIL include LiF, NaCl, CsF, $Li_2O$, BaO, and the like. Deposition and coating conditions are similar to those for formation of the HIL, although the deposition and coating conditions may vary depending on the material used to form the EIL.

The thickness of the EIL may range from about 1 to about 100 Å. In one embodiment, for example, the thickness of the EIL ranges from about 5 to about 90 Å. When the thickness of the EIL is within these ranges, excellent electron injection abilities of the EIL and driving voltages of the organic light emitting device may be obtained.

Finally, the second electrode can be formed on the EIL by vacuum deposition, sputtering, or the like. The second electrode can be used as a cathode or an anode. The material used to form the second electrode may be a low work-function metal, alloy, electrically conductive compound, or a combination thereof. Nonlimiting examples of suitable materials for the second electrode include Li, Mg, Al, Al—Li, Ca, Mg—In, Mg—Ag, and the like. In addition, a transparent cathode formed of ITO or IZO can be used to produce a front surface light emitting device.

Hereinafter, Synthesis Examples of Compounds 9, 43, 44, 45, and 137 and Examples are presented. However, the Synthesis Examples and Examples are presented for illustrative purposes only and are not intended to limit the scope of the present invention.

SYNTHESIS EXAMPLE 1

Synthesis of Compound 9

Compound 9 was synthesized via Reaction Scheme 2 below:

Synthesis of Intermediate A 3.12 g (10 mmol) of dibromobiphenyl was dissolved in 30 mL of THF, and 4 mL of 2.5M n-butyllithium (in Hexane) was added thereto at −78° C. 2.95 g (10 mmol) of chlorotriphenylsilane dissolved in 5 mL of THF was gradually added thereto at −78° C. after one hour. The mixture was stirred at room temperature for 5 hours, water was added thereto and the mixture was washed three times with 30 mL of diethylether. The washed diethylether layer was dried over $MgSO_4$ and dried under reduced pressure to obtain a product. The obtained product was purified by silica gel column chromatography to obtain 2.9 g of white solid intermediate A (Yield: 60%). ($^1$H NMR ($CDCl_3$, 400 MHz) δ (ppm) 7.65-7.53 (m, 12H), 7.47-7.36 (m, 11H)).

Synthesis of Compound 9

4.9 g (10 mmol) of intermediate A, 2.6 g (12 mmol) of 2-naphthylphenylamine, 2.9 mg (30 mmol) of t-BuONa, 183 mg (0.2 mmol) of $Pd_2(dba)_3$, 40 mg (0.2 mmol) of $P(t-Bu)_3$ were dissolved in 40 mL of toluene and stirred at 90° C. for three hours.

When the reaction was completed, the mixture was cooled to room temperature and extracted three times with 40 mL of distilled water and diethylether. A collected organic layer was dried over $MgSO_4$ to evaporate the solvent. The residue was purified using silica gel column chromatography to obtain 5.67 g of yellow solid Compound 9 (Yield: 90%). ($^1$H NMR ($CD_2Cl_2$, 400 MHz) δ (ppm) 7.75 (t, 2H), 7.63-7.56 (m, 12H), 7.53 (d, 2H), 7.46-7.34 (m, 12H), 7.30-7.26 (m, 3H), 7.16 (d, 4H), 7.06 (t, 1H); $^{13}$C NMR ($CD_2Cl_2$, 100 MHz) δ (ppm) 147.6, 147.5, 145.3, 141.7, 136.9, 136.3, 134.8, 134.5, 134.2,

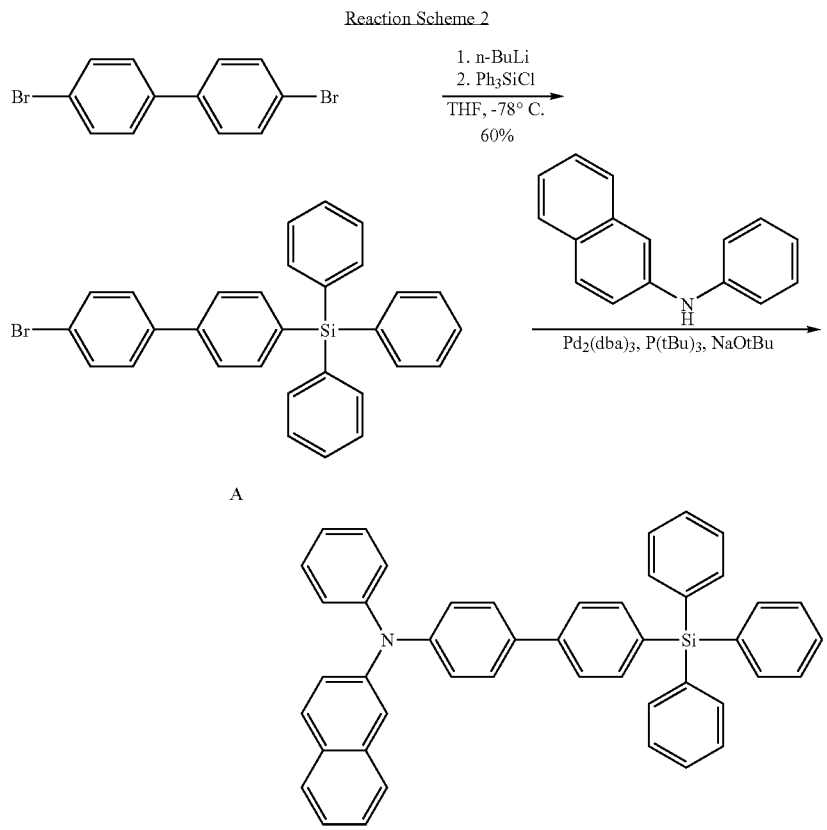

132.4, 130.2, 129.7, 129.4, 128.9, 127.9, 127.8, 127.5, 126.9, 126.3, 126.0, 124.8, 124.6, 124.5, 124.0, 123.3, 120.5).

The UV absorption spectrum of 0.2 mM of the obtained Compound 9 diluted in $CH_2Cl_2$ was measured, and the maximum absorption spectrum was 340 nm.

Deposition temperature (Td) and glass transition temperature (Tg) were measured by performing thermal analysis using thermo gravimetric analysis (TGA) and differential scanning calorimetry (DSC) under the following conditions: $N_2$ atmosphere, temperatures of room temperature to 600° C. (10° C./min) for TGA and room temperature to 400° C. for DSC, and Pan Type: Pt Pan in disposable Al Pan (TGA) and disposable Al pan (DSC). Td was 330° C., and Tg was 97° C.

The highest occupied molecular orbital (HOMO) and lowest occupied molecular orbital (LUMO) were measured using the UV absorption spectrum and an ionization potential measurement AC-2. The HOMO was 5.4 eV and the LUMO was 2.33 eV.

SYNTHESIS EXAMPLE 2

Synthesis of Compound 43

Compound 43 was synthesized via Reaction Scheme 3 below:

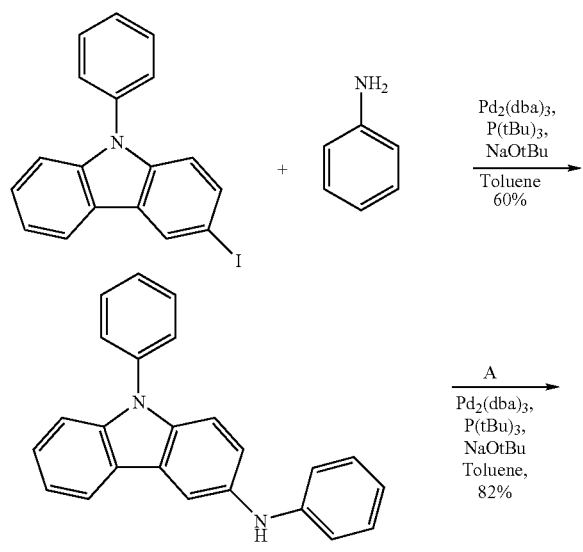

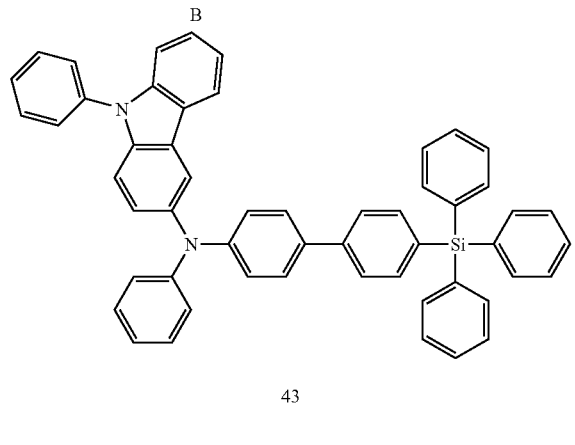

Synthesis of Intermediate B 3.69 g (10.0 mmol) of 3-iodo-9-phenylcarbazole, 1.11 g (12.0 mmol) of aniline, 2.88 g (30.0 mmol) of t-BuONa, 183 mg (0.2 mmol) of $Pd_2(dba)_3$, 40 mg (0.2 mmol) of $P(t-Bu)_3$ were dissolved in 40 mL of toluene, and stirred at 90° C. for 3 hours.

When the reaction was completed, the mixture was cooled to room temperature and distilled water was added thereto. The mixture was extracted three times with 40 mL of diethylether. A collected organic layer was dried over $MgSO_4$ to evaporate the solvent. The residue was purified using silica gel column chromatography to obtain 2.17 g of white solid Intermediate B (Yield: 65%). ($^1$H NMR ($CDCl_3$, 400 MHz) δ (ppm) 8.01 (m, 1H), 7.66 (m, 1H), 7.51-7.33 (m, 7H), 7.21-6.94 (m, 5H), 6.73 (m, 1H), 5.68 (bs, 1H); $^{13}$C NMR ($CDCl_3$, 100 MHz) δ (ppm) 144.6, 139.8, 137.4, 135.7, 129.8, 129.3, 128.0, 127.4, 127.1, 126.5, 119.1, 119.0, 118.6, 118.4, 116.7, 113.1, 111.1, 109.4, 102.4).

Synthesis of Compound 43

Compound 43 was obtained as in Synthesis Example 1, except that Intermediate B was used instead of 2-naphthylphenylamine (Yield: 82%). ($^1$H NMR ($CDCl_3$, 300 MHz) δ (ppm) 7.98 (d, 1H), 7.69 (bd, 1H), 7.67-7.54 (m, 14H), 7.50-7.33 (m, 14H), 7.28-7.13 (m, 9H), 6.97 (t, 1H); DEPT $^{13}$C NMR ($CDCl_3$, 100 MHz) δ (ppm) 136.9, 136.5, 130.0, 129.6, 129.2, 127.9, 127.7, 127.5, 127.1, 126.2, 126.0, 125.8, 123.3, 122.3, 122.1, 120.6, 120.0, 118.8, 110.8, 110.0).

The UV absorption spectrum of 0.2 mM of the obtained Compound 43 diluted in $CH_2Cl_2$ was measured, and the maximum absorption spectrum was 345 and 310 nm.

Td and Tg were measured by performing thermal analysis using thermo gravimetric analysis (TGA) and differential scanning calorimetry (DSC) under the following conditions: $N_2$ atmosphere, temperatures of room temperature to 600° C. (10° C./min) for TGA and of room temperature to 400° C. for DSC, and Pan Type: Pt Pan in disposable Al Pan (TGA) and disposable Al pan (DSC). Td was 380° C., and Tg was 127° C.

The HOMO and LUMO were measured using the UV absorption spectrum and an ionization potential measurement AC-2. The HOMO was 5.30 eV and the LUMO was 2.24 eV.

SYNTHESIS EXAMPLE 3

Synthesis of Compound 44

Compound 44 was synthesized via Reaction Scheme 4 below:

Reaction Scheme 4

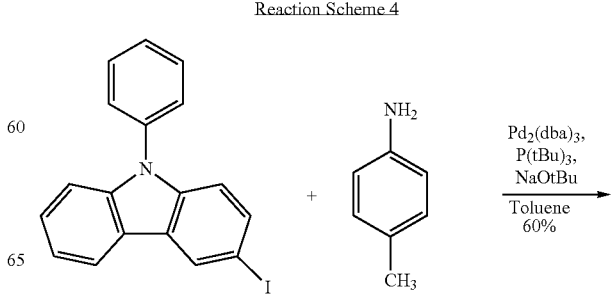

-continued

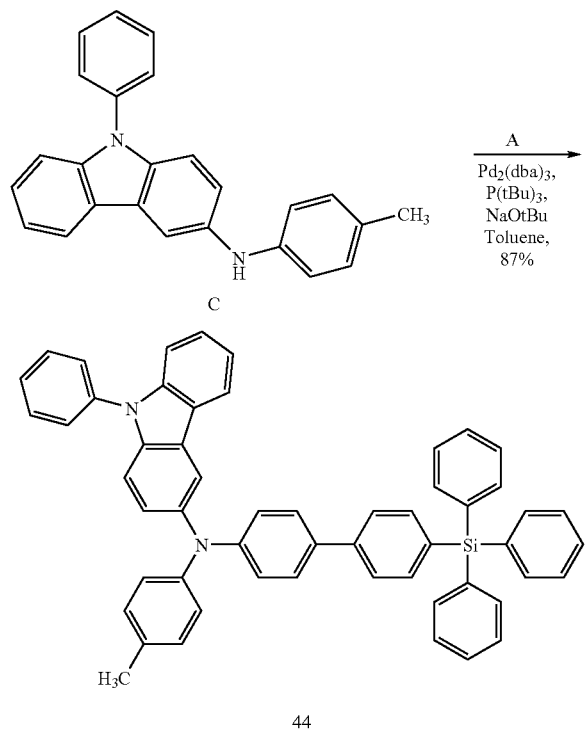

44

Synthesis of Intermediate C

Intermediate C was synthesized as in Synthesis Example 1, except that benzylamine was used instead of aniline. (NMR (CDCl$_3$, 400 MHz) δ (ppm) 8.02 (m, 1H), 7.67 (m, 1H), 7.52-7.31 (m, 7H), 7.02-6.86 (m, 5H), 6.10 (bs, 1H), 2.25 (s, 3H); $^{13}$C NMR (CDCl$_3$, 100 MHz) δ (ppm) 140.1, 138.8, 136.4, 134.7, 128.8, 127.3, 127.0, 126.4, 126.1, 125.5, 118.1, 118.0, 117.6, 117.4, 116.7, 112.1, 110.1, 108.4, 101.4, 20.3).

Synthesis of Compound 44

Compound 44 was obtained as in Synthesis Example 1, except that Intermediate C was used instead of 2-naphthylphenylamine (Yield: 87%). ($^1$H NMR (CDCl$_3$, 400 MHz) δ (ppm) 8.09 (d, 1H), 8.01 (d, 1H), 7.70-7.52 (m, 17H), 7.49-7.35 (m, 12H), 7.24-7.18 (m, 2H), 7.11 (d, 2H), 7.04 (t, 4H), 2.28 (t, 3H); $^{13}$C NMR (CDCl$_3$, 100 MHz) δ (ppm) 149.5, 146.4, 142.6, 142.2, 141.3, 138.9, 138.3, 137.5, 137.0, 135.0, 133.2, 133.1, 132.6, 130.9, 130.7, 130.5, 128.8, 128.5, 128.3, 127.7, 127.1, 126.5, 125.2, 125.0, 123.8, 121.9, 121.4, 120.8, 119.3, 111.5, 110.6, 20.7).

The UV absorption spectrum of 0.2 mM of the obtained Compound 44 diluted in CH$_2$Cl$_2$ was measured, and the maximum absorption spectrum was 343, 313, and 245 nm.

Td and Tg were measured by performing thermal analysis using thermo gravimetric analysis (TGA) and differential scanning calorimetry (DSC) under the following conditions: N$_2$ atmosphere, temperatures of room temperature to 600° C. (10° C./min) for TGA and of room temperature to 400° C. for DSC, and Pan Type: Pt Pan in disposable Al Pan (TGA) and disposable Al pan(DSC). Td was 414° C., and Tg was 129° C.

The HOMO and LUMO were measured using the UV absorption spectrum and an ionization potential measurement AC-2. The HOMO was 5.20 eV and the LUMO was 2.21 eV.

SYNTHESIS EXAMPLE 4

Synthesis of Compound 45

Compound 45 was synthesized via Reaction Scheme 5 below:

Reaction Scheme 5

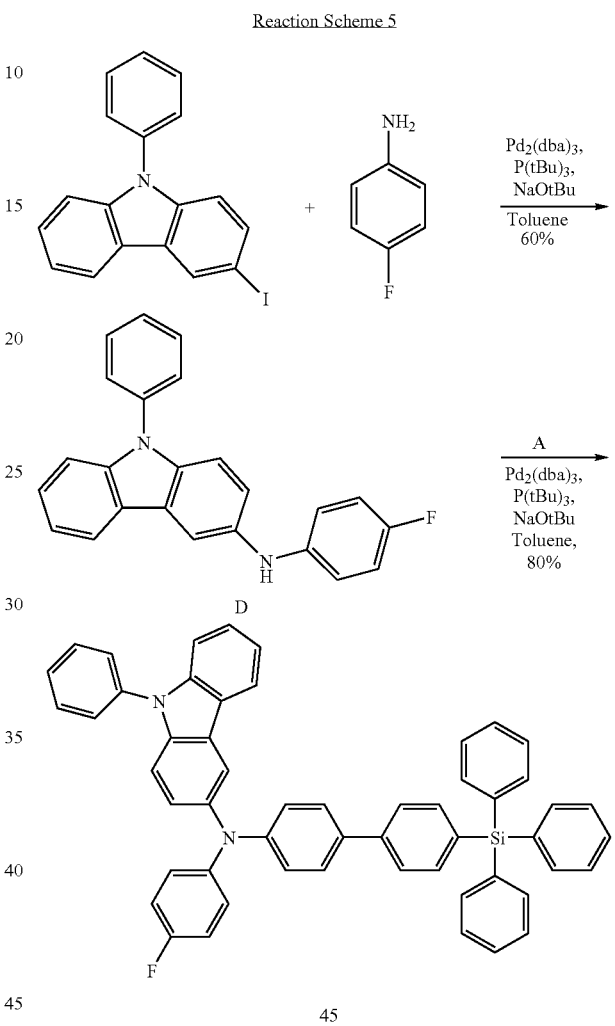

45

Synthesis of Intermediate D

Intermediate D was synthesized as in Synthesis Example 1, except that fluoroaniline was used instead of aniline. (NMR (CDCl$_3$, 400 MHz) δ (ppm) 8.02 (m, 1H), 7.97-7.92 (m, 2H), 7.66 (m, 1H), 7.48-7.18 (m, 9H), 6.94 (m, 1H), 6.50 (bs, 1H); $^{13}$C NMR (CDCl$_3$, 100 MHz) δ (ppm) 157.8 (d), 140.7 (d), 137.8, 135.4, 133.7, 127.8, 126.3, 126.0, 125.4, 125.1, 124.5, 117.1, 117.0, 116.6, 116.4, 115.7, 111.1, 109.1, 107.4, 100.4).

Synthesis of Compound 45

Compound 45 was obtained as in Synthesis Example 1, except that Intermediate D was used instead of 2-naphthylphenylamine (Yield: 80%). ($^1$H NMR (Acetone-d6, 400 MHz) δ (ppm) 8.06 (d, 1H), 8.02 (d, 1H), 7.68-7.50 (m, 16H), 7.47-7.34 (m, 13H), 7.21-7.13 (m, 4H), 7.07-7.00 (m, 4H); $^{13}$C NMR (CDCl$_3$, 100 MHz) δ (ppm) 159.8, 157.4, 148.7, 144.5, 141.8, 141.4, 140.3, 138.2, 137.5, 136.8, 136.2, 134.2, 132.8, 131.9, 130.1, 129.8, 128.0, 127.7, 127.6, 126.9, 126.4, 125.9, 125.8, 125.6, 124.5, 123.0, 121.2, 120.6, 120.1, 118.5, 116.1, 115.8, 110.9, 109.8).

The UV absorption spectrum of 0.2 mM of the obtained Compound 45 diluted in $CH_2Cl_2$ was measured, and the maximum absorption spectrum was 338, 309, and 243 nm.

Td and Tg were measured by performing thermal analysis using thermo gravimetric analysis (TGA) and differential scanning calorimetry (DSC) under the following conditions: $N_2$ atmosphere, temperatures of room temperature to 600° C. (10° C./min) for TGA and of room temperature to 400° C. for DSC, and Pan Type: Pt Pan in disposable Al Pan (TGA) and disposable Al pan(DSC). Td was 405° C., and Tg was 126° C.

The HOMO and LUMO were measured using the UV absorption spectrum and an ionization potential measurement AC-2. The HOMO was 5.20 eV and the LUMO was 2.22 eV.

SYNTHESIS EXAMPLE 5

Synthesis of Compound 137

Compound 137 was synthesized via Reaction Scheme 6 below:

Reaction Scheme 6

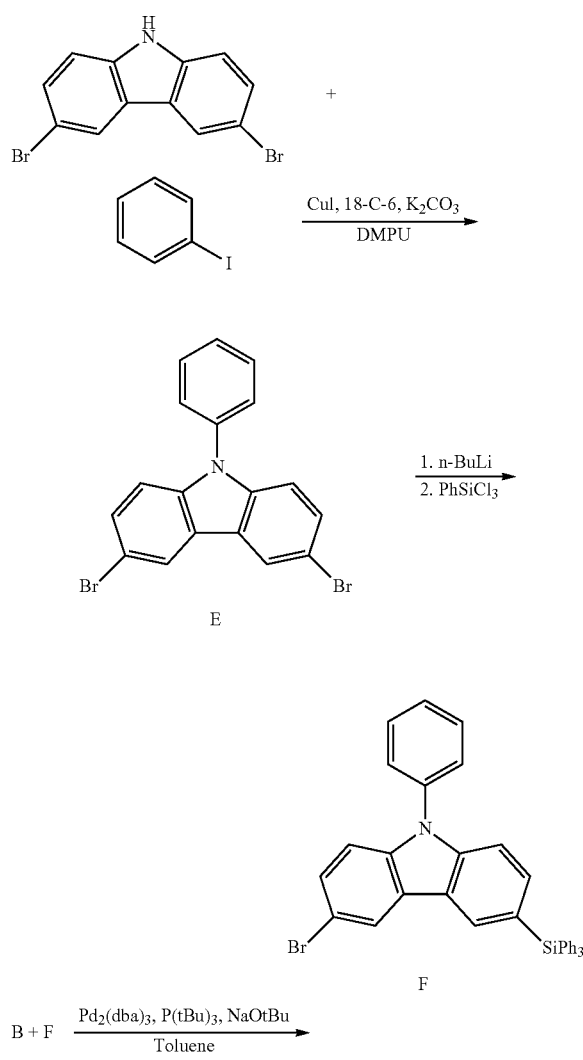

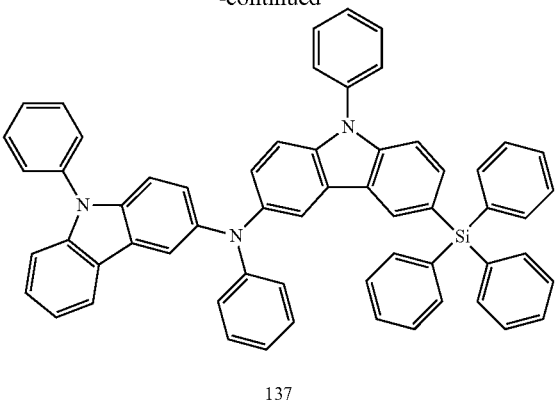

137

Synthesis of Intermediate E 3.25 g (10.0 mmol) of 3, 6-dibromocarbazole, 10.2 g (50.0 mmole) iodobenzene, 190 mg (1.0 mmole) of CuI, 132 mg (0.5 mmole) of 18-C-6, 2.76 g (20.0 mmole) of $K_2CO_3$ were dissolved in 50 mL of DMPU, and stirred at 170° C. for 20 hours. The mixture was cooled to room temperature and 50 mL of diethylether was added thereto. Then the mixture was washed with plenty of water and ammonium hydroxide solution. A collected organic layer was dried over $MgSO_4$ to evaporate the solvent. The residue was purified using silica gel column chromatography to obtain 3.40 g of white solid Intermediate E (Yield: 85%). (NMR ($CDCl_3$, 400 MHz) δ (ppm) 7.92 (m, 2H), 7.55-7.47 (m, 6H), 7.36-7.16 (m, 3H); $^{13}C$ NMR ($CDCl_3$, 100 MHz) δ (ppm) 142.6, 137.6, 130.2, 129.8, 127.4, 127.0, 122.8, 122.5, 115.3, 111.3).

Synthesis of Intermediate F 4.01 g (10 mmol) of Intermediate E was dissolved in 20 mL of THF, and 4.6 mL (12.0 mmol) of 2.6M n-butyllithium (in Hexane) was added thereto at −78° C. for 10 minutes. 3.83 g (13.0 mmol) of chlorotriphenylsilane dissolved in 20 mL of THF was gradually added thereto at −78° C. for 20 minutes, and the mixture was stirred at room temperature for 17 hours. 50 mL of water was added to the mixture and the mixture was extracted twice with 50 mL of diethylether. A collected organic layer was dried over $MgSO_4$ to evaporate the solvent. The residue was purified using silica gel column chromatography to obtain 3.19 g of white solid Intermediate F (Yield: 55%). (NMR ($CDCl_3$, 400 MHz) δ (ppm) 8.28-8.21 (m, 3H), 8.14 (d, 2H), 7.86-7.14 (m, 21H); $^{13}C$ NMR ($CDCl_3$, 100 MHz) δ (ppm) 143.1, 137.9, 136.4, 134.4, 133.9, 133.7, 129.8, 129.5, 129.0, 128.0, 127.9, 127.5, 126.9, 124.9, 123.9, 123.1, 118.3, 111.2, 109.7, 107.6).

Synthesis of Compound 137

Compound 137 was obtained as in Synthesis Example 2, except that Intermediate F was used instead of Intermediate A (Yield: 80%). ($^1H$ NMR ($CDCl_3$, 300 MHz) δ (ppm) 8.25 (s, 1H), 7.94 (d, 3H), 7.64-7.52 (m, 15H), 7.43-7.24 (m, 18H), 7.20-7.14 (m, 3H), 7.02 (d, 2H), 6.83 (t, 1H)).

The UV absorption spectrum of 0.2 mM of the obtained Compound 137 diluted in $CH_2Cl_2$ was measured, and the maximum absorption spectrum was 317 nm.

Td and Tg were measured by performing thermal analysis using thermo gravimetric analysis (TGA) and differential scanning calorimetry (DSC) under the following conditions: $N_2$ atmosphere, temperatures of room temperature to 600° C. (10° C./min) for TGA and of room temperature to 400° C. for DSC, and Pan Type: Pt Pan in disposable Al Pan (TGA) and disposable Al pan (DSC). Td was 390° C., and Tg was 148° C.

The HOMO and LUMO were measured using the UV absorption spectrum and an ionization potential measurement AC-2. The HOMO was 5.1 eV and the LUMO was 2.15 eV.

EXAMPLE 1

A Corning 15Ω/cm² (1,200 Å) ITO glass substrate was cut into 50 mm×50 mm×0.7 mm size pieces, ultrasonicwashed with isopropyl alcohol for 5 minutes, ultrasonicwashed with deionized water for 5 minutes, and washed with UV ozone for 30 minutes. Then, the glass substrate was installed in a vacuum deposition device.

Compound 9 was vacuum deposited on the substrate to form a HIL with a thickness of 600 Å. 4,4'-bis[N-(1-naphthyl)-N-phenylamino]biphenyl (NPB) was vacuum deposited on the HIL to form a HTL with a thickness of 300 Å.

IDE215 (a blue fluorescent host obtained from Idemitsu Co.) and IDE118 (a blue fluorescent dopant obtained from Idemitsu Co.) (98:2, w/w) were vacuum deposited on the HTL to form an EML with a thickness of 300 Å.

Then, Alq₃ was vacuum deposited on the EML to form an ETL with a thickness of 300 Å, LiF was vacuum deposited on the ETL to form an EIL with a thickness of 10 Å, and Al was vacuum deposited on the EIL to a thickness of 3000 Å (cathode) to form a LiF/Al electrode to complete the manufacture of an organic light emitting device.

EXAMPLE 2

An organic light emitting device was prepared as in Example 1, except that Compound 43 was used instead of Compound 9 in forming the HIL.

EXAMPLE 3

An organic light emitting device was prepared as in Example 1, except that Compound 44 was used instead of Compound 9 in forming the HIL.

EXAMPLE 4

An organic light emitting device was prepared as in Example 1, except that Compound 45 was used instead of Compound 9 in forming the HIL.

EXAMPLE 5

An organic light emitting device was prepared as in Example 1, except that Compound 137 was used instead of Compound 9 in forming the HIL.

COMPARATIVE EXAMPLE 1

An organic light emitting device was prepared as in Example 1, except that IDE406 (from Idemitsu Co.) was used instead of Compound 9 in forming the HIL.

EVALUATION EXAMPLE

Figure 2:
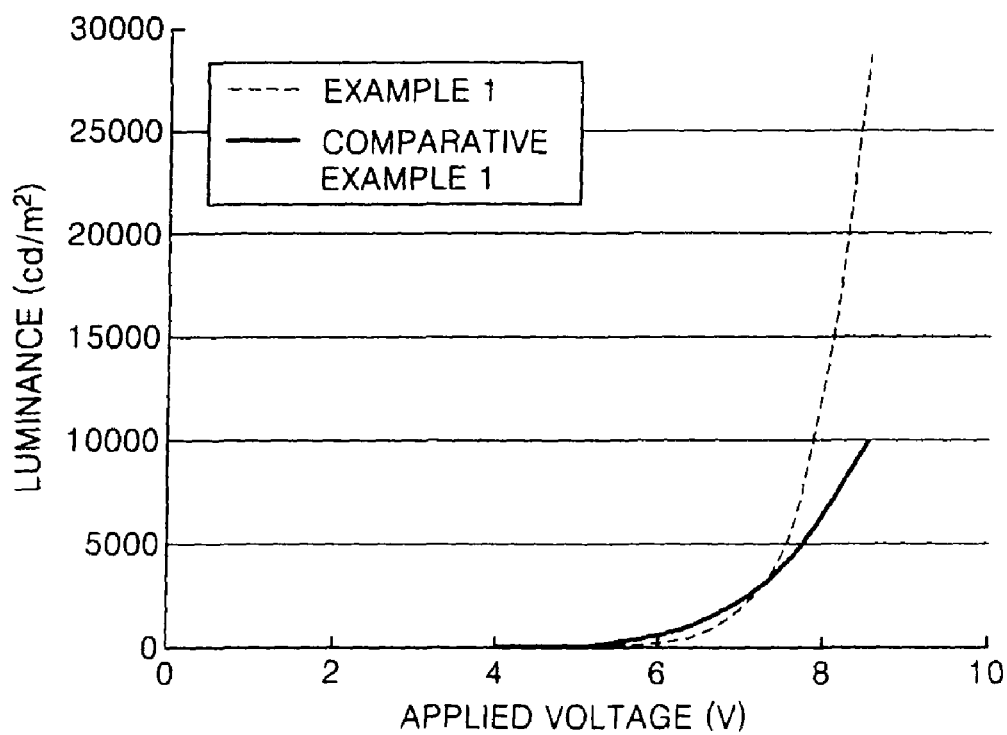
FIG. 2 is a graph of luminance according to driving voltage of organic light emitting devices prepared according to Example 1 and Comparative Example 1.
Figure 3:
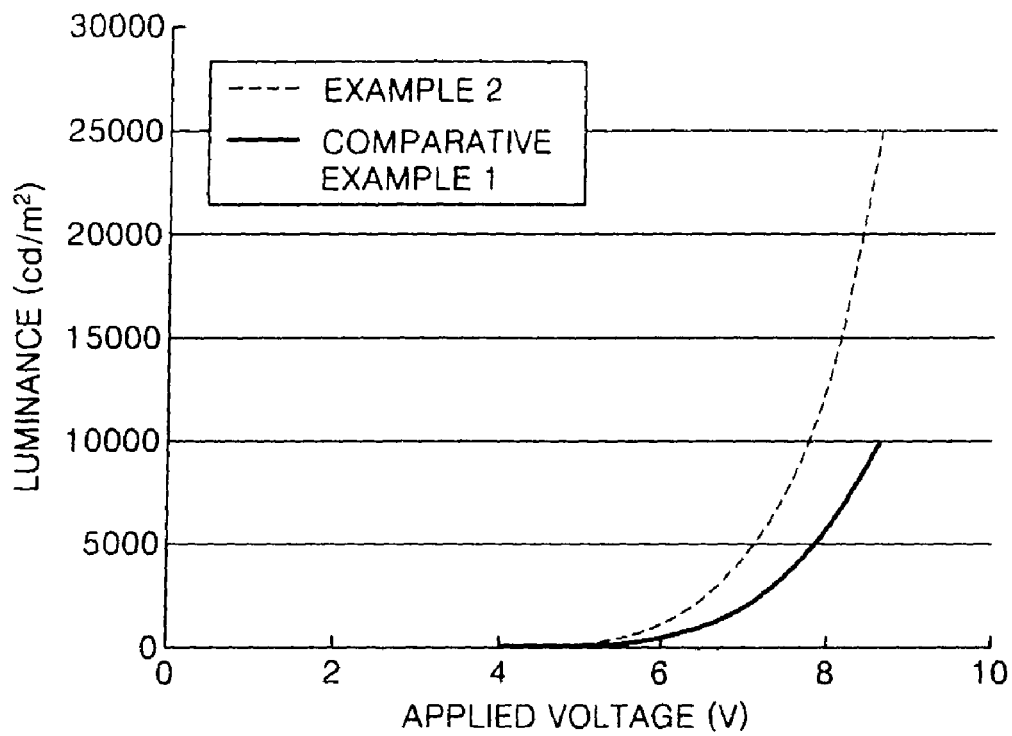
FIG. 3 is a graph of luminance according to driving voltage of organic light emitting devices prepared according to Example 2 and Comparative Example 1.
Figure 4:
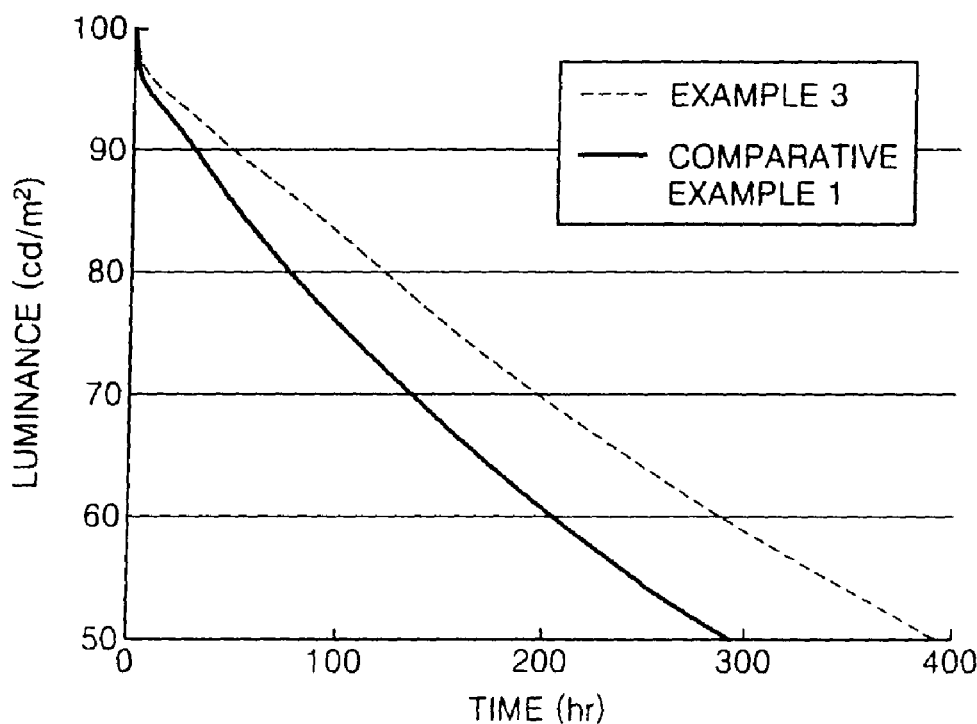
FIG. 4 is a graph of luminance according to time of organic light emitting devices prepared according to Example 3 and Comparative Example 1.

The driving voltage, current density, luminance, current efficiency and color coordinates of the organic light emitting devices obtained according to Examples 1 to 5 and Comparative Example 1 were measured using a Spectroscan spectrometer (PR650 from Photo Research Inc.). The results are shown in Table 1 below. FIG. 2 is a graph of luminance according to driving voltage of the organic light emitting devices according to Example 1 and Comparative Example 1, FIG. 3 is a graph of luminance according to driving voltage of the organic light emitting devices according to Example 2 and Comparative Example 1, and FIG. 4 is a graph of luminance according to time (100 mA/cm²) of the organic light emitting devices according to Example 3 and Comparative Example 1.

TABLE 1

| | Driving voltage (V) | Current density (mA/cm²) | Luminance (cd/m²) | Current efficiency (cd/A) | Color coordinate (x, y) |
|---|---|---|---|---|---|
| Example 1 | 6.74 | 10 | 1,036 | 10.36 | 0.146, 0.268 |
| | 8.04 | 100 | 12,030 | 12.03 | 0.146, 0.260 |
| Example 2 | 5.90 | 10 | 916 | 9.16 | 0.139, 0.244 |
| | 7.68 | 100 | 9,352 | 9.35 | 0.139, 0.239 |
| Example 3 | 5.78 | 10 | 663 | 6.63 | 0.144, 0.239 |
| | 7.34 | 100 | 6,882 | 6.88 | 0.144, 0.233 |
| Example 4 | 6.34 | 10 | 581 | 5.81 | 0.144, 0.229 |
| | 8.18 | 100 | 6,459 | 6.46 | 0.144, 0.223 |
| Example 5 | 5.52 | 10 | 610 | 6.10 | 0.144, 0.235 |
| | 7.78 | 100 | 6,360 | 6.36 | 0.144, 0.233 |
| Comparative Example 1 | 6.35 | 10 | 635 | 6.35 | 0.144, 0.229 |
| | 8.07 | 100 | 6,309 | 6.31 | 0.144, 0.223 |

As shown in Table 1, the organic light emitting devices prepared according to Examples 1 to 5 had better I-V-L characteristics compared to the organic light emitting device prepared according to Comparative Example 1. In particular, the organic light emitting device of Example 1 having an organic layer including Compound 9 as the HIL, and the organic light emitting device of Example 2 having an organic layer including Compound 43 as the HIL showed improved brightness compared to the organic light emitting device of Comparative Example 1 (Refer to FIGS. 2 and 3). In addition, the organic light emitting devices of Examples 1 to 5 had similar color coordinate characteristics to that of Comparative Example 1. The organic light emitting device of Example 3 had a longer lifetime than that of Comparative Example 1.

The silanylamine-based compounds according to the present invention have excellent electrical stability and high electron transporting capabilities. Thus, the silanylamine-based compounds of the present invention may be effectively used for red, green, blue, and white fluorescent and phosphorescent materials used to form HILs, HTLs, and EMLs in organic light emitting devices. Organic light emitting devices having high efficiency, low driving voltage, high brightness and long lifetime may be prepared using the silanylamine-based compounds of the present invention.

While the present invention has been illustrated and described with reference to certain exemplary embodiments, it is understood by those of ordinary skill in the art that various changes and modifications can be made to the described embodiments without departing from the spirit and scope of the present invention as defined by the following claims.

What is claimed is:

1. A compound comprising a silanylamine-based compound represented by Formula 1:

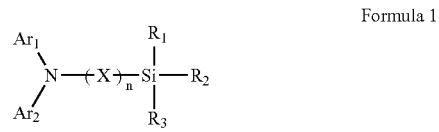

Formula 1 wherein:
X is selected from the group consisting of a single bond, substituted $C_1$-$C_{30}$ alkylene groups, unsubstituted $C_1$-$C_{30}$ alkylene groups, substituted $C_6$-$C_{30}$ arylene groups, unsubstituted $C_6$-$C_{30}$ arylene groups, substituted $C_2$-$C_{30}$ heteroarylene groups and unsubstituted $C_2$-$C_{30}$ heteroarylene groups;

n is an integer ranging from 1 to 5;

$Ar_1$ is selected from the group consisting of substituted $C_2$-$C_{30}$ heteroaryl groups, and unsubstituted $C_2$-$C_{30}$ heteroaryl groups;

$Ar_2$ is selected from the group consisting of substituted $C_6$-$C_{30}$ aryl groups, and unsubstituted $C_6$-$C_{30}$ aryl groups;

$R_1$, $R_2$ and $R_3$ are each independently selected from the group consisting of hydrogen atoms, substituted $C_1$-$C_{30}$ alkyl groups, unsubstituted $C_1$-$C_{30}$ alkyl groups, substituted $C_2$-$C_{30}$ alkenyl groups, unsubstituted $C_2$-$C_{30}$ alkenyl groups, substituted $C_2$-$C_{30}$ alkynyl groups, unsubstituted $C_2$-$C_{30}$ alkynyl groups, substituted $C_1$-$C_{30}$ alkoxy groups, unsubstituted $C_1$-$C_{30}$ alkoxy groups, substituted $C_6$-$C_{30}$ aryloxy groups, unsubstituted $C_6$-$C_{30}$ aryloxy groups, substituted $C_6$-$C_{30}$ aryl groups, unsubstituted $C_6$-$C_{30}$ aryl groups, substituted $C_2$-$C_{30}$ heteroaryl groups and unsubstituted $C_2$-$C_{30}$ heteroaryl groups; and at least two of $R_1$, $R_2$ and $R_3$ are optionally bonded to each other to form a saturated or unsaturated ring.

2. The compound of claim 1, wherein X is selected from the group consisting of substituted $C_1$-$C_{10}$ alkylene groups, unsubstituted $C_1$-$C_{10}$ alkylene groups, substituted phenylene groups, unsubstituted phenylene groups, substituted naphthylene groups, unsubstituted naphthylene groups, substituted fluorenylene groups, unsubstituted fluorenylene groups, substituted anthracenylene groups, unsubstituted anthracenylene groups, substituted pyridinylene groups, unsubstituted pyridinylene groups, substituted quinolylene groups, unsubstituted quinolylene groups, substituted isoquinolylene groups, unsubstituted isoquinolylene groups, substituted anthraquinolylene groups, unsubstituted anthraquinolylene groups, substituted carbazolylene groups, and unsubstituted carbazolylene groups.

3. The compound of claim 1, wherein X is selected from the group consisting of substituents listed in Formula 2:

Formula 2

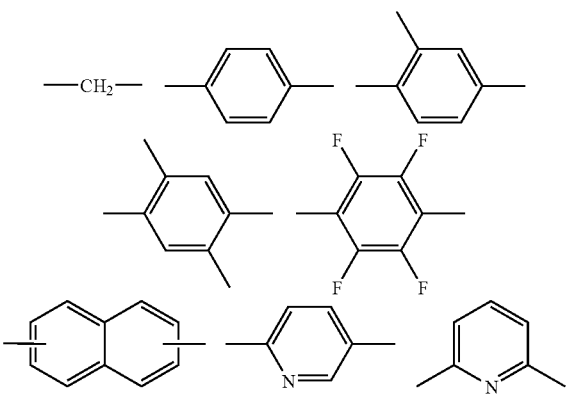

-continued

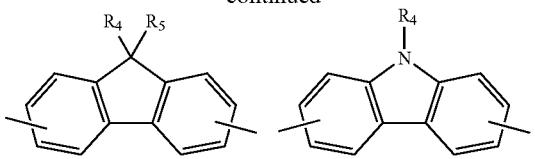

wherein $R_4$ and $R_5$ are each independently selected from the group consisting of hydrogen atoms, halogen atoms, cyano groups, hydroxyl groups, substituted $C_1$-$C_{30}$ alkyl groups, unsubstituted $C_1$-$C_{30}$ alkyl groups, substituted $C_1$-$C_{30}$ alkoxy groups, unsubstituted $C_1$-$C_{30}$ alkoxy groups, substituted $C_6$-$C_{30}$ aryl groups, unsubstituted $C_6$-$C_{30}$ aryl groups, substituted $C_3$-$C_{30}$ heteroaryl groups, and unsubstituted $C_3$-$C_{30}$ heteroaryl groups.

4. The compound of claim 3, wherein $R_4$ and $R_5$ are each independently selected from the group consisting of phenyl groups and halophenyl groups.

5. The compound of claim 1, wherein —$(X)_n$— is selected from the group consisting of substituents listed in Formula 3:

Formula 3

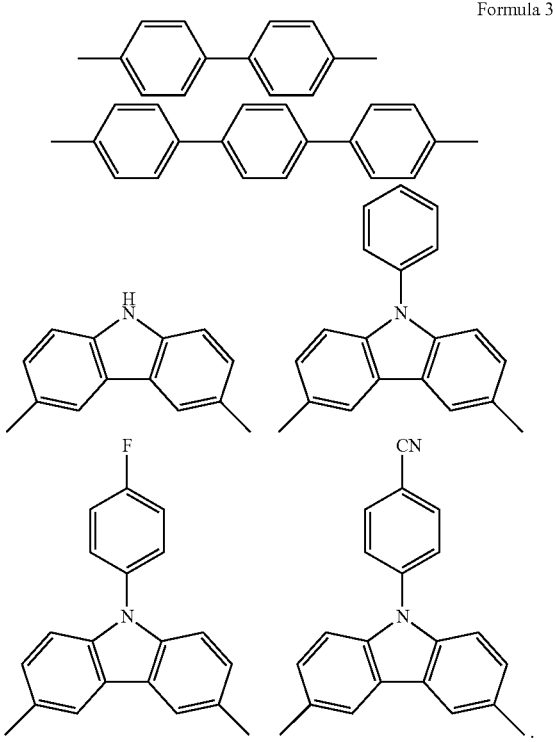

6. The compound of claim 1, wherein $Ar_1$ is selected from the group consisting of substituted $C_3$-$C_{15}$ heteroaryl groups and unsubstituted $C_3$-$C_{15}$ heteroaryl groups, and $Ar_2$ is selected from the group consisting of substituted $C_6$-$C_{12}$ aryl groups, and unsubstituted $C_6$-$C_{12}$ aryl groups.

7. The compound of claim 1, wherein $Ar_1$ is selected from the group consisting of-carbazolyl groups, halocarbazolyl groups, cyanocarbazolyl groups, $C_1$-$C_5$ alkylcarbazolyl groups, $C_1$-$C_5$ alkoxycarbazolyl groups, phenoxycarbazolyl groups, carbazolyl groups substituted with —N($Z_1$)($Z_2$), $C_6$-$C_{12}$ arylcarbazolyl groups, $C_6$-$C_{12}$ haloarylcarbazolyl groups, pyridyl groups, halopyridyl groups, cyanopyridyl groups, $C_1$-$C_5$ alkylpyridyl groups, $C_1$-$C_5$ alkoxypyridyl groups, phenoxypyridyl groups, and pyridyl groups substituted with —N($Z_1$)($Z_2$);

Ar₂ is selected from the group consisting of phenyl groups, halophenyl groups, cyanophenyl groups, $C_1$-$C_5$ alkylphenyl groups, $C_1$-$C_5$ alkoxyphenyl groups, phenoxyphenyl groups, phenyl groups substituted with —N($Z_1$)($Z_2$), biphenyl groups, halobiphenyl groups, cyanobiphenyl groups, $C_1$-$C_5$ alkylnaphthyl groups, $C_1$-$C_5$ alkoxynaphthyl groups, phenoxynaphthyl groups, naphthyl groups substituted with —N($Z_1$)($Z_2$), fluorenyl groups, halofluorenyl groups, cyanofluorenyl groups, $C_1$-$C_5$ alkylfluorenyl groups, $C_1$-$C_5$ alkoxyfluorenyl groups, and phenoxyfluorenyl groups;

wherein $Z_1$ and $Z_2$ are each independently selected from the group consisting of hydrogen atoms, substituted $C_1$-$C_{30}$ alkyl groups, unsubstituted $C_1$-$C_{30}$ alkyl groups, substituted $C_1$-$C_{30}$ haloalkyl groups, unsubstituted $C_1$-$C_{30}$ haloalkyl groups, substituted $C_6$-$C_{30}$ aryl groups, unsubstituted $C_6$-$C_{30}$ aryl groups, substituted $C_6$-$C_{30}$ haloaryl groups, unsubstituted $C_6$-$C_{30}$ haloaryl groups, substituted $C_2$-$C_{30}$ heteroaryl groups and unsubstituted $C_2$-$C_{30}$ heteroaryl groups.

8. The compound of claim 7, wherein $Z_1$ and $Z_2$ are each independently selected from the group consisting of $C_6$-$C_{12}$ aryl groups and $C_6$-$C_{12}$ haloaryl groups.

9. The compound of claim 1, wherein $Ar_1$ is selected from the group consisting of substituents listed in Formula 4A and $Ar_2$ is selected from the group consisting of substituents listed in Formula 4B:

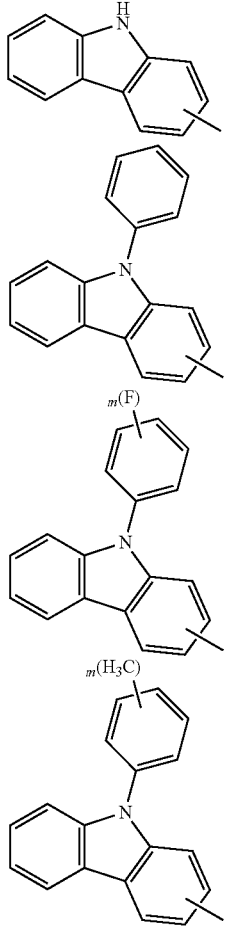

Formula 4A

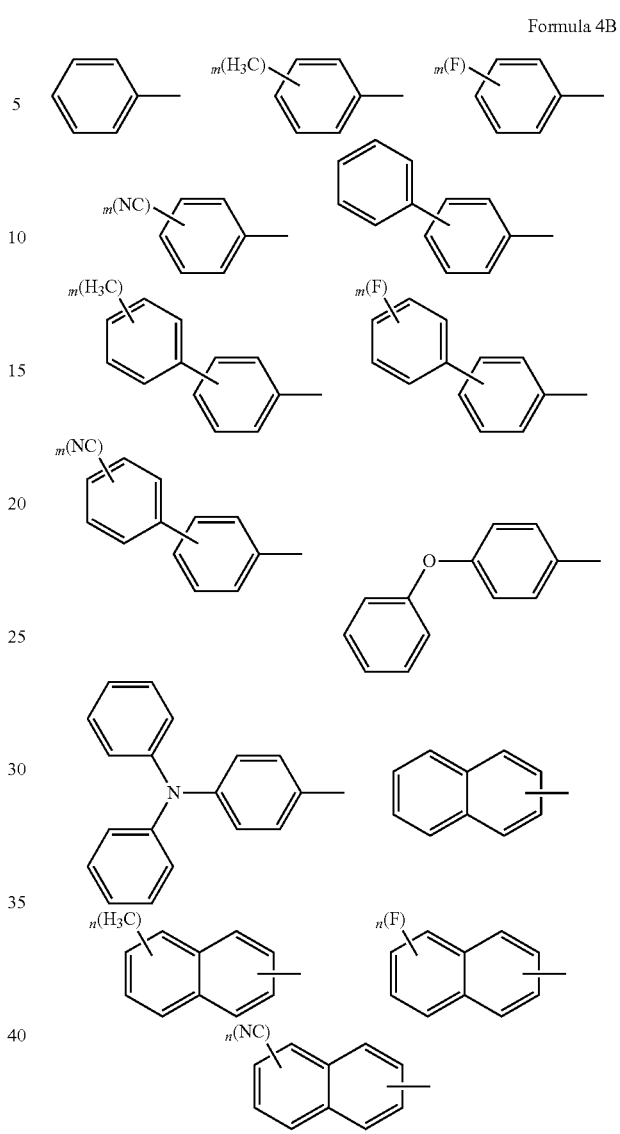

Formula 4B wherein m is an integer ranging from 1 to 5.

10. The compound of claim 1, wherein $R_1$, $R_2$, and $R_3$ are each independently selected from the group consisting of substituted $C_1$-$C_{10}$ alkyl groups, unsubstituted $C_1$-$C_{10}$ alkyl groups, substituted $C_1$-$C_{10}$ alkoxy groups, unsubstituted $C_1$-$C_{10}$ alkoxy groups, substituted $C_6$-$C_{12}$ aryl groups, unsubstituted $C_6$-$C_{12}$ aryl groups, substituted $C_6$-$C_{12}$ aryloxy groups, unsubstituted $C_6$-$C_{12}$ aryloxy groups, substituted $C_3$-$C_{12}$ heteroaryl groups and unsubstituted $C_3$-$C_{12}$ heteroaryl groups.

11. The compound of claim 1, wherein $R_1$, $R_2$ and $R_3$ are each independently selected from the group consisting of $C_1$-$C_{10}$ alkyl groups, phenyl groups, halophenyl groups, cyanophenyl groups, $C_1$-$C_{10}$ alkylphenyl groups, $C_1$-$C_{10}$ alkoxyphenyl groups, biphenyl groups, halobiphenyl groups, naphthyl groups, halonaphthyl groups, $C_1$-$C_{10}$ alkylnaphthyl groups, and $C_1$-$C_{10}$ alkoxynaphthyl groups.

12. The compound of claim 1, wherein the silanylamine-based compound is selected from the group consisting of Compounds 43, 44, 45 and 137:

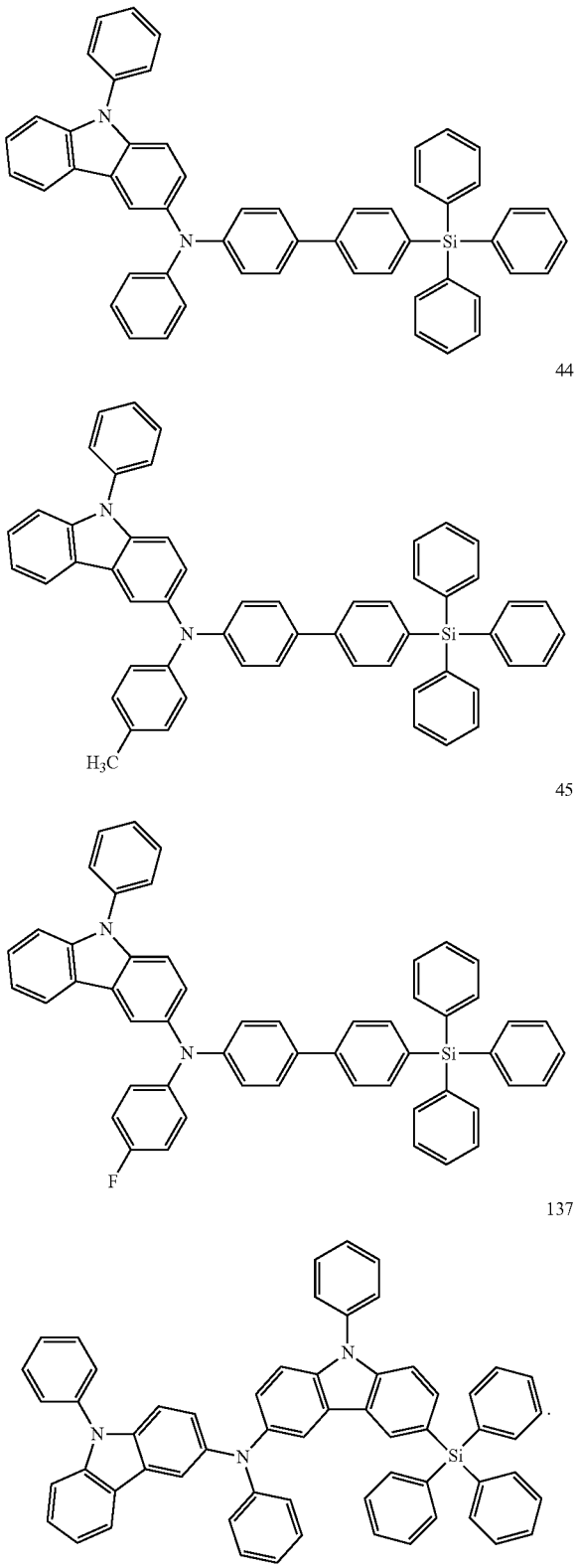

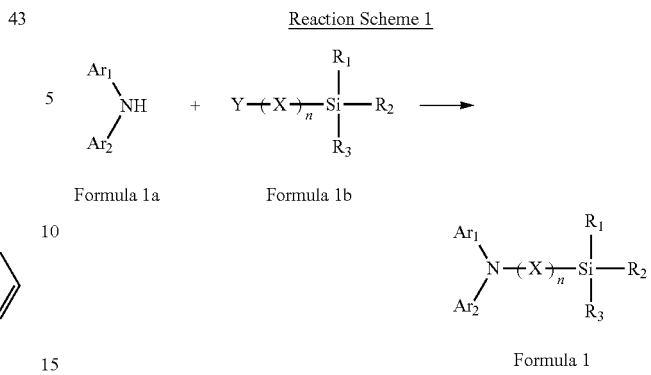

Formula 1a     Formula 1b

Formula 1

13. A method of preparing a silanylamine-based compound represented by Formula 1 comprising reacting a compound represented by Formula 1a and a compound represented by Formula 1b by Reaction Scheme 1:

wherein:
X is selected from the group consisting of a single bond, substituted $C_1$-$C_{30}$ alkylene groups, unsubstituted $C_1$-$C_{30}$ alkylene groups, substituted $C_6$-$C_{30}$ arylene groups, unsubstituted $C_6$-$C_{30}$ arylene groups, substituted $C_2$-$C_{30}$ heteroarylene groups and unsubstituted $C_2$-$C_{30}$ heteroarylene groups;

n is an integer ranging from 1 to 5;

$Ar_1$ is selected from the group consisting of substituted $C_2$-$C_{30}$ heteroaryl groups, and unsubstituted $C_2$-$C_{30}$ heteroaryl groups;

$Ar_2$ is selected from the group consisting of substituted $C_2$-$C_{30}$ heteroaryl groups, and unsubstituted $C_2$-$C_{30}$ heteroaryl groups;

$R_1$, $R_2$ and $R_3$ are each independently selected from the group consisting of hydrogen atoms, substituted $C_1$-$C_{30}$ alkyl groups, unsubstituted $C_1$-$C_{30}$ alkyl groups, substituted $C_2$-$C_{30}$ alkenyl groups, unsubstituted $C_2$-$C_{30}$ alkenyl groups, substituted $C_2$-$C_{30}$ alkynyl groups, unsubstituted $C_2$-$C_{30}$ alkynyl groups, substituted $C_1$-$C_{30}$ alkoxy groups, unsubstituted $C_1$-$C_{30}$ alkoxy groups, substituted $C_6$-$C_{30}$ aryloxy groups, unsubstituted $C_6$-$C_{30}$ aryloxy groups, substituted $C_6$-$C_{30}$ aryl groups, unsubstituted $C_6$-$C_{30}$ aryl groups, substituted $C_2$-$C_{30}$ heteroaryl groups and unsubstituted $C_2$-$C_{30}$ heteroaryl groups;

at least two of $R_1$, $R_2$ and $R_3$ are optionally bonded to each other to form a saturated or unsaturated ring; and Y is a halogen atom.

14. An organic light emitting device comprising:
a first electrode;
a second electrode; and
an organic layer positioned between the first electrode and the second electrode, wherein the organic layer comprises the compound of claim 1.

15. The organic light emitting device of claim 14, wherein the organic layer comprises one or more layers selected from the group consisting of hole injection layers, emissive layers, hole transport layers and electron transport layers.

16. The organic light emitting device of claim 14, wherein the organic layer comprises a single layer having both hole injection and hole transport capabilities.

17. The organic light emitting device of claim 15 having a structure selected from the group consisting of first electrode/hole injection layer/emissive layer/second electrode structures, first electrode/hole injection layer/hole transport layer/emissive layer/electron transport layer/second electrode structures, and first electrode/hole injection layer/hole transport layer/emissive layer /electron transport layer/electron injection layer/second electrode structures.

18. The organic light emitting device of claim 17 further comprising a layer selected from the group consisting of hole blocking layers, electron blocking layers and combinations thereof.

19. The organic light emitting device of claim 16, wherein the organic light emitting device comprises a structure selected from the group consisting of:
   first electrode/single layer having both hole injection and hole transport capabilities/emissive layer/electron transport layer/second electrode structures, and
   first electrode/single layer having both hole injection and hole transport capabilities/emissive layer/electron transport layer/electron injection layer/second electrode structures.

20. The organic light emitting device of claim 19 further comprising a layer selected from the group consisting of hole blocking layers, electron blocking layers and combinations thereof.

21. The organic light emitting device of claim 14, wherein the organic layer comprises an emissive layer.

22. The organic light emitting device of claim 21, wherein the emissive layer comprises a material selected from the group consisting of phosphorescent materials and fluorescent materials.

* * * * *

UNITED STATES PATENT AND TRADEMARK OFFICE
CERTIFICATE OF CORRECTION

| | | |
|---|---|---|
| PATENT NO. | : 7,927,719 B2 | Page 1 of 1 |
| APPLICATION NO. | : 11/777204 | |
| DATED | : April 19, 2011 | |
| INVENTOR(S) | : Seok-Hwan Hwang et al. | |

It is certified that error appears in the above-identified patent and that said Letters Patent is hereby corrected as shown below:

On the Title Page

(56) References Cited
OTHER PUBLICATIONS,
page 1, line 1.

Delete "tanslation"
Insert -- translation --

(56) References Cited
FOREIGN PATENT DOCUMENTS,
page 2, line 1.

Delete "DE 10 2004 020 A1"
Insert -- DE 10 2004 020 046 A1 --

In the Claims

Column 78, Claim 9,
Formula 4B, line 35.

Delete "$_n(H_3C)$"
Insert -- $_m(H_3C)$ --

Column 78, Claim 9,
Formula 4B, line 35.

Delete "$_n(F)$"
Insert -- $_m(F)$ --

Column 78, Claim 9,
Formula 4B, line 40.

Delete "$_n(NC)$"
Insert -- $_m(NC)$ --

Signed and Sealed this
Tenth Day of July, 2012

David J. Kappos
*Director of the United States Patent and Trademark Office*